United States Patent
Cheng et al.

(10) Patent No.: US 9,181,235 B2
(45) Date of Patent: Nov. 10, 2015

(54) SUBSTITUTED PYRIDINES FOR MODULATING THE WNT SIGNALING PATHWAY

(75) Inventors: Dai Cheng, San Diego, CA (US); Guobao Zhang, San Diego, CA (US); Dong Han, San Diego, CA (US); Wenqi Gao, San Diego, CA (US); Shifeng Pan, San Diego, CA (US); Lichun Shen, Ledgewood, NJ (US); Rajender Reddy Leleti, Randolph, NJ (US)

(73) Assignee: NOVARTIS AG, Lichtstrasse, Basel (CH)

( * ) Notice: Subject to any disclaimer, the term of this patent is extended or adjusted under 35 U.S.C. 154(b) by 210 days.

(21) Appl. No.: 13/701,982

(22) PCT Filed: Jun. 28, 2011

(86) PCT No.: PCT/US2011/042215
§ 371 (c)(1),
(2), (4) Date: Dec. 4, 2012

(87) PCT Pub. No.: WO2012/003189
PCT Pub. Date: Jan. 5, 2012

(65) Prior Publication Data
US 2013/0079328 A1  Mar. 28, 2013

Related U.S. Application Data

(60) Provisional application No. 61/359,569, filed on Jun. 29, 2010.

(51) Int. Cl.
| | |
|---|---|
| A61K 31/444 | (2006.01) |
| C07D 213/81 | (2006.01) |
| C07D 417/14 | (2006.01) |
| C07D 213/56 | (2006.01) |
| C07D 237/08 | (2006.01) |
| C07D 279/12 | (2006.01) |
| C07D 401/12 | (2006.01) |
| C07D 401/14 | (2006.01) |
| C07D 403/12 | (2006.01) |
| A61K 31/50 | (2006.01) |
| A61K 31/541 | (2006.01) |
| A61K 45/06 | (2006.01) |

(52) U.S. Cl.
CPC .............. *C07D 417/14* (2013.01); *A61K 31/50* (2013.01); *A61K 31/541* (2013.01); *A61K 45/06* (2013.01); *C07D 213/56* (2013.01); *C07D 237/08* (2013.01); *C07D 279/12* (2013.01); *C07D 401/12* (2013.01); *C07D 401/14* (2013.01); *C07D 403/12* (2013.01)

(58) Field of Classification Search
CPC ........................ A61K 31/444; C07D 213/81
USPC ......... 514/248, 357, 332, 256, 255.05, 227.8, 514/253.01, 252.03, 343, 354; 544/238, 544/224, 333, 58.4, 364, 405, 359, 60; 546/329, 268.1, 323; 548/543
See application file for complete search history.

(56) References Cited

U.S. PATENT DOCUMENTS 7,947,277 B2 *  5/2011  Ernst et al. ................. 424/179.1

FOREIGN PATENT DOCUMENTS

| WO | WO2004046117 | 6/2004 |
|---|---|---|
| WO | WO2004072025 | 8/2004 |
| WO | WO2009058298 | 5/2009 |
| WO | WO2009075874 | 6/2009 |
| WO | WO2010101849 | 9/2010 |
| WO | WO 2012/003189 | * 1/2012 |

OTHER PUBLICATIONS

Jordan, V. C. Nature Reviews: Drug Discovery, 2, 2003, 205.*
Hackam, et al. JAMA, 296(14), 2006, 1731-1732.*
Kypta, "GSK-3 inhibitors and their potential in the treatment of Alzheimer's disease", Expert Opinion on Therapeutic Patents, Informa Healthcare, Oct. 1, 2005, pp. 1315-1331, vol. 15, No. 10, Ashley Publications Ltd., Great Britain.

* cited by examiner

*Primary Examiner* — Douglas M Willis
(74) *Attorney, Agent, or Firm* — Emily T. Wu, J.D.; Genomics Institute of the Novartis Research Foundation

(57) ABSTRACT

The present invention relates to compositions and methods for modulating the Wnt signaling pathway, using compounds having Formula (1) and (3): wherein A, B, Y and Z all represent rings, and $R^1$, $R^2$, $R^3$ are as defined herein.

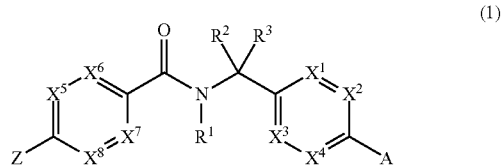

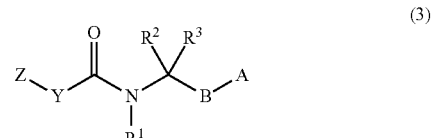

15 Claims, No Drawings

US 9,181,235 B2

SUBSTITUTED PYRIDINES FOR MODULATING THE WNT SIGNALING PATHWAY

CROSS-REFERENCE TO RELATED APPLICATIONS

This application is a 371 U.S. national phase application of international application number PCT/US2011/042215 filed 28 Jun. 2011, which application claims priority to U.S. provisional patent application No. 61/359,569 filed 29 Jun. 2010. The full disclosure of this application is incorporated herein by reference in its entirety and for all purposes.

TECHNICAL FIELD

The present invention relates to compositions and methods for modulating the Wnt signaling pathway.

BACKGROUND

The Wnt gene family encodes a large class of secreted proteins related to the Int1/Wnt1 proto-oncogene and *Drosophila* wingless ("Wg"), a *Drosophila* Wnt1 homologue. (Cadigan et al. (1997) Genes & Development 11:3286-3305). Wnts are expressed in a variety of tissues and organs and play a major role in many developmental processes, including segmentation in *Drosophila*; endoderm development in *C. elegans*; and establishment of limb polarity, neural crest differentiation, kidney morphogenesis, sex determination, and brain development in mammals. (Parr, et al. (1994) Curr. Opinion Genetics & Devel. 4:523-528). The Wnt pathway is a master regulator in animal development, both during embryogenesis and in the mature organism. (Eastman, et al. (1999) Curr Opin Cell Biol 11: 233-240; Peifer, et al. (2000) Science 287: 1606-1609).

Wnt signals are transduced by the Frizzled ("Fz") family of seven transmembrane domain receptors. (Bhanot et al. (1996) Nature 382:225-230). Wnt ligands bind to Fzd, and in so doing, activate the cytoplasmic protein Dishevelled (Dvl-1, 2 and 3 in humans and mice) (Boutros, et al. (1999) Mech Dev 83: 27-37) and phosphorylate LRP5/6. A signal is thereby generated which prevents the phosphorylation and degradation of Armadillo/β(beta)-catenin, in turn leading to the stabilization of β-catenin (Perrimon (1994) Cell 76:781-784). This stabilization is occasioned by Dvl's association with axin (Zeng et al. (1997) Cell 90:181-192), a scaffolding protein that brings various proteins together, including GSK3, APC, CK1, and β-catenin, to form the β-catenin destruction complex.

The Wingless-type (Wnt) Frizzled protein receptor pathway involves important regulatory genes that carry polymorphisms associated with primary carcinomas. In the course of downstream signaling, cytosolic β-catenin accumulates, translocates into the nucleus, and then enhances gene expression by complexing with other transcription factors. (Uthoff et al., *Mol Carcinog*, 31:56-62 (2001)). In the absence of Wnt signals, free cytosolic β-catenin is incorporated into a complex consisting of Axin, the adenomatous polyposis coli (APC) gene product, and glycogen synthase kinase (GSK)-3β. Conjunctional phosphorylation of Axin, APC, and β-catenin by GSK-3β designates β-catenin for the ubiquitin pathway and degradation by proteasomes. (Uthoff et al., *Mol Carcinog*, 31:56-62 (2001); Matsuzawa et al., *Mol Cell*, 7:915-926 (2001)).

Wnt/β-catenin signaling promotes cell survival in various cell types. (Orford et al., J Cell Biol, 146:855-868 (1999); Cox et al., Genetics, 155:1725-1740 (2000); Reya et al., Immunity, 13:15-24 (2000); Satoh et al., Nat Genet, 24:245-250 (2000); Shin et al., Journal of Biological Chemistry, 274:2780-2785 (1999); Chen et al., J Cell Biol, 152:87-96 (2001); Ioannidis et al., Nat Immunol, 2:691-697 (2001)). Wnt signaling pathway is also thought to be associated with tumor development and/or progression. (Polakis et al., Genes Dev, 14:1837-1851 (2000); Cox et al., Genetics, 155:1725-1740 (2000); Bienz et al., Cell, 103:311-320 (2000); You et al., J Cell Biol, 157:429-440 (2002)). Aberrant activation of the Wnt signaling pathway is associated with a variety of human cancers, correlating with the over-expression or amplification of c-Myc. (Polakis et al., Genes Dev, 14:1837-1851 (2000); Bienz et al., Cell, 103:311-320 (2000); Brown et al., Breast Cancer Res, 3:351-355 (2001); He et al., Science, 281:1509-1512 (1998); Miller et al., Oncogene, 18:7860-7872 (1999)). In addition, c-Myc was identified as one of the transcriptional targets of the β-catenin/Tcf in colorectal cancer cells. (He et al., Science, 281:1509-1512 (1998); de La Coste et al., Proc Natl Acad Sci USA, 95:8847-8851 (1998); Miller et al., Oncogene, 18:7860-7872 (1999); You et al., J Cell Biol, 157:429-440 (2002)).

International Application Number PCT/US2010/025813 describes N-(hetero)aryl, 2-(hetero)aryl-substituted acetamides for use as Wnt signaling modulators.

A need exists for agents and methods that modulate the Wnt signaling pathway, for example, agents having functional activity as Wnt inhibitors, thereby treating, diagnosing, preventing, and/or ameliorating Wnt signaling-related disorders. Furthermore, the ideal drug candidate should exist in a physical form that is stable, non-hygroscopic and easily formulated.

DISCLOSURE OF THE INVENTION

The present invention relates to compositions and methods for modulating the Wnt signaling pathway. In one embodiment, the present invention provides compounds for inhibiting the Wnt signaling pathway, and that exhibit a desirable stability and solubility.

In a first embodiment, the present invention provides a compound having Formula (1):

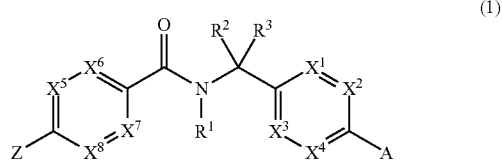

or a pharmaceutically acceptable salt thereof, wherein:
A is

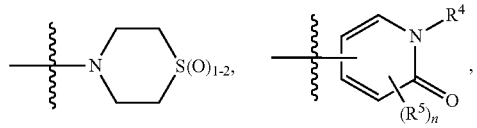

-continued

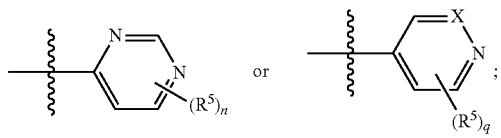

X is N, CH or CR$^6$;
X$^1$, X$^2$, X$^3$ and X$^4$ are independently N or CR$^{11}$;
X$^5$, X$^6$, X$^7$ and X$^8$ are independently N or CR$^{12}$;
Z is unsubstituted or substituted by 1-2 R$^7$ groups, and is aryl, 5-6 membered heterocyclic ring, or a 5-6 membered heteroaryl; wherein said heterocyclic ring and heteroaryl independently contain 1-2 heteroatoms selected from N, O and S;
R$^1$, R$^2$, R$^3$ and R$^4$ are hydrogen or C$_{1-6}$ alkyl;
R$^5$ and R$^6$ are independently halo, cyano, C$_{1-6}$alkoxy, S(O)$_2$ R$^{10}$, or a C$_{1-6}$ alkyl unsubstituted or substituted with halo;
R$^7$ is hydrogen, halo, cyano, C$_{1-6}$alkoxy, C$_{1-6}$ alkyl, C$_{2-6}$ alkenyl or C$_{2-6}$ alkynyl, each of which is unsubstituted or substituted by halo, amino, hydroxyl, alkoxy or cyano; -L-W, NR$^8$R$^9$, -L-C(O)R$^{10}$, -L-C(O)OR$^{10}$, -L-C(O)NR$^8$R$^9$, OR$^9$; -L-S(O)$_2$R$^{10}$ or -L-S(O)$_2$NR$^8$R$^9$;
R$^8$ and R$^9$ are independently hydrogen, -L-W, or C$_{1-6}$ alkyl, C$_{2-6}$ alkenyl or C$_{2-6}$ alkynyl, each of which is unsubstituted or substituted by halo, amino, hydroxyl, alkoxy or cyano; alternatively, R$^8$ and R$^9$ together with the atoms to which they are attached may form a ring;
R$^{10}$ is C$_{1-6}$ alkyl or -L-W;
R$^{11}$ and R$^{12}$ are independently hydrogen, halo, cyano, C$_{1-6}$alkoxy, or a C$_{1-6}$ alkyl unsubstituted or substituted by halo; and
L is a bond or (CR$_2$)$_{1-4}$ wherein R is H or C$_{1-6}$ alkyl;
W is C$_{3-7}$cycloalkyl, aryl, 5-6 membered heterocyclic ring, or 5-6 membered heteroaryl;
wherein said heterocyclic ring and heteroaryl independently contain 1-3 heteroatoms selected from N, O and S; and
n and q are independently 0-3.

In a second embodiment, the present invention provides a compound of Formula (1), wherein:

A is

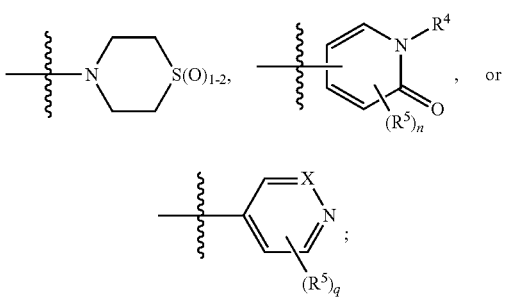

X is N, CH or CR$^6$;
X$^1$, X$^2$, X$^3$ and X$^4$ are independently N or CR$^{11}$;
X$^5$, X$^6$, X$^7$ and X$^8$ are independently N or CR$^{12}$;
Z is unsubstituted or substituted by 1-2 R$^7$ groups, and is aryl, 5-6 membered heterocyclic ring, or a 5-6 membered heteroaryl; wherein said heterocyclic ring and heteroaryl independently contain 1-2 heteroatoms selected from N, O and S;

R$^1$, R$^2$ and R$^3$ are hydrogen;
R$^4$ is hydrogen or C$_{1-6}$ alkyl;
R$^5$ and R$^6$ are independently halo, or a C$_{1-6}$ alkyl unsubstituted or substituted by halo;
R$^7$ is halo, cyano, C$_{1-6}$ alkyl, NR$^8$R$^9$, -L-C(O)R$^{10}$, -L-C(O)OR$^{10}$ or -L-S(O)$_2$R$^{10}$ wherein L is a bond;
R$^8$ and R$^9$ are independently hydrogen or C$_{1-6}$ alkyl; alternatively, R$^8$ and R$^9$ together with nitrogen in NR$^8$R$^9$ form a 5-6 membered heterocyclyl;
R$^{10}$ is C$_{1-6}$ alkyl;
R$^{11}$ and R$^{12}$ are independently hydrogen, halo or C$_{1-6}$ alkyl; and n and q are 0-1.

In a third embodiment, the present invention provides a compound of Formula (2):

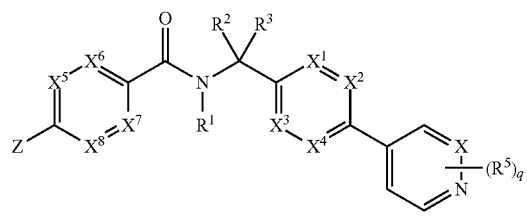

or a pharmaceutically acceptable salt thereof, wherein:
Z is unsubstituted or substituted by 1-2 R$^7$ groups, and is aryl or a 5-6 membered heteroaryl containing 1-2 nitrogen heteroatoms;
X is N, CH or CR$^6$;
X$^1$, X$^2$, X$^3$ and X$^4$ are independently N or CR$^{11}$;
X$^5$, X$^6$, X$^7$ and X$^8$ are independently N or CR$^{12}$;
R$^1$, R$^2$ and R$^3$ are hydrogen;
R$^5$ and R$^6$ are independently halo, or a C$_{1-6}$ alkyl unsubstituted or substituted by halo;
R$^7$ is halo, cyano, C$_{1-6}$ alkyl, NR$^8$R$^9$, -L-C(O)R$^{10}$, -L-C(O)OR$^{10}$ or -L-S(O)$_2$R$^{10}$ wherein L is a bond;
R$^8$ and R$^9$ are independently hydrogen or C$_{1-6}$ alkyl; alternatively, R$^8$ and R$^9$ together with nitrogen in NR$^8$R$^9$ form a 5-6 membered heterocyclyl;
R$^{10}$ is C$_{1-6}$ alkyl;
R$^{11}$ and R$^{12}$ are independently hydrogen, halo or C$_{1-6}$ alkyl; and
n and q are 0-1.

In any of the above first, second or third embodiments, X$^1$, X$^2$, X$^3$ and X$^4$ can be CR$^{11}$; and X$^5$, X$^6$, X$^7$ and X$^8$ are CR$^{12}$. Alternatively, one of X$^1$, X$^2$, X$^3$ and X$^4$ is N and the others are CR$^{11}$; and X$^5$, X$^6$, X$^7$ and X$^8$ are CR$^{12}$. Also described herein are compounds wherein X$^1$, X$^2$, X$^3$ and X$^4$ are CR$^{11}$; one of X$^5$, X$^6$, X$^7$ and X$^8$ is N and the others are CR$^{12}$. Also described herein are compounds wherein one of X$^1$, X$^2$, X$^3$ and X$^4$ is N and the others are CR$^{11}$; one of X$^5$, X$^6$, X$^7$ and X$^8$ is N and the others are CR$^{12}$. In particular embodiments, one of X$^1$, X$^2$, X$^3$ and X$^4$ is N and the others are CR$^{11}$; one of X$^5$, X$^6$, X$^7$ and X$^8$ is N and the others are CH. In each embodiment, R$^{11}$ and R$^{12}$ are as defined in Formula (1) or (2).

In a fourth embodiment, the present invention provides a compound of Formula (2A):

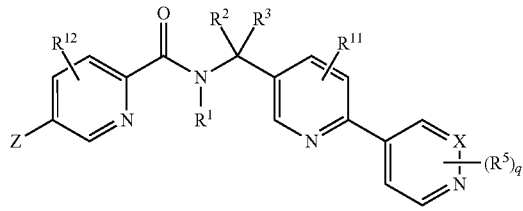

(2A)

or a pharmaceutically acceptable salt thereof, wherein:

X is N, CH or $CR^6$;

Z is unsubstituted or substituted by 1-2 $R^7$ groups, and is aryl or a 5-6 membered heteroaryl containing 1-2 nitrogen heteroatoms;

$R^1$, $R^2$ and $R^3$ are hydrogen;

$R^5$ and $R^6$ are independently halo, or a $C_{1-6}$ alkyl unsubstituted or substituted by halo;

q is 0;

$R^7$ is halo, cyano, $C_{1-6}$ alkyl, $NR^8R^9$, -L-C(O)$R^{10}$, -L-C(O)O$R^{10}$ or -L-S(O)$_2R^{10}$ wherein L is a bond;

$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;

$R^{10}$ is $C_{1-6}$ alkyl;

$R^{11}$ is hydrogen, halo or methyl; and $R^{12}$ is hydrogen or methyl.

In a fifth embodiment, the present invention provides a compound of Formula (3):

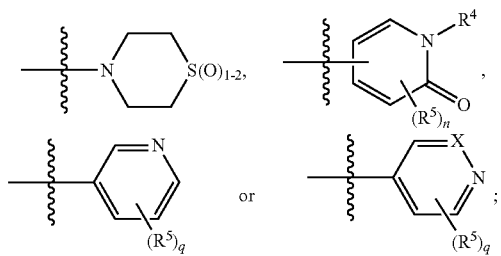

(3)

or a pharmaceutically acceptable salt thereof, wherein:
wherein A is

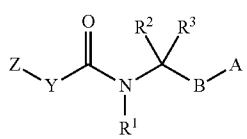

X is N, CH or $CR^6$;

B and Y are independently phenyl, or a 6-membered heteroaryl ring comprising 1-2 nitrogen heteroatoms, wherein said phenyl is unsubstituted or substituted by $R^{7a}$ and said 6-membered heteroaryl is unsubstituted or substituted by $R^{7b}$; or one of B and Y is pyridyl unsubstituted or substituted by $C_{1-6}$ alkyl, and the other is

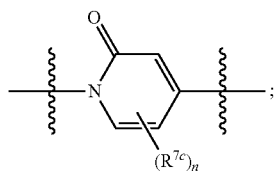

Z is optionally substituted with 1-2 $R^{7d}$ groups and is aryl, a 5-6 membered heterocyclic ring, or a 5-6 membered heteroaryl; wherein said heterocyclic ring and heteroaryl independently comprise 1-2 heteroatoms selected from N, O and S;

$R^1$, $R^2$ and $R^3$ are hydrogen;

$R^4$ is hydrogen or $C_{1-6}$ alkyl;

$R^5$, $R^6$ and $R^{7c}$ are independently halo, or a $C_{1-6}$ alkyl optionally substituted with halo;

$R^{7a}$ and $R^{7b}$ are independently halo or $C_{1-6}$ alkyl;

$R^{7d}$ is halo, cyano, $C_{1-6}$ alkyl, $NR^8R^9$, -L-C(O)$R^{10}$, -L-C(O)O$R^{10}$ or -L-S(O)$_2R^{10}$ wherein L is a bond;

$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;

$R^{10}$ is $C_{1-6}$ alkyl; and n and q are 0-1.

In a sixth embodiment, the invention provides a compound of Formula (3) as defined above, with the proviso that A is

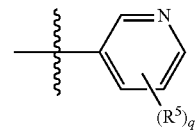

when B and Y are independently phenyl, or a 6-membered heteroaryl ring comprising 1-2 nitrogen heteroatoms.

In any of the above first through sixth embodiments, the present invention provides a compound of Formula (1), (2), (2A), and (3), wherein Z is phenyl, pyridonyl, piperazinyl, piperidinyl, pyridinyl, pyridazine, pyrazine, pyrimidine, pyrazole, morpholinyl or 1,2,3,6-tetrahydropyridine, each of which is optionally substituted with 1-2 $R^7$ or $R^{7c}$ groups; and wherein the —NH— moiety in said piperazinyl and piperidinyl is optionally substituted with -L-C(O)$R^{10}$ or -L-C(O)O$R^{10}$; and $R^7$ and $R^{10}$ are as defined in Formula (1). In particular embodiments, Z is phenyl unsubstituted or substituted by 1-2 halo, cyano, $C_{1-6}$ alkyl, $NR^8R^9$, -L-C(O)$R^{10}$ or -L-S(O)$_2R^{10}$; pyridinyl unsubstituted or substituted by $C_{1-6}$ alkyl or $NR^8R^9$; piperazinyl unsubstituted or wherein the —NH— moiety in said piperazinyl is substituted by -L-C(O)$R^{10}$ or -L-C(O)O$R^{10}$; 2-oxo-pyridyl, pyridazinyl, pyrazinyl, pyrimidinyl; $R^8$ and $R^9$ are independently hydrogen or $C_{1-6}$ alkyl; alternatively, $R^8$ and $R^9$ together with nitrogen in $NR^8R^9$ form 2-oxo-pyrrolidinyl; $R^{10}$ is $C_{1-6}$ alkyl; and L is a bond. In preferred embodiments, Z is pyridinyl, pyridazine, pyrazine or pyrimidine.

In a seventh embodiment, the invention provides a compound of Formula (3), wherein a substituent is defined independently, collectively, or in any combination or sub-combination, as follows:

a) A is

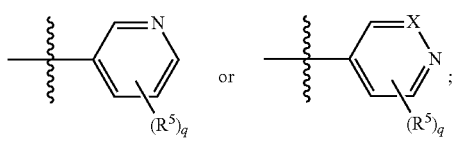

or b) B and Y are phenyl; alternatively, one of B and Y is pyridyl unsubstituted or substituted by $C_{1-6}$ alkyl, and the other is

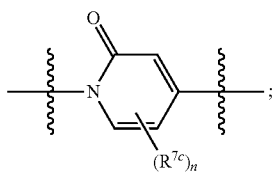

c) Z is pyrazinyl or phenyl substituted with halo; and
d) n is 0.

In any of the above first through seventh embodiments, the present invention provides a compound of Formula (1), (2), (2A), and (3), wherein X is CH or $CR^6$, and $R^6$ is halo, methyl, difluoromethyl or trifluoromethyl; and more particularly, wherein $R^6$ is halo, methyl or trifluoromethyl.

In an eighth embodiment, the present invention also provides a process for the production of a compound of Formula (2A), (2A)

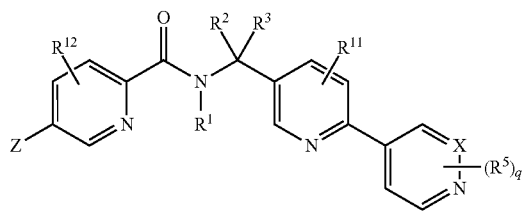

comprising reacting a compound of Formula (5)

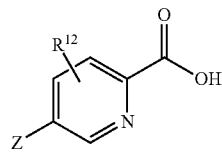

with a compound of Formula (6)

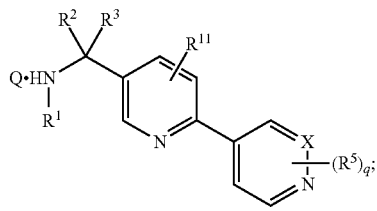

wherein X is N, CH or $CR^6$;
Z is unsubstituted or substituted by 1-2 $R^7$ groups, and is aryl or a 5-6 membered heteroaryl containing 1-2 nitrogen heteroatoms;
$R^1$, $R^2$ and $R^3$ are hydrogen;
$R^5$ and $R^6$ are independently halo, or a $C_{1-6}$ alkyl unsubstituted or substituted by halo;

q is 0;
$R^7$ is halo, cyano, $C_{1-6}$ alkyl, $NR^8R^9$, -L-C(O)$R^{10}$, -L-C(O)OR$^{10}$ or -L-S(O)$_2R^{10}$ wherein L is a bond;
$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;
$R^{10}$ is $C_{1-6}$ alkyl;
$R^{11}$ is hydrogen, halo or methyl; and
$R^{12}$ is hydrogen or methyl;
Q is an organic acid or inorganic acid; and
recovering the resulting compound of Formula (2A) in free form or as a salt, and when desired, converting the compound of Formula (2A) obtained in free form into the desired salt, or an obtained salt in free form.

The process for the production of a compound of Formula (2A) can be carried out with any suitable organic acid or inorganic acid known to those skilled in the art, and more particularly, with hydrochloric acid, sulfuric acid, acetic acid, or succinic acid.

Specific compounds of Formula (1), (2), (2A), and (3) include those selected from the group consisting of:
4-phenyl-N-{[4-(pyridazin-4-yl)phenyl]methyl}benzamide;
4-(3-fluorophenyl)-N-{[4-(pyridazin-4-yl)phenyl]methyl}benzamide;
N-((6-(1,1-dioxidothiomorpholino)pyridin-3-yl)methyl)-3'-fluoro-[1,1'-biphenyl]-4-carboxamide;
N-((6-(1,1-dioxidothiomorpholino)pyridin-3-yl)methyl)-6-(3-fluorophenyl)nicotinamide;
N-((6-(1,1-dioxidothiomorpholino)pyridin-3-yl)methyl)-[2,3'-bipyridine]-5-carboxamide;
N-((6-(1,1-dioxidothiomorpholino)pyridin-3-yl)methyl)-5-(3-fluorophenyl)picolinamide;
methyl 4-(4-(((6-(1,1-dioxidothiomorpholino)pyridin-3-yl)methyl)carbamoyl)phenyl)piperazine-1-carboxylate;
3'-fluoro-N-((6-(1-oxidothiomorpholino)pyridin-3-yl)methyl)-[1,1'-biphenyl]-4-carboxamide;
N-{[4-(2-methylpyridin-4-yl)phenyl]methyl}-4-phenylbenzamide;
4-phenyl-N-{[4-(pyridin-3-yl)phenyl]methyl}benzamide;
N-{[4-(4-methyl-1H-imidazol-1-yl)phenyl]methyl}-4-phenylbenzamide;
4-(3-fluorophenyl)-N-{[4-(2-methylpyridin-4-yl)phenyl]methyl}benzamide;
N-{[4-(2-methylpyridin-4-yl)phenyl]methyl}-4-(pyridin-2-yl)benzamide;
N-{[4-(2-methylpyridin-4-yl)phenyl]methyl}-5-phenylpyridine-2-carboxamide;
N-{[3-fluoro-4-(2-methylpyridin-4-yl)phenyl]methyl}-4-(pyrimidin-5-yl)benzamide;
N-{[4-(2-methylpyridin-4-yl)phenyl]methyl}-4-(pyrimidin-5-yl)benzamide;
N-{[4-(2-methylpyridin-4-yl)phenyl]methyl}-4-(pyrazin-2-yl)benzamide;
N-{[6-(2-methylpyridin-4-yl)pyridin-3-yl]methyl}-4-(pyrazin-2-yl)benzamide;
N-{[4-(2-methylpyridin-4-yl)phenyl]methyl}-6-(pyridazin-4-yl)pyridine-3-carboxamide;
6-(4-acetylpiperazin-1-yl)-N-{[3-fluoro-4-(2-methylpyridin-4-yl)phenyl]methyl}pyridine-3-carboxamide;
N-{[3-fluoro-4-(1-methyl-6-oxo-1,6-dihydropyridin-3-yl)phenyl]methyl}-4-(pyrazin-2-yl)benzamide;
5-(4-acetylpiperazin-1-yl)-N-{[3-fluoro-4-(2-methylpyridin-4-yl)phenyl]methyl}pyridine-2-carboxamide;
4-(3-fluorophenyl)-N-{[6-(2-methylpyridin-4-yl)pyridin-3-yl]methyl}benzamide;
N-{[6-(2-fluoropyridin-4-yl)pyridin-3-yl]methyl}-4-(pyrazin-2-yl)benzamide;

6-[6-(dimethylamino)pyridin-3-yl]-N-{[6-(2-fluoropyridin-4-yl)pyridin-3-yl]methyl}pyridine-3-carboxamide;
5-(3-fluorophenyl)-N-{[6-(2-methylpyridin-4-yl)pyridin-3-yl]methyl}pyridine-2-carboxamide;
6-(3-fluorophenyl)-N-{[6-(2-methylpyridin-4-yl)pyridin-3-yl]methyl}pyridine-3-carboxamide;
4-(pyrazin-2-yl)-N-({4-[2-(trifluoromethyl)pyridin-4-yl]phenyl}methyl)benzamide;
5-[3-(dimethylamino)phenyl]-N-{[6-(2-methylpyridin-4-yl)pyridin-3-yl]methyl}pyridine-2-carboxamide;
5-(3-fluorophenyl)-N-{[6-(2-fluoropyridin-4-yl)-5-methylpyridin-3-yl]methyl}pyridine-2-carboxamide;
5-(3-acetylphenyl)-N-{[6-(2-methylpyridin-4-yl)pyridin-3-yl]methyl}pyridine-2-carboxamide;
4-(pyrazin-2-yl)-N-({6-[2-(trifluoromethyl)pyridin-4-yl]pyridin-3-yl}methyl)benzamide;
5-(3-fluorophenyl)-N-({6-[2-(trifluoromethyl)pyridin-4-yl]pyridin-3-yl}methyl)pyridine-2-carboxamide;
5-(3-cyanophenyl)-N-{[6-(2-methylpyridin-4-yl)pyridin-3-yl]methyl}pyridine-2-carboxamide;
5-(4-fluorophenyl)-N-{[6-(2-methylpyridin-4-yl)pyridin-3-yl]methyl}pyridine-2-carboxamide;
5-(3-fluorophenyl)-N-{[5-methyl-6-(2-methylpyridin-4-yl)pyridin-3-yl]methyl}pyridine-2-carboxamide;
N-{[6-(2-fluoropyridin-4-yl)pyridin-3-yl]methyl}-5-(pyridazin-4-yl)pyridine-2-carboxamide;
5-[6-(dimethylamino)pyridin-3-yl]-N-{[6-(2-fluoropyridin-4-yl)pyridin-3-yl]methyl}pyridine-2-carboxamide;
N-{[6-(2-fluoropyridin-4-yl)-5-methylpyridin-3-yl]methyl}-5-(pyrazin-2-yl)pyridine-2-carboxamide;
N-{[6-(2-fluoropyridin-4-yl)-5-methylpyridin-3-yl]methyl}-6-(pyrazin-2-yl)pyridine-3-carboxamide;
5-(pyrazin-2-yl)-N-({6-[2-(trifluoromethyl)pyridin-4-yl]pyridin-3-yl}methyl)pyridine-2-carboxamide;
6-(pyrazin-2-yl)-N-({6-[2-(trifluoromethyl)pyridin-4-yl]pyridin-3-yl}methyl)pyridine-3-carboxamide;
N-{[6-(2-fluoropyridin-4-yl)pyridin-3-yl]methyl}-5-(3-methanesulfonylphenyl)pyridine-2-carboxamide;
N-{[6-(2-fluoropyridin-4-yl)pyridin-3-yl]methyl}-5-(2-oxo-1,2-dihydropyridin-1-yl)pyridine-2-carboxamide;
4-(2-methylphenyl)-N-{[6-(2-methylpyridin-4-yl)pyridin-3-yl]methyl}benzamide;
6-(3-fluorophenyl)-N-({1-[(2-fluoropyridin-4-yl)carbonyl]piperidin-4-yl}methyl)pyridine-3-carboxamide;
6-(3-fluorophenyl)-N-({5-methyl-6-[2-(trifluoromethyl)pyridin-4-yl]pyridin-3-yl}methyl)pyridine-3-carboxamide;
5-(4-acetylpiperazin-1-yl)-N-({5-methyl-6-[2-(trifluoromethyl)pyridin-4-yl]pyridin-3-yl}methyl)pyridine-2-carboxamide;
3-methyl-N-{[6-(2-methylpyridin-4-yl)pyridin-3-yl]methyl}-4-phenylbenzamide;
5-(3-fluorophenyl)-N-{[5-(2-methylpyridin-4-yl)pyridin-2-yl]methyl}pyridine-2-carboxamide;
N-{[6-(2-fluoropyridin-4-yl)-5-methylpyridin-3-yl]methyl}-6-(pyridazin-3-yl)pyridine-3-carboxamide;
N-({5-methyl-6-[2-(trifluoromethyl)pyridin-4-yl]pyridin-3-yl}methyl)-6-(pyridazin-3-yl)pyridine-3-carboxamide;
N-({5-methyl-6-[2-(trifluoromethyl)pyridin-4-yl]pyridin-3-yl}methyl)-6-(pyrazin-2-yl)pyridine-3-carboxamide;
N-({5-methyl-6-[2-(trifluoromethyl)pyridin-4-yl]pyridin-3-yl}methyl)-5-(pyrazin-2-yl)pyridine-2-carboxamide;
N-{[6-(2-methylpyridin-4-yl)pyridin-3-yl]methyl}-6-phenoxypyridine-3-carboxamide;
5-(3-fluorophenyl)-N-({5-methyl-6-[2-(trifluoromethyl)pyridin-4-yl]pyridin-3-yl}methyl)pyridine-2-carboxamide;
N-({5-methyl-6-[2-(trifluoromethyl)pyridin-4-yl]pyridin-3-yl}methyl)-4-(pyrazin-2-yl)benzamide;
N-{[5-fluoro-6-(2-methylpyridin-4-yl)pyridin-3-yl]methyl}-5-(3-fluorophenyl)pyridine-2-carboxamide;
N-{[5-fluoro-6-(2-methylpyridin-4-yl)pyridin-3-yl]methyl}-5-(pyrazin-2-yl)pyridine-2-carboxamide;
N-{[5-fluoro-6-(2-methylpyridin-4-yl)pyridin-3-yl]methyl}-6-(pyrazin-2-yl)pyridine-3-carboxamide;
5-(4-acetylpiperazin-1-yl)-N-{[5-fluoro-6-(2-methylpyridin-4-yl)pyridin-3-yl]methyl}pyridine-2-carboxamide;
N-{[5-methyl-6-(2-methylpyridin-4-yl)pyridin-3-yl]methyl}-5-(pyrazin-2-yl)pyridine-2-carboxamide;
5-(3-fluoro-2-methylphenyl)-N-({6-[2-(trifluoromethyl)pyridin-4-yl]pyridin-3-yl}methyl)pyridine-2-carboxamide;
5-(5-fluoro-2-methylphenyl)-N-({6-[2-(trifluoromethyl)pyridin-4-yl]pyridin-3-yl}methyl)pyridine-2-carboxamide;
N-{[5-methyl-6-(2-oxo-1,2-dihydropyridin-4-yl)pyridin-3-yl]methyl}-5-(pyrazin-2-yl)pyridine-2-carboxamide;
5-(2-methylpyridin-3-yl)-N-({6-[2-(trifluoromethyl)pyridin-4-yl]pyridin-3-yl}methyl)pyridine-2-carboxamide;
N-((6-(1,1-dioxidothiomorpholino)pyridin-3-yl)methyl)-5-(pyrazin-2-yl)picolinamide;
N-((6-(1,1-dioxidothiomorpholino)pyridin-3-yl)methyl)-6-(pyrazin-2-yl)nicotinamide;
3-methyl-N-({5-methyl-6-[2-(trifluoromethyl)pyridin-4-yl]pyridin-3-yl}methyl)-4-(3-methylpyridin-2-yl)benzamide;
N-{[5-fluoro-6-(pyridazin-4-yl)pyridin-3-yl]methyl}-5-(pyrazin-2-yl)pyridine-2-carboxamide;
5-[6-(2-oxopyrrolidin-1-yl)pyridin-3-yl]-N-({6-[2-(trifluoromethyl)pyridin-4-yl]pyridin-3-yl}methyl)pyridine-2-carboxamide;
5-(3-methylpyridin-2-yl)-N-({6-[2-(trifluoromethyl)pyridin-4-yl]pyridin-3-yl}methyl)pyridine-2-carboxamide;
N-({5-methyl-6-[2-(trifluoromethyl)pyridin-4-yl]pyridin-3-yl}methyl)-5-(3-methylpyridin-2-yl)pyridine-2-carboxamide;
N-{[5-fluoro-6-(2-methylpyridin-4-yl)pyridin-3-yl]methyl}-5-(3-methylpyridin-2-yl)pyridine-2-carboxamide;
5-(5-fluoro-2-methylphenyl)-N-{[5-fluoro-6-(2-methylpyridin-4-yl)pyridin-3-yl]methyl}pyridine-2-carboxamide;
5-(5-fluoro-2-methylphenyl)-N-({5-methyl-6-[2-(trifluoromethyl)pyridin-4-yl]pyridin-3-yl}methyl)pyridine-2-carboxamide;
3-methyl-N-({5-methyl-6-[2-(trifluoromethyl)pyridin-4-yl]pyridin-3-yl}methyl)-4-(pyrazin-2-yl)benzamide;
4-methyl-N-({5-methyl-6-[2-(trifluoromethyl)pyridin-4-yl]pyridin-3-yl}methyl)-5-(pyrazin-2-yl)pyridine-2-carboxamide;
5-(5-fluoro-2-methylphenyl)-N-{[5-methyl-6-(2-methylpyridin-4-yl)pyridin-3-yl]methyl}pyridine-2-carboxamide;
N-{[3-methyl-5-(2-methylpyridin-4-yl)pyridin-2-yl]methyl}-5-(pyrazin-2-yl)pyridine-2-carboxamide;
5-(5-fluoro-2-methylphenyl)-4-methyl-N-({5-methyl-6-[2-(trifluoromethyl)pyridin-4-yl]pyridin-3-yl}methyl)pyridine-2-carboxamide;
5-(3-fluorophenyl)-4-methyl-N-({5-methyl-6-[2-(trifluoromethyl)pyridin-4-yl]pyridin-3-yl}methyl)pyridine-2-carboxamide;
5-(4-acetylpiperazin-1-yl)-N-({5-fluoro-6-[2-(trifluoromethyl)pyridin-4-yl]pyridin-3-yl}methyl)pyridine-2-carboxamide;
N-({5-fluoro-6-[2-(trifluoromethyl)pyridin-4-yl]pyridin-3-yl}methyl)-5-(pyrazin-2-yl)pyridine-2-carboxamide;
N-{[4-methyl-5-(2-methylpyridin-4-yl)pyridin-2-yl]methyl}-5-(pyrazin-2-yl)pyridine-2-carboxamide;
3-methyl-5-(pyrazin-2-yl)-N-({6-[2-(trifluoromethyl)pyridin-4-yl]pyridin-3-yl}methyl)pyridine-2-carboxamide;

1-(3-fluorophenyl)-N-{[5-methyl-6-(2-methylpyridin-4-yl) pyridin-3-yl]methyl}-2-oxo-1,2-dihydropyridine-4-carboxamide;

1-(3-fluorophenyl)-N-{[6-(2-methylpyridin-4-yl)pyridin-3-yl]methyl}-2-oxo-1,2-dihydropyridine-4-carboxamide;

1-(3-fluorophenyl)-N-({5-methyl-6-[2-(trifluoromethyl)pyridin-4-yl]pyridin-3-yl}methyl)-2-oxo-1,2-dihydropyridine-4-carboxamide;

5-(3-fluorophenyl)-N-{[1-(2-methylpyridin-4-yl)-2-oxo-1,2-dihydropyridin-4-yl]methyl}pyridine-2-carboxamide;

N-({2-oxo-1-[2-(trifluoromethyl)pyridin-4-yl]-1,2-dihydropyridin-4-yl}methyl)-5-(pyrazin-2-yl)pyridine-2-carboxamide;

methyl 4-{6-[({5-fluoro-6-[2-(trifluoromethyl)pyridin-4-yl]pyridin-3-yl}methyl)carbamoyl]pyridin-3-yl}piperazine-1-carboxylate;

6-(4-acetylpiperazin-1-yl)-N-({5-fluoro-6-[2-(trifluoromethyl)pyridin-4-yl]pyridin-3-yl}methyl)pyridine-3-carboxamide;

methyl 4-{5-[({5-fluoro-6-[2-(trifluoromethyl)pyridin-4-yl]pyridin-3-yl}methyl)carbamoyl]pyridin-2-yl}piperazine-1-carboxylate;

6-(3-fluorophenyl)-N-({1-[(2-fluoropyridin-4-yl)carbonyl]azetidin-3-yl}methyl)pyridine-3-carboxamide;

N-((2',3-dimethyl-[2,4'-bipyridin]-5-yl)methyl)-5-(pyrazin-2-yl)picolinamide fumarate; or a pharmaceutically acceptable salt thereof.

In one embodiment, the present invention provides a compound selected from:

1

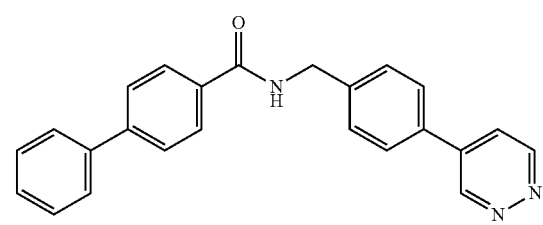

2

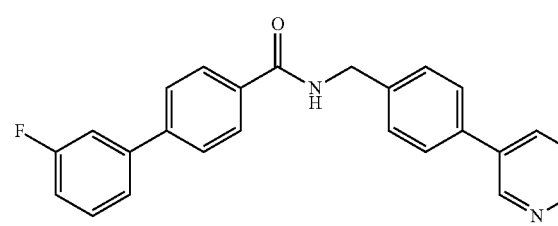

9

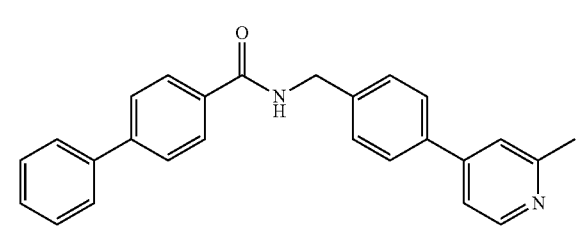

-continued

12

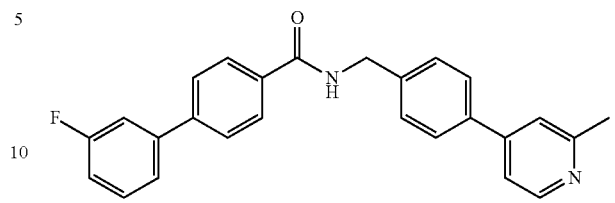

13

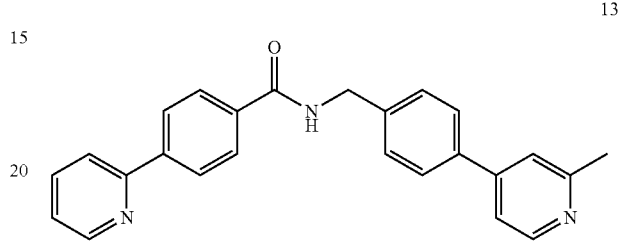

15

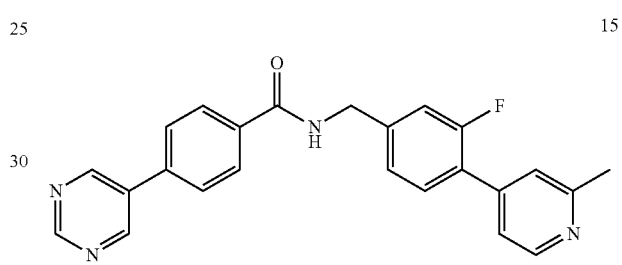

16

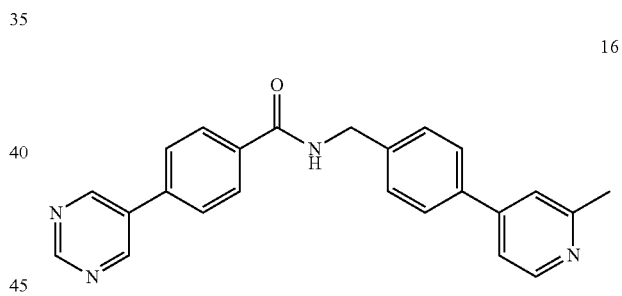

17

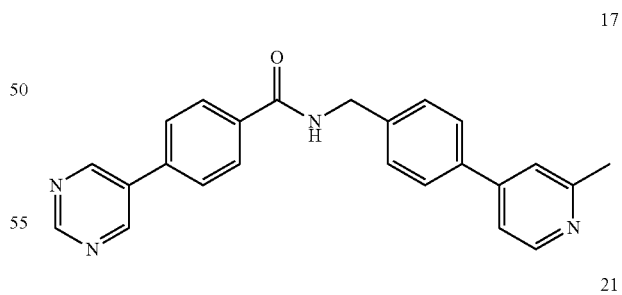

21

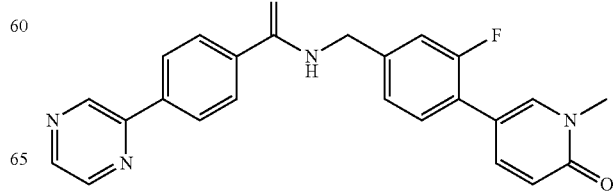

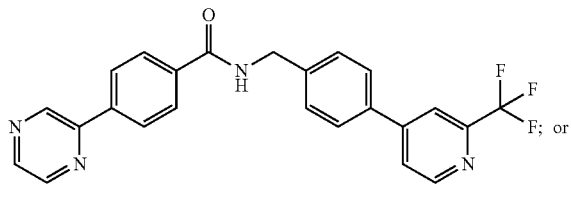
a pharmaceutical acceptable salt thereof.
In another embodiment, the present invention provides a compound selected from:
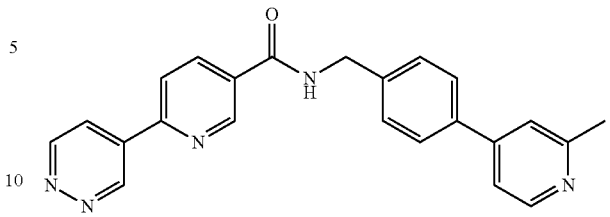
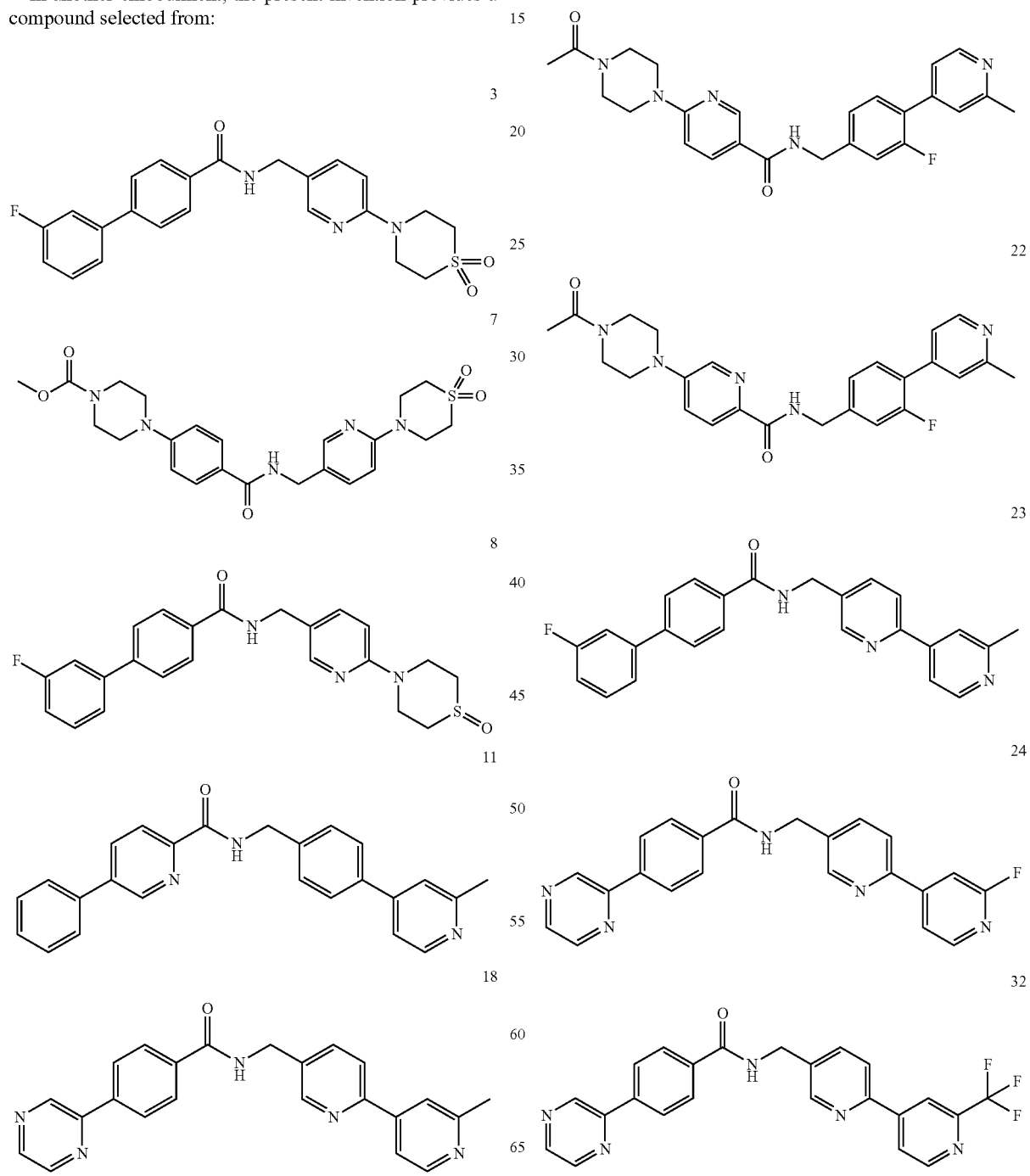

-continued
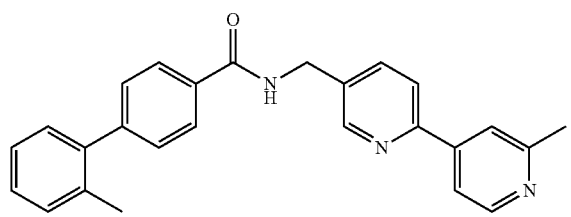
45
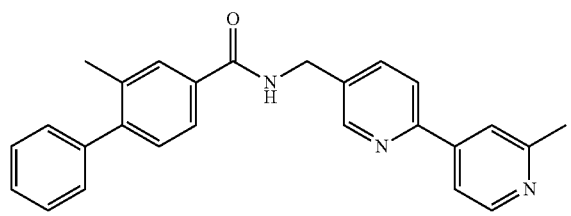
58
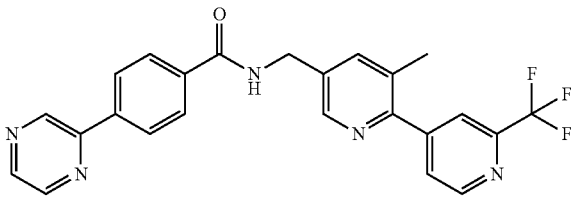
70
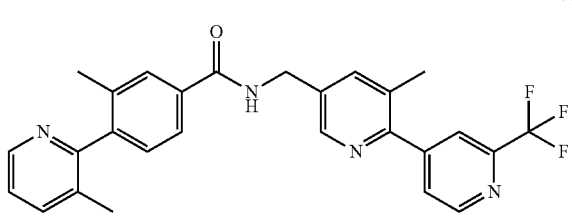
78
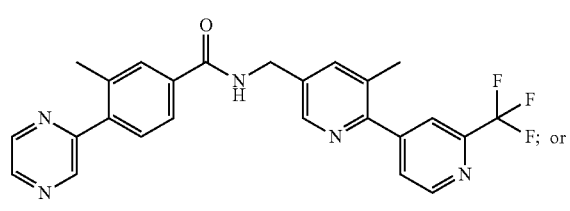
; or
a pharmaceutically acceptable salt thereof.
In yet another embodiment, the invention provides a compound selected from:
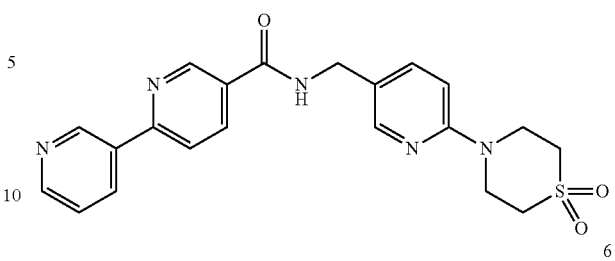
5
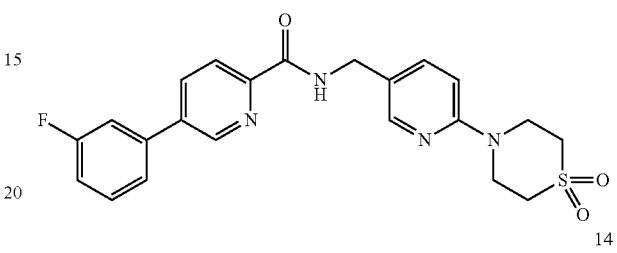
6
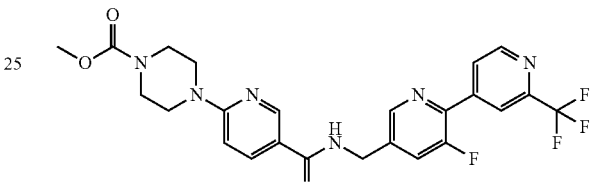
14
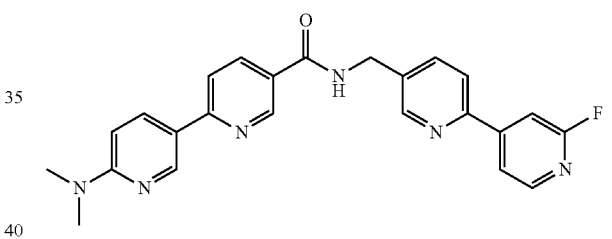
25
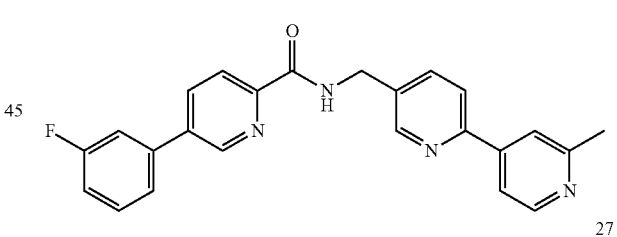
26
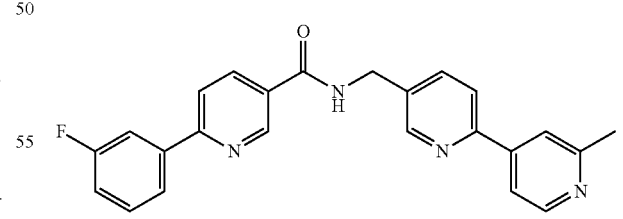
27
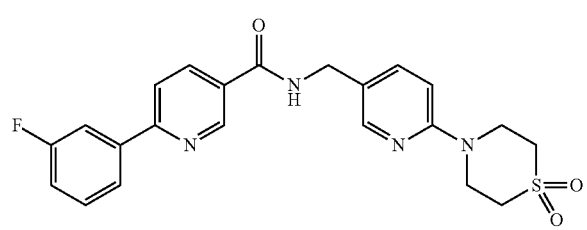
4
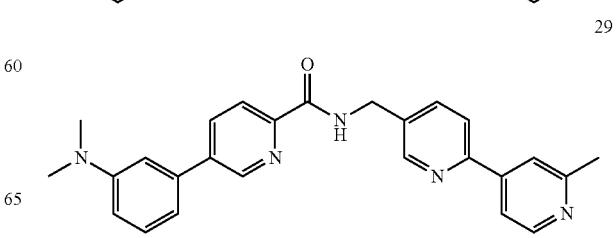
29

-continued
30
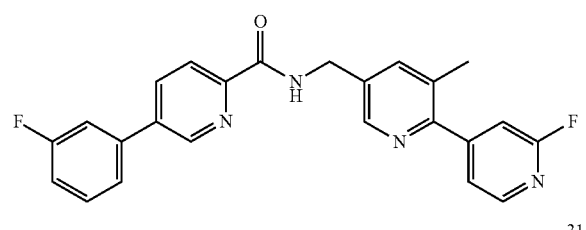
31
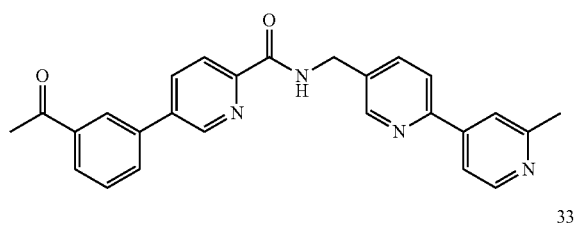
33
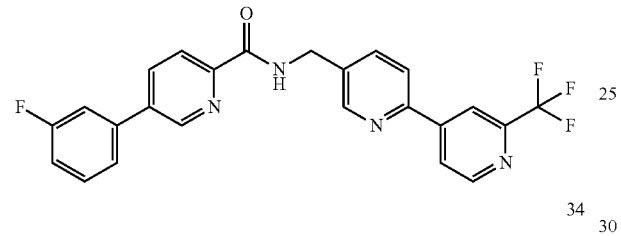
34
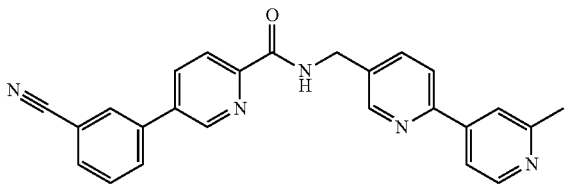
35
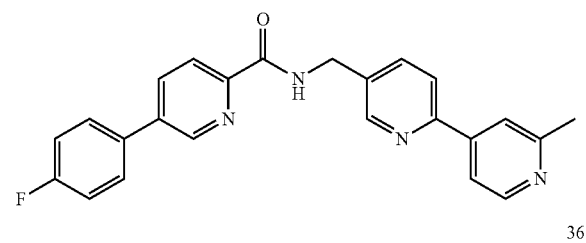
36
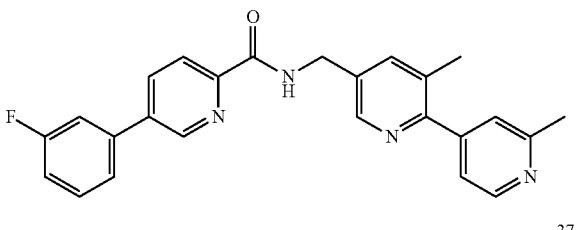
37
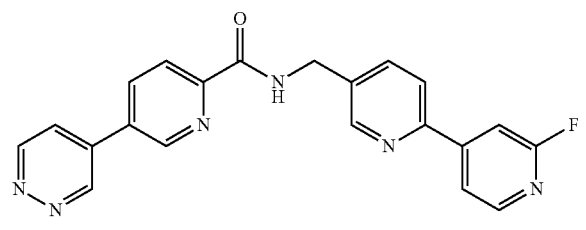
-continued
38
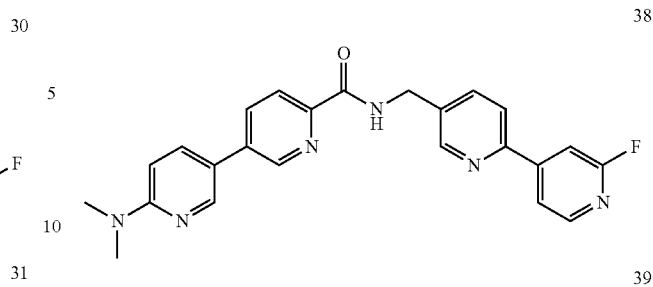
39
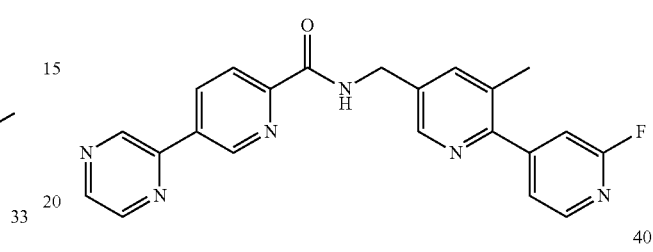
40
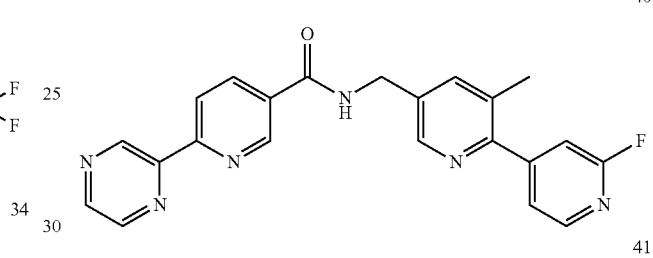
41
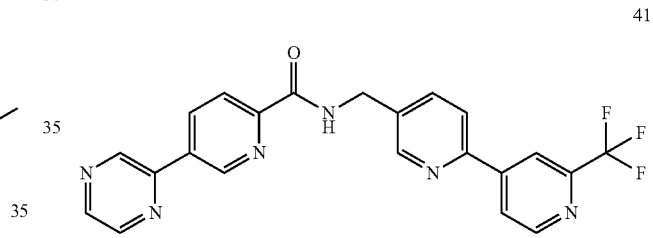
42
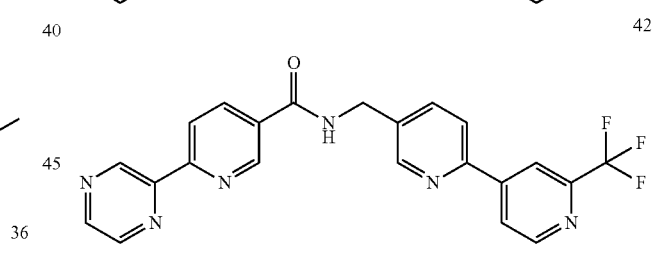
43
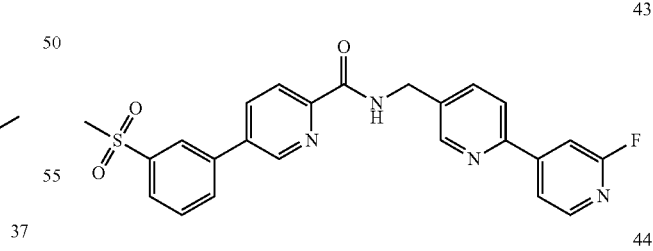
44
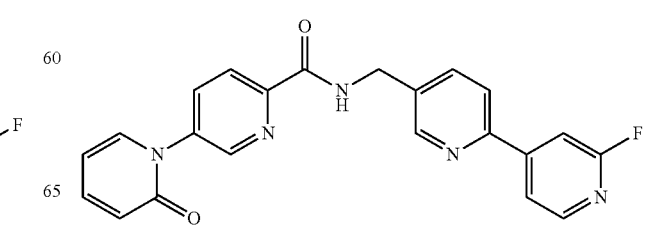

46
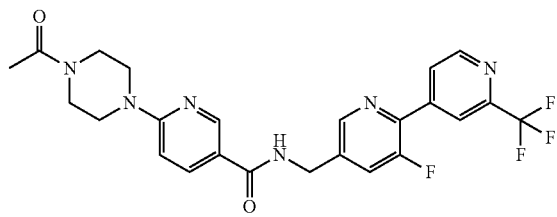
47
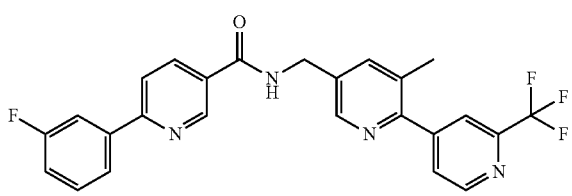
48
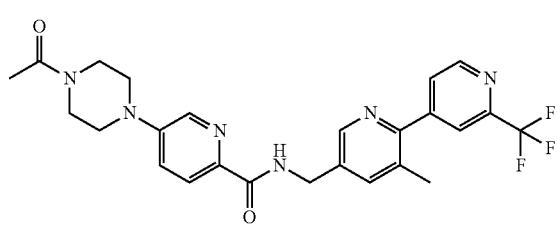
49
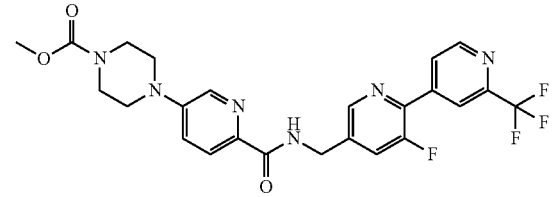
51
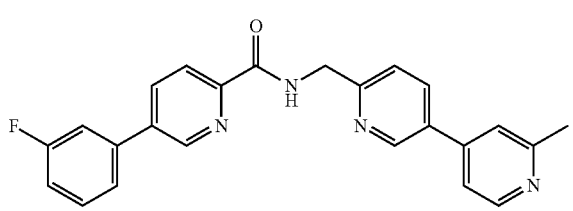
52
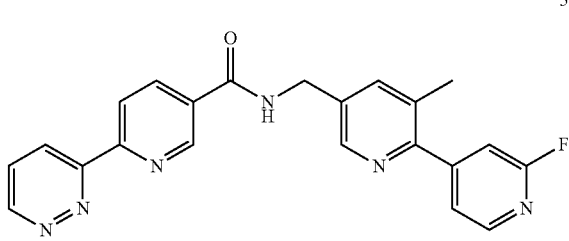
53
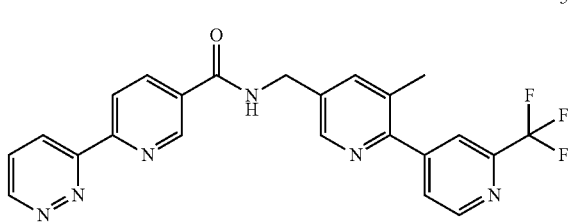
54
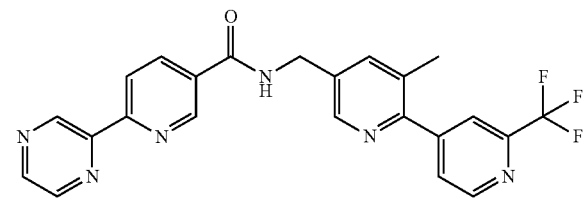
55
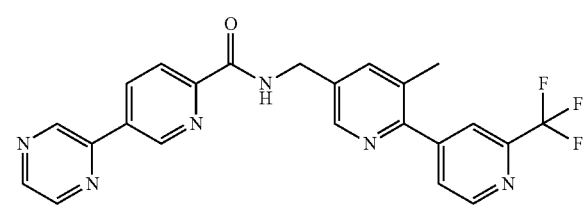
57
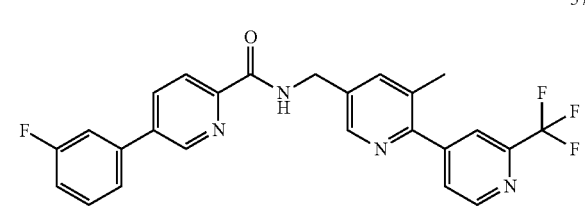
59
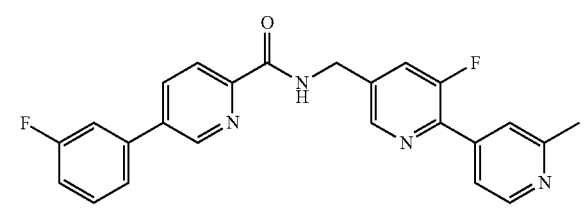
60
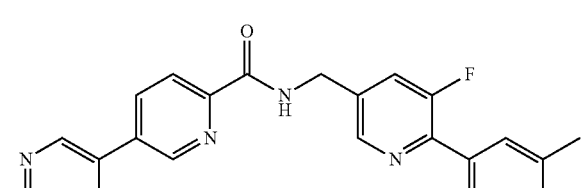
61
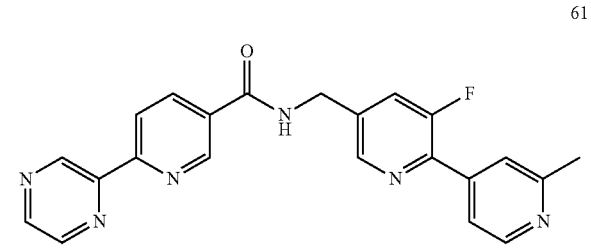
62
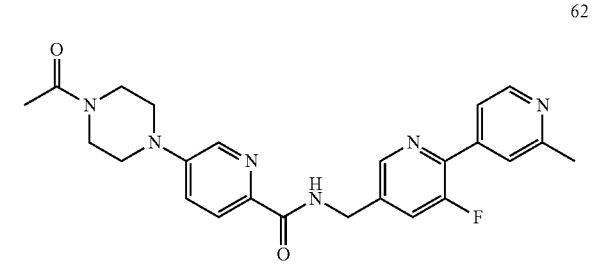

63
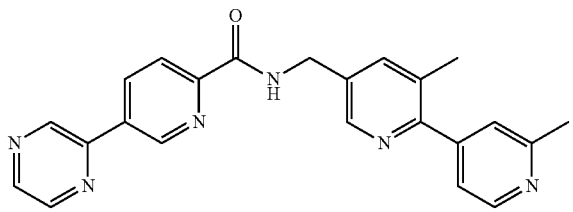
64
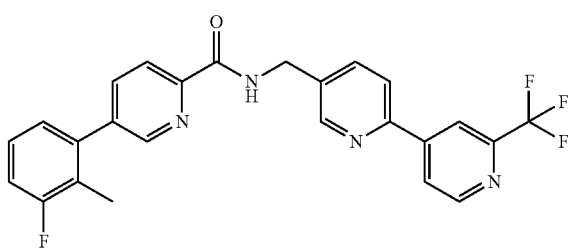
65
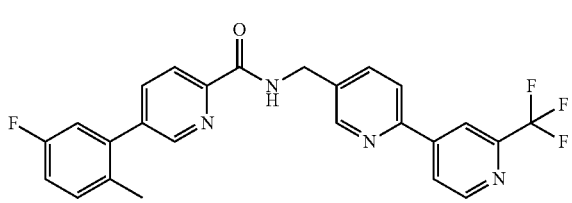
66
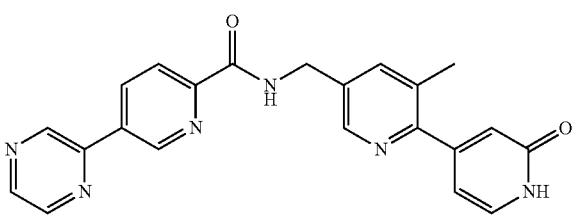
67
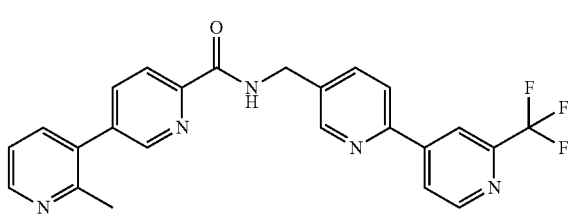
68
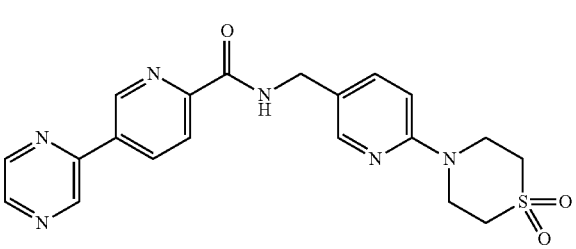
69
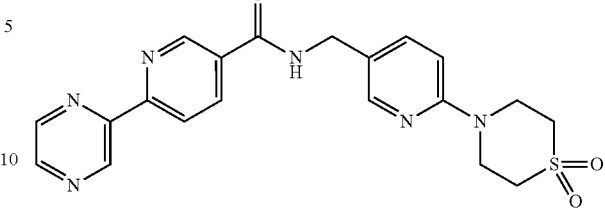
71
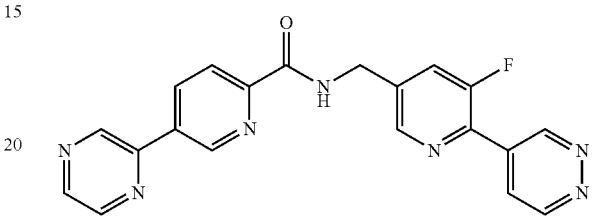
72
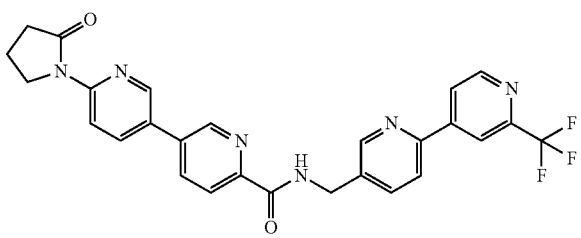
73
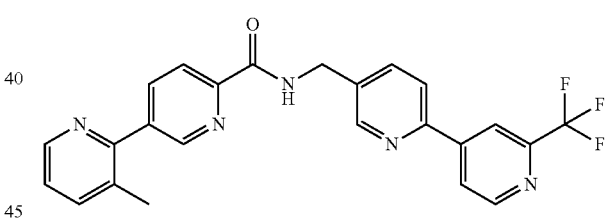
74
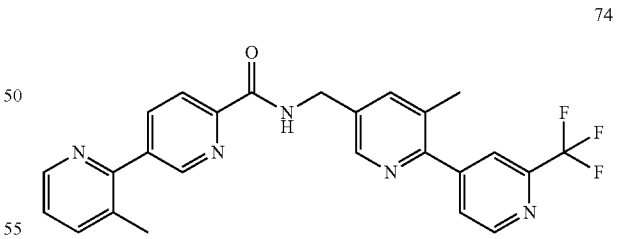
75
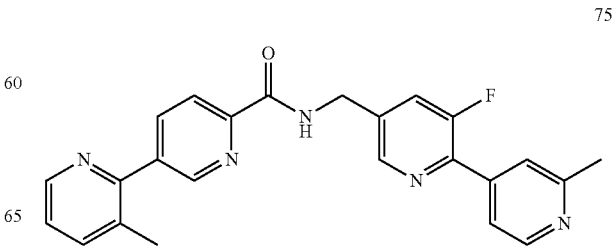

76
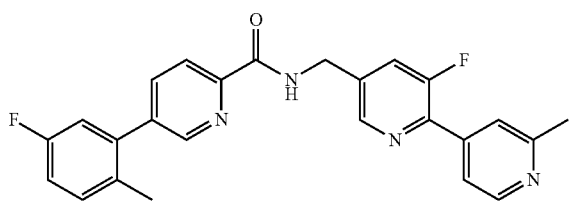
77
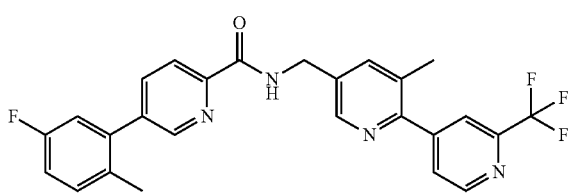
79
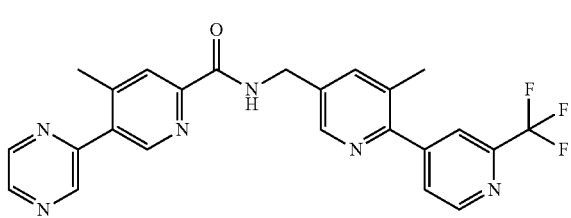
80
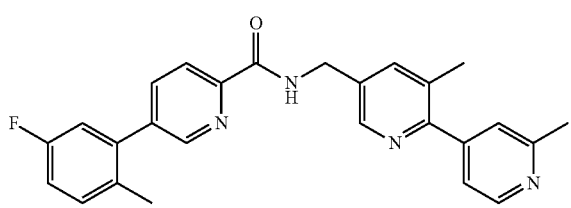
81
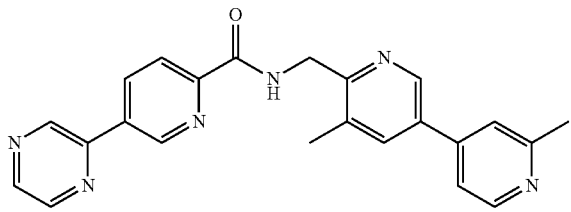
82
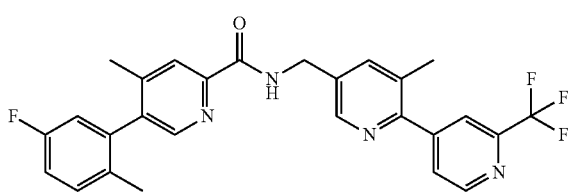
83
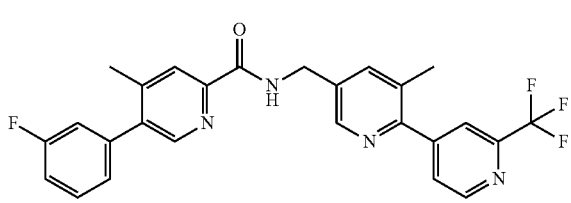
84
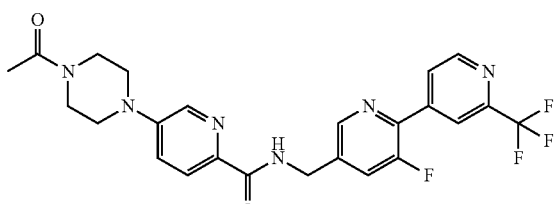
85
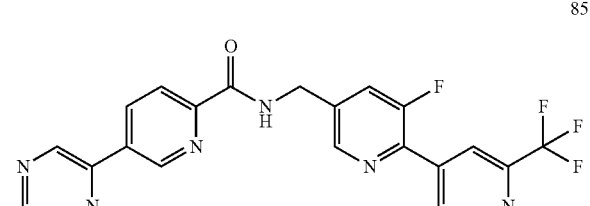
86
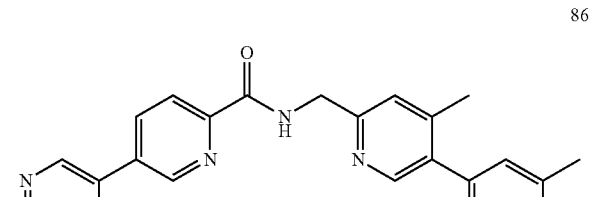
87
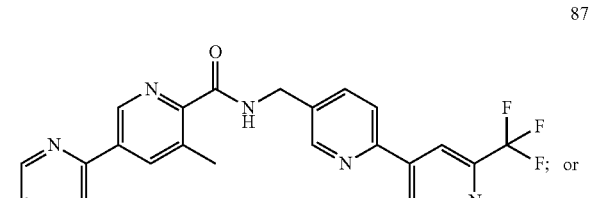
or
a pharmaceutically acceptable salt thereof.
In yet another embodiment, the present invention provides a compound selected from:
10
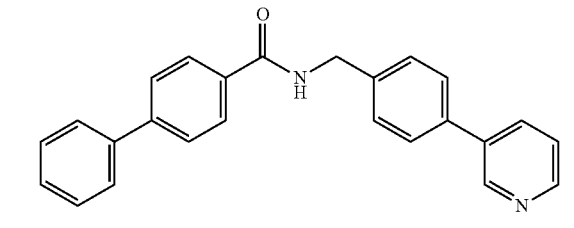
56
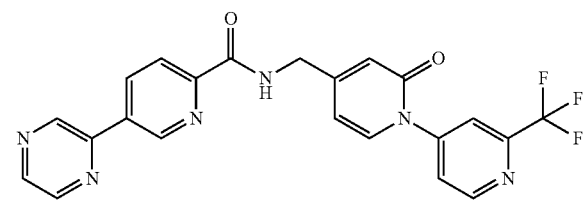

88

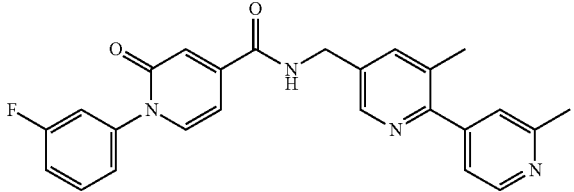

89

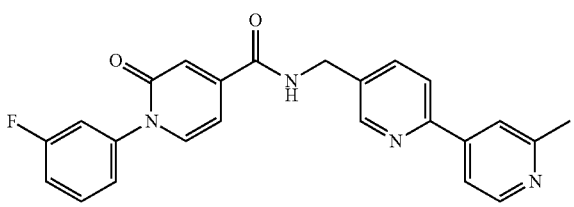

90

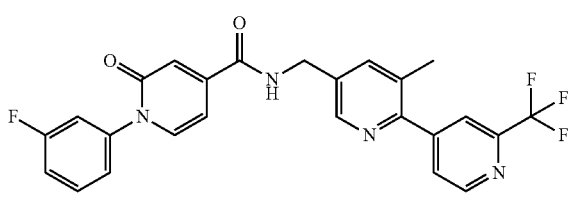

91

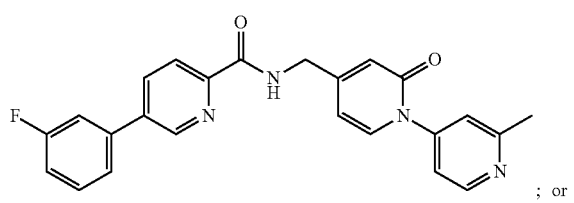

; or a pharmaceutical acceptable salt thereof.

In another aspect, the present invention provides pharmaceutical compositions comprising a compound having Formula (1), (2), (2A), and (3), and a pharmaceutically acceptable carrier.

In yet another aspect, the invention provides methods for inhibiting Wnt signaling in a cell, comprising contacting the cell with an effective amount of a compound having Formula (1), (2), (2A), and (3), or a pharmaceutical composition thereof.

In yet another aspect, the invention provides methods for inhibiting a Porcupine gene in a cell, comprising contacting the cell with an effective amount of a compound having Formula (1), (2), (2A), and (3), or a pharmaceutical composition thereof.

The invention also provides methods to treat, ameliorate or prevent a Wnt-mediated disorder in a subject suffering therefrom, comprising administering to the subject a therapeutically effective amount of a compound having Formula (1), (2), (2A), and (3), or a pharmaceutical composition thereof, and optionally in combination with a second therapeutic agent. Alternatively, the present invention provides for the use of a compound having Formula (1), (2), (2A), and (3), and optionally in combination with a second therapeutic agent, in the manufacture of a medicament for treating a Wnt-mediated disorder.

The compounds of the invention may be administered, for example, to a subject suffering from a Wnt-mediated disorder selected from keloids, fibrosis such as skin fibrosis, idiopathic pulmonary fibrosis, renal interstitial fibrosis and liver fibrosis; proteinuria, kidney graft rejection, osteoarthritis, Parkinson's disease, cystoid macular edema (CME) such as uveitis-associated CME; retinopathy such as diabetic retinopathy or retinopathy of prematurity; macular degeneration and a cell proliferative disorder associated with aberrant Wnt signaling activity.

In particular examples, the compounds of the invention may be used alone or in combination with a chemotherapeutic agent to treat a cell proliferative disorder, including but not limited to, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomysarcoma, brain tumor, Wilm's tumor, basal cell carcinoma, melanoma, head and neck cancer, cervical cancer and prostate cancer.

DEFINITIONS

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl", "heterocyclo" or "heterocyclic" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Additionally, one or two carbon atoms in the heterocyclyl ring can optionally be replaced by a —C(O)— group, such as for example, 2-oxo-pyrrolidinyl, 2-oxo-pyridyl, pyridonyl, 2-oxo-piperidinyl, and the like. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(O) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl.

Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(O) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-lngold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by Wnt, or (ii) associated with Wnt activity, or (iii) characterized by activity (normal or abnormal) of Wnt; or (2) reducing or inhibiting the activity of Wnt; or (3) reducing or inhibiting the expression of Wnt. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Wnt; or at least partially reducing or inhibiting the expression of Wnt.

As used herein, the term "subject" refers to an animal or a human. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

A "Wnt protein" is a ligand of the Wnt signaling pathway component which binds to a Frizzled receptor so as to activate Wnt signaling. Specific examples of Wnt proteins include at least 19 members, including: Wnt-1 (RefSeq.: NM-005430), Wnt-2 (RefSeq.: NM-003391), Wnt-2B (Wnt-13) (RefSeq.: NM-004185), Wnt-3 (ReSeq.: NM-030753), Wnt3a (RefSeq.: NM-033131), Wnt-4 (RefSeq.: NM-030761), Wnt-5A (RefSeq.: NM-003392), Wnt-5B (RefSeq.: NM-032642), Wnt-6 (RefSeq.: NM-006522), Wnt-7A (RefSeq.: NM-004625), Wnt-7B (RefSeq.: NM-058238), Wnt-8A (RefSeq.: NM-058244), Wnt-8B (RefSeq.: NM-003393), Wnt-9A (Wnt-14) (RefSeq.: NM-003395), Wnt-9B (Wnt-15) (RefSeq.: NM-003396), Wnt-10A (RefSeq.: NM-025216), Wnt-10B (RefSeq.: NM-003394), Wnt-11 (RefSeq.: NM-004626), Wnt-16 (RefSeq.: NM-016087)). While each member has varying degrees of sequence identity, each contain 23-24 conserved cysteine residues which show highly conserved spacing. McMahon, A P et al, Trends Genet. 8: 236-242 (1992); Miller J R., Genome Biol. 3(1): 3001.1-3001.15 (2002). For purposes of this invention, a Wnt protein and active variants thereof is a protein that binds to a Frizzled ECD or the CRD component of such an Frz ECD.

A "Wnt-mediated disorder" is a disorder, condition, or disease state characterized by aberrant Wnt signaling. In a specific aspect, the aberrant Wnt signaling is a level of Wnt signaling in a cell or tissue suspected of being diseased that exceeds the level of Wnt signaling in a similar non-diseased cell or tissue. In a specific aspect, a Wnt-mediated disorder includes cancer.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid.

As used herein, the term "a," "an," "the" and similar terms used in the context of the present invention (especially in the context of the claims) are to be construed to cover both the singular and plural unless otherwise indicated herein or clearly contradicted by the context.

The chemical naming protocol and structure diagrams used herein employ and rely on the chemical naming features as utilized by the ChemDraw program (available from CambridgeSoft Corp., Cambridge, Mass.). In particular, compound structures and names were derived using Chemdraw Ultra (Version 10.0) and/or ChemAxon Name Generator (JChem Version 5.3.1.0).

MODES OF CARRYING OUT THE INVENTION

The present invention relates to compositions and methods for modulating the Wnt signaling pathway. Various embodiments of the invention are described herein. It will be recognized that features specified in each embodiment may be combined with other specified features to provide further embodiments.

In one aspect, the present invention provides a compound having Formula (1):

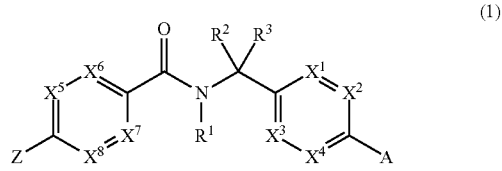

or a pharmaceutically acceptable salt thereof, wherein:
A is

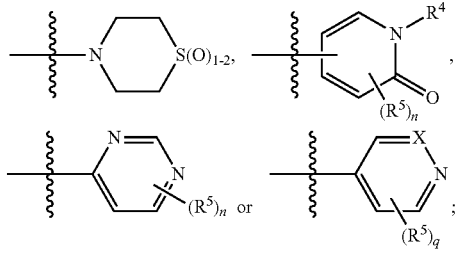

X is N, CH or $CR^6$;
$X^1$, $X^2$, $X^3$ and $X^4$ are independently N or $CR^{11}$;
$X^5$, $X^6$, $X^7$ and $X^8$ are independently N or $CR^{12}$;
Z is optionally substituted with 1-2 $R^7$ groups and is aryl, 5-6 membered heterocyclic ring, or a 5-6 membered heteroaryl; wherein said heterocyclic ring and heteroaryl independently contain 1-2 heteroatoms selected from N, O and S;
$R^1$, $R^2$, $R^3$ and $R^4$ are hydrogen or $C_{1-6}$ alkyl;
$R^5$ and $R^6$ are independently halo, cyano, $C_{1-6}$alkoxy, $S(O)_2 R^{10}$, or a $C_{1-6}$ alkyl optionally substituted with halo;
$R^7$ is hydrogen, halo, cyano, $C_{1-6}$alkoxy, $C_{1-6}$ alkyl, $C_{2-6}$ alkenyl or $C_{2-6}$ alkynyl, each of which can be optionally substituted with halo, amino, hydroxyl, alkoxy or cyano; -L-W, $NR^8R^9$, -L-C(O)$R^{10}$, -L-C(O)O$R^{10}$, -L-C(O)N$R^8R^9$, O$R^9$; -L-S(O)$_2R^{10}$ or -L-S(O)$_2NR^8R^9$;
$R^8$ and $R^9$ are independently hydrogen, -L-W, or $C_{1-6}$ alkyl, $C_{2-6}$ alkenyl or $C_{2-6}$ alkynyl, each of which may be optionally substituted with halo, amino, hydroxyl, alkoxy or cyano; alternatively, $R^8$ and $R^9$ together with the atoms to which they are attached may form a ring;

$R^{10}$ is $C_{1-6}$ alkyl or -L-W;

$R^{11}$ and $R^{12}$ are independently hydrogen, halo, cyano, $C_{1-6}$alkoxy, or a $C_{1-6}$ alkyl optionally substituted with halo; and L is a bond or $(CR_2)_{1-4}$ wherein R is H or $C_{1-6}$ alkyl;

W is $C_{3-7}$cycloalkyl, aryl, 5-6 membered heterocyclic ring, or 5-6 membered heteroaryl; wherein said heterocyclic ring and heteroaryl independently contain 1-3 heteroatoms selected from N, O and S; and n and q are independently 0-3.

The present invention also provides a compound of Formula (2):

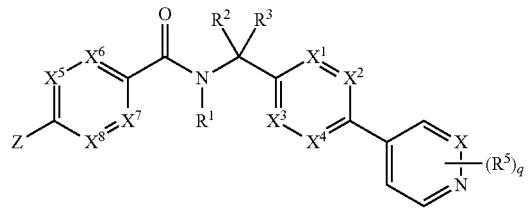

(2)

or a pharmaceutically acceptable salt thereof, wherein:

Z is optionally substituted with 1-2 $R^7$ groups and is aryl or a 5-6 membered heteroaryl containing 1-2 nitrogen heteroatoms;

X is N, CH or $CR^6$;

$X^1$, $X^2$, $X^3$ and $X^4$ are independently N or $CR^{11}$;

$X^5$, $X^6$, $X^7$ and $X^8$ are independently N or $CR^{12}$;

$R^1$, $R^2$ and $R^3$ are hydrogen;

$R^5$ and $R^6$ are independently halo, or a $C_{1-6}$ alkyl optionally substituted with halo;

$R^7$ is halo, cyano, $C_{1-6}$ alkyl, $NR^8R^9$, -L-C(O)$R^{10}$, -L-C(O)O$R^{10}$ or -L-S(O)$_2R^{10}$ wherein L is a bond;

$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;

$R^{10}$ is $C_{1-6}$ alkyl;

$R^{11}$ and $R^{12}$ are independently hydrogen, halo or $C_{1-6}$ alkyl; and n and q are 0-1.

Furthermore, the present invention provides a compound of Formula (2A):

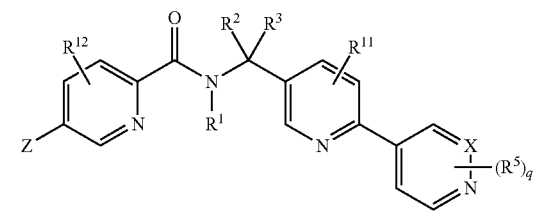

(2A)

or a pharmaceutically acceptable salt thereof, wherein:

X is N, CH or $CR^6$;

Z is optionally substituted with 1-2 $R^7$ groups and is aryl or a 5-6 membered heteroaryl containing 1-2 nitrogen heteroatoms;

$R^1$, $R^2$ and $R^3$ are hydrogen;

$R^5$ and $R^6$ are independently halo, or a $C_{1-6}$ alkyl optionally substituted with halo;

q is 0;

$R^7$ is halo, cyano, $C_{1-6}$ alkyl, $NR^8R^9$, -L-C(O)$R^{10}$, -L-C(O)O$R^{10}$ or -L-S(O)$_2R^{10}$ wherein L is a bond;

$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;

$R^{10}$ is $C_{1-6}$ alkyl;

$R^{11}$ is hydrogen, halo or methyl; and $R^{12}$ is hydrogen or methyl.

Also described herein are compound of Formula (3):

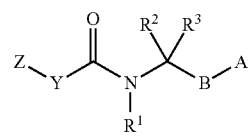

(3)

or a pharmaceutically acceptable salt thereof, wherein:

wherein A is

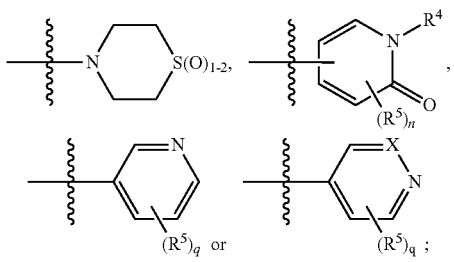

X is N, CH or $CR^6$;

B and Y are independently phenyl, or a 6-membered heteroaryl ring comprising 1-2 nitrogen heteroatoms, wherein said phenyl is unsubstituted or substituted by $R^{7a}$ and said 6-membered heteroaryl is unsubstituted or substituted by $R^{7b}$; or one of B and Y is pyridyl unsubstituted or substituted by $C_{1-6}$ alkyl, and the other is

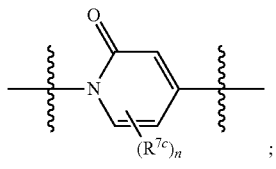

Z is optionally substituted with 1-2 $R^{7d}$ groups and is aryl, a 5-6 membered heterocyclic ring, or a 5-6 membered heteroaryl; wherein said heterocyclic ring and heteroaryl independently comprise 1-2 heteroatoms selected from N, O and S;

$R^1$, $R^2$ and $R^3$ are hydrogen;

$R^4$ is hydrogen or $C_{1-6}$ alkyl;

$R^5$, $R^6$ and $R^{7c}$ are independently halo, or a $C_{1-6}$ alkyl optionally substituted with halo;

$R^{7a}$ and $R^{7b}$ are independently halo or $C_{1-6}$ alkyl;

$R^{7d}$ is halo, cyano, $C_{1-6}$ alkyl, $NR^8R^9$, -L-C(O)$R^{10}$, -L-C(O)O$R^{10}$ or -L-S(O)$_2R^{10}$ wherein L is a bond;

$R^8$ and $R^9$ are independently hydrogen or $C_{1-6}$ alkyl; alternatively, $R^8$ and $R^9$ together with nitrogen in $NR^8R^9$ form a 5-6 membered heterocyclyl;

$R^{10}$ is $C_{1-6}$ alkyl; and
n and q are 0-1.

In a further embodiment, the present invention provides a compound of Formula (3'):

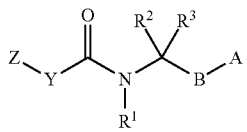
(3')

or a pharmaceutically acceptable salt thereof, wherein:
A is

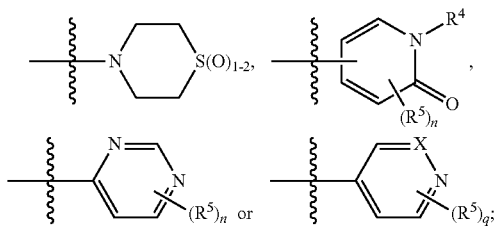

X is N, CH or $CR^6$;
B and Y are optionally substituted with 1-2 $R^6$ groups and are independently

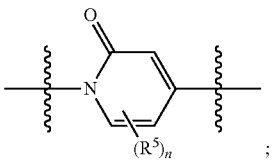

a 6-membered aryl or a 6-membered heteroaryl ring having 1-2 nitrogen heteroatoms selected from N, O and S;
Z is optionally substituted with 1-2 $R^7$ groups and is aryl, 5-6 membered heterocyclic ring, or a 5-6 membered heteroaryl; wherein said heterocyclic ring and heteroaryl independently contain 1-2 heteroatoms selected from N, O and S;
$R^1$, $R^2$, $R^3$ and $R^4$ are hydrogen or $C_{1-6}$ alkyl;
$R^5$ and $R^6$ are independently halo, cyano, $C_{1-6}$alkoxy, $S(O)_2 R^{10}$, or a $C_{1-6}$ alkyl optionally substituted with halo;
$R^7$ is hydrogen, halo, cyano, $C_{1-6}$alkoxy, $C_{1-6}$ alkyl, $C_{2-6}$ alkenyl or $C_{2-6}$ alkynyl, each of which can be optionally substituted with halo, amino, hydroxyl, alkoxy or cyano; -L-W, $NR^8R^9$, -L-C(O)$R^{10}$, -L-C(O)O$R^{10}$, -L-C(O)N$R^8R^9$, $OR^9$; -L-S(O)$_2R^{10}$ or -L-S(O)$_2NR^8R^9$;
$R^8$ and $R^9$ are independently hydrogen, -L-W, or $C_{1-6}$ alkyl, $C_{2-6}$ alkenyl or $C_{2-6}$ alkynyl, each of which may be optionally substituted with halo, amino, hydroxyl, alkoxy or cyano;
alternatively, $R^8$ and $R^9$ together with the atoms to which they are attached may form a ring;
$R^{10}$ is $C_{1-6}$ alkyl or -L-W;
L is a bond or $(CR_2)_{1-4}$ wherein R is H or $C_{1-6}$ alkyl;
W is $C_{3-7}$cycloalkyl, aryl, 5-6 membered heterocyclic ring, or 5-6 membered heteroaryl; wherein said heterocyclic ring and heteroaryl independently contain 1-3 heteroatoms selected from N, O and S; and
n and q are independently 0-3.

In a second further embodiment, the invention provides a compound having Formula (4):

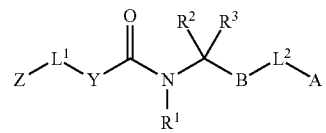
(4)

or a pharmaceutically acceptable salt thereof, wherein:
A is a 5-6 membered heterocyclic ring having 1-2 heteroatoms selected from N, O and S; or selected from the group

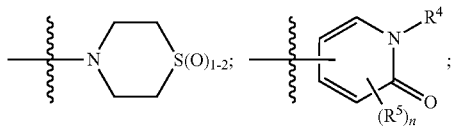

X is N, CH or $CR^6$;
B, Y and Z are optionally substituted with 1-3 $R^7$ groups and are independently aryl, heteroaryl or heterocyclyl; and if any heterocyclyl or heteroaryl contains an —NH— moiety, that nitrogen may be optionally substituted with -L-C(O)$R^{10}$ or -L-C(O)O$R^{10}$;
$R^1$ and $R^4$ are independently hydrogen or $C_{1-6}$ alkyl;
$R^2$ and $R^3$ are independently hydrogen, $C_{1-6}$ alkyl or halo;
$R^5$ and $R^6$ are independently halo, cyano, $C_{1-6}$alkoxy, or a $C_{1-6}$ alkyl optionally substituted with halo, alkoxy or amino;
$R^7$ is hydrogen, halo, $C_{1-6}$alkoxy, cyano, $C_{1-6}$ alkyl, $C_{2-6}$ alkenyl or $C_{2-6}$ alkynyl, each of which can be optionally substituted with halo, amino, hydroxyl, alkoxy or cyano; -L-W, $NR^8R^9$, -L-C(O)$R^{10}$, -L-C(O)O$R^{10}$, -L-C(O)N$R^8R^9$, $OR^9$; -L-S(O)$_2R^{10}$ or -L-S(O)$_2NR^8R^9$;
$R^8$ and $R^9$ are independently hydrogen, -L-W, or $C_{1-6}$ alkyl, $C_{2-6}$ alkenyl or $C_{2-6}$ alkynyl, each of which may be optionally substituted with halo, amino, hydroxyl, alkoxy or cyano; alternatively, $R^8$ and $R^9$ together with the atoms to which they are attached may form a ring;
$R^{10}$ is -L-W, or $C_{1-6}$ alkyl, $C_{2-6}$ alkenyl or $C_{2-6}$ alkynyl, each of which may be optionally substituted with halo, amino, hydroxyl, alkoxy or cyano;
L is a bond or $(CR_2)_{1-4}$ wherein R is H or $C_{1-6}$ alkyl;
$L^1$ and $L^2$ are independently a bond, C(O), O or S;
W is $C_{3-7}$cycloalkyl, aryl, heterocyclyl, or heteroaryl;
n and q are independently 0-3; and
p is 0-2.

In the above Formula (4), A can be selected from

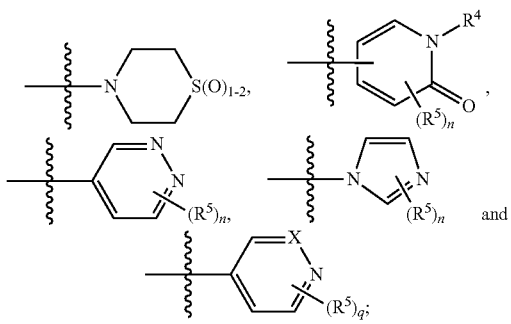

wherein X, $R^5$, n and q are as defined in Formula (4).
In the above Formula (4), B, Y and Z can independently be aryl, a 5-6 membered heterocyclic ring, or a 5-6 membered heteroaryl; wherein said heterocyclic ring and heteroaryl independently contain 1-2 heteroatoms selected from N, O and S. In some examples, B, Y and Z can independently be phenyl, pyridonyl, piperazinyl, piperidinyl, azetidinyl, pyridinyl, pyridazine, pyrazine, pyrimidine, pyrazole, thiazolyl, morpholinyl or 1,2,3,6-tetrahydropyridine, each of which is optionally substituted with 1-2 $R^7$ groups and $R^7$ is as defined in Formula (4). In some examples, $L^1$ and $L^2$ are a bond. In other examples, one of $L^1$ and $L^2$ is a bond, and the other is C(O), O or S.

In the above Formula (4), B can be phenyl, pyridyl, pyridonyl, pyrimidinyl, piperidyl, azetidinyl or piperazinyl, each of which is optionally substituted with halo, cyano or a $C_{1-6}$ alkyl optionally substituted with halo.

In the above Formula (3') or (4), Y and B can independently be

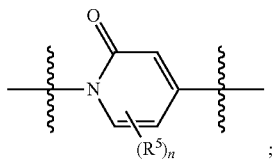

phenyl, pyridyl, piperidinyl, piperazinyl or azetidinyl; or more particularly, Y and B are independently phenyl, pyridyl or

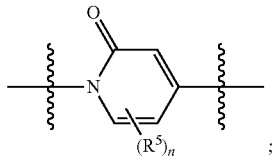

each of which is optionally substituted with 1-2 $R^6$ groups; and $R^5$, $R^6$ and n are as defined in Formula (3') or (4). In yet other examples, one of Y and B is phenyl and the other is pyridyl; wherein said phenyl and pyridyl are optionally substituted with $R^6$. In yet other examples, one of Y and B is pyridyl, and the other is

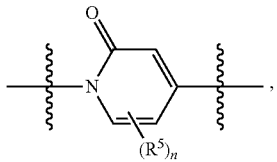

azetidinyl, piperidinyl or piperazinyl; wherein said pyridyl, azetidinyl, piperidinyl or piperazinyl are optionally substituted with 1-2 $R^6$ groups; and $R^5$, $R^6$ and n are as defined in Formula (3') or (4).

In the above Formula (1), (2), (2A), (3), (3') and (4), any aryl or heteroaryl may be optionally substituted with 1-5 substituents independently selected at each occurrence from the group consisting of hydroxyl, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, where each of the aforementioned hydrocarbon groups (e.g., alkyl, alkenyl, alkynyl, alkoxy residues) may be further substituted by one or more residues independently selected at each occurrence from halogen, hydroxyl or C1-C4-alkoxy groups.

Unless specified otherwise, the term "compounds of the present invention" refers to compounds of Formula (1), (2), (2A), (3), (3') and (4), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$ and $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula (1), (2), (2A), (3), (3') and (4) can generally be prepared by conventional techniques known to those skilled in the art or by processes analogous to those described in the accompanying Examples and Processes using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d^6$-acetone, $d^6$-DMSO.

Compounds of the invention, i.e. compounds of Formula (1), (2), (2A), (3) and (4) that contain groups capable of acting as donors and/or acceptors for hydrogen bonds may be capable of forming co-crystals with suitable co-crystal formers. These co-crystals may be prepared from compounds of Formula (1), (2), (2A), (3), (3') and (4) by known co-crystal forming procedures. Such procedures include grinding, heating, co-subliming, co-melting, or contacting in solution compounds of Formula (1), (2), (2A), (3), (3') and (4) with the co-crystal former under crystallization conditions and isolating co-crystals thereby formed. Suitable co-crystal formers include those described in WO 2004/078163. Hence the invention further provides co-crystals comprising a compound of Formula (1), (2), (2A), (3), (3') or (4).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention also provides for a method of inhibiting Wnt-signaling in a cell comprising contacting the cell with an effective amount of a Wnt antagonist. In one embodiment, the administered amount is a therapeutically effective amount and the inhibition of Wnt signaling further results in the inhibition of the growth of the cell. In a further embodiment, the cell is a cancer cell.

Inhibition of cell proliferation is measured using methods known to those skilled in the art. For example, a convenient assay for measuring cell proliferation is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160: 81-88, U.S. Pat. No. 6,602,677. The assay may be conducted in 96- or 384-well format, making it amenable to automated high-throughput screening (HTS). See Cree et al (1995) Anti-Cancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU). Inhibition of cell proliferation may also be measured using colony formation assays known in the art.

Furthermore, the invention provides for methods of treating a Wnt-mediated disorder in a subject suffering therefrom, comprising administering to the subject a therapeutically effective amount of a Wnt antagonist. In one embodiment, the disorder is a cell proliferative disorder associated with aberrant, e.g., increased, expression of activity of Wnt signaling. In another embodiment, the disorder results from increased expression of a Wnt protein. In yet another embodiment, the cell proliferative disorder is cancer, such as for example, colon cancer, colorectal cancer, breast cancer, cancer associated with various disorders relating to HSC's, such as leukemias and various other blood related cancers, and cancer related to neuronal proliferative disorders, including brain tumors, such as gliomas, astrocytomas, meningiomas, Schwannomas, pituitary tumors, primitive neuroectodermal tumors (PNET), medulloblastomas, craniopharyngioma, pineal region tumors, and skin cancers, including basal cell carcinoma and squamous cell carcinoma.

Treatment of the cell proliferative disorder by administration of a Wnt antagonist results in an observable and/or measurable reduction in or absence of one or more of the following: reduction in the number of cancer cells or absence of the cancer cells; reduction in the tumor size; inhibition of cancer cell infiltration into peripheral organs including the spread of cancer into soft tissue and bone; inhibition of tumor metastasis; inhibition, to some extent, of tumor growth; and/or relief to some extent, one or more of the symptoms associated with the specific cancer; reduced morbidity and mortality, and improvement in quality of life issues. To the extent the Wnt antagonist may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB). In a specific embodiment, the administration of Wnt antagonist decreases tumor burden (e.g., reduces size or severity of the cancer). In yet another specific embodiment, the administration of Wnt antagonist kills the cancer.

Pharmacology and Utility

The compounds of Formula (1), (2), (2A), (3), (3') and (4) in free form or in salt form, exhibit valuable pharmacological properties, e.g. Wnt modulating properties, e.g. as indicated in in vitro and/or in vivo tests as provided in the next sections, and are therefore indicated for therapy in treating a disorder which may be treated by modulating Wnt, such as those described below.

The current paradigm for developing therapies for Wnt signaling-related disorders relies on targeting β-cat or Wnt pathway components downstream of β-cat. Recent studies, however, suggest that inhibition of the extracellular ligand-receptor interaction component is effective in reducing the tumorigenicity, even though the event initiating the Wnt signaling may have occurred downstream. Moreover, the transfection of inoperative frizzled receptor (Frz7 ectodomain) into carcinoma cell line (SK-CO-1) restored a normal β-catenin phenotype. This cell line has active Wnt signaling due to a homozygous APC-/- mutation. Such cells also did not demonstrate tumor formation when transferred in vivo. Vincan et al., Differentiation 2005; 73: 142-153. This demonstrates that the inhibition of Wnt signaling at the extracellular level can downregulate Wnt signaling resulting from activation of a downstream intracellular Wnt signaling pathway component. This further suggests that inhibitors of the Wnt signaling pathway may be used in the treatment of a Wnt-mediated disorder, regardless of the particular manner in which Wnt signaling has been activated, and all forms of Wnt-mediated disorders, such as those described below, are potentially treatable with the compounds of the present invention.

Disorders Associated with Wnt Signaling Activity

Deregulation of the Wnt signaling pathway may be caused by somatic mutations in genes encoding various Wnt signaling pathway components. For example, aberrant Wnt signaling activity has been associated with Wnt ligand overexpression in non small cell lung cancer (NSCLC) [You et al., Oncogene 2004; 23: 6170-6174], chronic lymphocytic leukemia (CLL) [Lu et al., Proc. Natl. Acad. Sci. USA 2004; 101: 3118-3123], gastric cancer [Kim et al., Exp. Oncol. 2003; 25: 211-215; Saitoh et al., Int. J. Mol. Med. 2002; 9: 515-519], head and neck squamous cell carcinoma (HNSCC) [Rhee et al., Oncogene 2002; 21: 6598-6605], colorectal cancer [Holcombe et al., Mol. Pathol. 2002; 55: 220-226], ovarian cancer [Ricken et al., Endocrinology 2002; 143: 2741-2749], basal cell carcinoma (BCC) [Lo Muzio et al., Anticancer Res. 2002; 22: 565-576] and breast cancer. Moreover, the reduction of various Wnt ligand regulatory molecules such as sFRP and WIF-1 have been associated with breast cancer [Klopocki et al., Int. J. Oncol. 2004; 25: 641-649; Ugolini et al., Oncogene 2001; 20: 5810-5817; Wissmann et al., J. Pathol 2003; 201: 204-212], bladder cancer [Stoehr et al., Lab Invest. 2004; 84: 465-478; Wissmann et al., supra], mesothelioma [Lee et al., Oncogene 2004; 23: 6672-6676], colorectal cancer [Suzuki et al., Nature Genet. 2004; 36: 417-422; Kim et al., Mol. Cancer Ther. 2002; 1: 1355-1359; Caldwell et al., Cancer Res. 2004; 64: 883-888], prostate cancer [Wissman et al., supra], NSCLC [Mazieres et al., Cancer Res. 2004; 64: 4717-4720], and lung cancer [Wissman et al., supra].

Aberrant Wnt signaling resulting from overexpression of various components of the Frz-LRP receptor complex have also been associated with certain cancers. For example, LRP5 overexpression has been associated with osteosarcoma [Hoang et al., Int. J. Cancer 2004; 109: 106-111], while Frz overexpression has been associated with cancers such as prostate [Wissmann et al., supra], HNSCC [Rhee et al., Oncogene 2002; 21: 6598-6605], colorectal [Holcombe et al., supra], ovarian cancer [Wissman et al., supra], esophageal squamous cell carcinoma [Tanaka et al., Proc. Natl. Acad. Sci. USA 1998; 95: 10164-10169] and gastric [Kirikoshi et al., Int. J. Oncol. 2001; 19: 111-115]. Additionally, overexpression of Wnt signaling pathway components such as Dishevelled have been associated with cancers such as prostate [Wissman et al, supra], breast [Nagahata et al., Cancer Sci. 2003; 94: 515-518], mesothelioma [Uematsu et al., Cancer Res. 2003; 63: 4547-4551] and cervical [Okino et al, Oncol Rep. 2003; 10: 1219-1223]. Frat-1 overexpression has been associated with cancers such as pancreatic, esophageal, cervical, breast and gastric. [Saitoh et al., Int. J. Oncol. 2002; 20: 785-789; Saitoh et al., Int. J. Oncol 2001; 19: 311-315]. Axin loss of function (LOF) mutations have been associated with hepatocellular cancer [Satoh et al., Nature Genet. 2000; 24: 245-250; Taniguchi et al., Oncogene 2002; 21: 4863-4871] and medulloblastoma [Dahmen et al., Cancer Res. 2001; 61: 7039-7043; Yokota et al., Int. J. Cancer 2002; 101: 198-201].

Furthermore, a multitude of cancers has been associated with activating β-catenin through disruption of the "degradation complex" such as gain-of-function mutations in β-catenin or loss-of-function mutations in APC. A reduction in the degradation of β-catenin results in greater amounts of functional β-catenin in the cell, which then causes increased transcription of the target genes, resulting in aberrant cell proliferation. For example, mutations in the gene encoding β-catenin (i.e., CTNNB1) have been associated with cancers such as gastric [Clements et al., Cancer Res. 2002; 62: 3503-3506; Park et al., Cancer Res. 1999; 59: 4257-4260], colorectal [Morin et al., Science 1997; 275: 1787-1790; Ilyas et al., Proc. Natl. Acad. Sci. USA 1997; 94: 10330-10334], intestinal carcinoid [Fujimori et al., Cancer Res. 2001; 61: 6656-6659], ovarian [Sunaga et al., Genes Chrom. Cancer 2001; 30: 316-321], pulmonary adenocarcinoma [Sunaga et al., supra], endometrial [Fukuchi et al., Cancer Res. 1998; 58: 3526-3528; Kobayashi et al., Japan. J. Cancer Res. 1999; 90: 55-59; Mirabelli-Primdahl et al., Cancer Res. 1999; 59: 3346-3351], hepatocellular [Satoh et al., supra.; Wong et al., Cancer 2001; 92: 136-145], hepatoblastoma [Koch et al., Cancer Res. 1999; 59: 269-273], medulloblastoma [Koch et al., Int. J. Cancer 2001; 93: 445-449], pancreatic [Abraham et al., Am. J. Pathol 2002; 160: 1361-1369], thyroid [Garcia-Rostan et al., Cancer Res. 1999; 59: 1811-1815; Garcia-Rostan et al., Am. J. Pathol 2001; 158: 987-996], prostate [Chesire et al., Prostate 2000; 45: 323-334; Voeller et al., Cancer Res. 1998; 58: 2520-2523], melanoma [Reifenberger et al., Int. J. Cancer 2002; 100: 549-556], pilomatricoma [Chan et al., Nature Genet. 1999; 21: 410-413], Wilms' tumor [Koesters et al., J. Pathol 2003; 199: 68-76], pancreatoblastomas [Abraham et al., Am. J. Pathol 2001; 159: 1619-1627], liposarcomas [Sakamoto et al., Arch. Pathol. Lab Med. 2002; 126: 1071-1078], juvenile nasopharyngeal angiofibromas [Abraham et al., Am. J. Pathol. 2001; 158: 1073-1078], desmoid [Tejpar et al., Oncogene 1999; 18: 6615-6620; Miyoshi et al., Oncol. Res. 1998; 10: 591-594], synovial sarcoma [Saito et al., J. Pathol 2000; 192: 342-350]. While loss-of-function mutations have been associated with cancers such as colorectal [Fearon et al., Cell 1990; 61: 759-767; Rowan et al., Proc. Natl. Acad. Sci. USA 2000; 97: 3352-3357], melanoma [Reifenberger et al., Int. J. Cancer 2002; 100: 549-556; Rubinfeld et al., Science 1997; 275: 1790-1792], medulloblastoma [Koch et al., Int. J. Cancer 2001; 93: 445-449; Huang et al., Am. J. Pathol 2000; 156: 433-437] and desmoids [Tejpar et al., Oncogene 1999; 18: 6615-6620; Alman et al., Am J. Pathol. 1997; 151: 329-334].

Other disorders associated with aberrant Wnt signaling, include but are not limited to osteoporosis, osteoarthritis, polycystic kidney disease, diabetes, schizophrenia, vascular disease, cardiac disease, non-oncogenic proliferative diseases, and neurodegenerative diseases such as Alzheimer's disease.

Aberrant Wnt Signaling in Cancers and Leukemia

Aberrant Wnt pathway activation, through the stabilization of β-catenin, plays a central role in tumorigenesis for many colorectal carcinomas. It is estimated that 80% of colorectal carcinomas (CRCs) harbor inactivating mutations in the tumor repressor APC, which allows for uninterrupted Wnt signaling. Furthermore, there is a growing body of evidence that suggests that the Wnt-pathway activation may be involved in melanoma, breast, liver, lung, gastric cancer, and other cancers.

Unregulated activation of the Wnt signaling pathway is also a precursor to the development of leukemia. Experimental evidence exists supporting the oncogenic growth of both myeloid and lymphoid lineages as dependent on Wnt signaling. Wnt signaling has been implicated in regulating both the chronic and acute forms of myeloid leukemia. Granulocyte-macrophage progenitors (GMPs) from chronic myelogenous leukemia patients and blast crisis cells from patients resistant to therapy display activated Wnt signaling. Moreover, inhibition of β-catenin through ectopic expression of Axin decreases the replating capacity of leukemic cells in vitro, suggesting that chronic myelogenous leukemia precursors are dependent on Wnt signaling for growth and renewal. Wnt overexpression also caused GMPs to acquire stem-cell-like properties of long-term self renewal, supporting the hypothesis that Wnt signaling is important for the normal development of blood lineages, but that aberrant Wnt signaling results in the transformation of progenitor cells.

Recent studies also suggest that lymphoid neoplasias may also be influenced by Wnt signaling. Wnt-16 is overexpressed in pre-B-cell leukemia cell lines carrying the E2A-PbX translocation, suggesting that autocrine Wnt activity may contribute to oncogenesis. McWhirter, et al., Proc. Natl. Acad. Sci. USA 96: 11464-11469 (1999). The role of Wnt signaling in the growth and survival of normal B-cell progenitors further supports this notion. Reya et al., Immunity 13: 15-24 (2000); Ranheim et al., Blood 105: 2487-2494 (2005). Autocrine dependence on Wnt has also been proposed for regulating the growth of multiple myeloma, a cancer of terminally differentiated B-cells. Derksen et al., Proc. Natl. Acad. Sci. USA 101: 6122-6127 (2004). Primary myelomas and myeloma cell lines were also found to express stabilized (i.e., independent of degradation complex). Although no mutations in Wnt signaling components was present, the overexpression of several components, including Wnt-5A and Wnt-10B suggest that tumor dependency and cancer self-renewal is not necessarily dependent on mutations appearing in Wnt signaling pathway components, but rather only upon constitutive activation of the pathway itself.

The transition of self-renewing, pluripotent stem cells to myeloid progenitors is accompanied by the downregulation of Wnt signaling. Reya et al, Nature 423: 409-414 (2003). Similarly, the stable expression of β-catenin in lymphoid progenitors restored multiple differentiation options, albeit such cells lacked markers typically associated with either cell type. Baba et al, Immunity 23: 599-609 (2005).

Aberrant Wnt Signaling in Neural Disorders

It has also been observed that the activation of Wnt signaling through β-catenin can increase cycling and expansion of neural progenitors, and that loss of such signaling can result in a loss of progenitor compartment. Chem et al., Science 297: 365-369 (2002); Zechner et al., Dev. Biol. 258: 406-418 (2003). Just as normal activation of Wnt signaling may promote self-renewal of neuronal stem cells, aberrant Wnt pathway activation may be tumorigenic in the nervous system. Experimental evidence supporting this conclusion is the discovery that medulloblastoma, a pediatric brain tumor of the cerebellum, contains mutations in both β-catenin and Axin—thereby suggesting that medulloblastomas arise from primitive progenitors that become transformed in response to uncontrolled Wnt signaling. Zurawel et al., Cancer Res. 58: 896-899 (1998); Dahmen et al., Cancer Res. 61: 7039-7043 (2001); Baeza et al., Oncogene 22: 632-636 (2003). Thus, it is strongly suggested that the inhibition of Wnt signaling by the Wnt antagonists of the invention may be an effective therapeutic in the treatment of various neuronal proliferative disorders, including brain tumors, such as gliomas, astrocytomas, meningiomas, Schwannomas, pituitary tumors, primitive neuroectodermal tumors (PNET), medulloblastomas, craniopharyngioma, pineal region tumors, and non cancerous neurofibromatoses.

Wnt Signaling in Hematopoietic Stem Cells

Hematopoietic stem cells give rise to the adult blood cells of the circulatory system in a process of lineage-committed progenitor cells from multipotential hematopoietic stem cells (HSC). It is also apparent that Wnt signaling contributes to the self-renewal and maintenance of HSC's, and that dysfunctional Wnt signaling is responsible for various disorders resulting from HSC's, such as leukemias and various other blood related cancers. Reya et al., Nature 434: 843-850 (2005); Baba et al., Immunity 23: 599-609 (2005); Jamieson et al., N. Engl. J. Med. 351(7): 657-667 (2004). Wnt signaling is normally reduced as stem cells convert to committed myeloid progenitor cells. Reya et al., Nature 423: 409-414 (2003).

Not only are Wnt ligands themselves produced by HSC's, but Wnt signaling is also active, thereby suggesting autocrine or paracrine regulation. Rattis et al., Curr. Opin. Hematol. 11: 88-94 (2004); Reya et al., Nature 423: 409-414 (2003). Additionally, both β-catenin and Wnt3a promote self renewal of murine HSCs and progenitor cells, while application of Wnt-5A to human hematopoietic progenitors promotes the expansion of undifferentiated progenitors in vitro. Reya et al., supra.; Willert et al., Nature 423: 448-452 (2003); Van Den Berg et al., Blood 92: 3189-3202 (1998).

In addition to HSC's, it is apparent that embryonic stem cells, epidermal stem cells and epithelial stem cells are responsive or dependent on Wnt signaling for maintenance in an undifferentiated, proliferating state. Willert et al., supra; Korinek et al., Nat. Genet. 19: 379-383 (1998); Sato et al., Nat. Med. 10: 55-63 (2004); Gat et al., Cell 95: 605-614 (1998); Zhu et al., Development 126: 2285-2298 (1999). Therefore the inhibition of Wnt signaling with the Wnt antagonists of the present invention may be a therapeutic in the treatment of disorders resulting from dysfunctional hematopoieses, such as leukemias and various blood related cancers, such as acute, chronic, lymphoid and myelogenous leukemias, myelodysplastic syndrome and myeloproliferative disorders. These include myeloma, lymphoma (e.g., Hodgkin's and non-Hodgkin's) chronic and nonprogressive anemia, progressive and symptomatic blood cell deficiencies, polycythemia vera, essential or primary thrombocythemia, idiopathic myelofibrosis, chronic myelomonocytic leukemia (CMML), mantle cell lymphoma, cutaneous T-cell lymphoma, and Waldenstrom macroglobinemia.

Wnt Signaling in Aging

The Wnt signaling pathway may also play a critical role in aging and age-related disorders. As reported in Brack A S, et al., Science, 317(5839):807-10 (2007), muscle stem cells from aged mice were observed to convert from a myogenic to a fibrogenic lineage as they begin to proliferate. This conversion is associated with an increase in canonical Wnt signaling pathway activity in aged myogenic progenitors and can be suppressed by Wnt inhibitors. Additionally, components of serum from aged mice bind to the Frizzled proteins and may account for the elevated Wnt signaling in aged cells. Injection of Wnt3A into young regenerating muscle reduced proliferation and increased deposition of connective tissue.

The Wnt signaling pathway has been further implicated in aging process in studies using the Klotho mouse model of accelerated aging in which it was determined that the Klotho protein physically interacted with and inhibited Wnt proteins. Liu H, et al., Science, 317(5839):803-6 (2007). In a cell culture model, the Wnt-Klotho interaction resulted in the suppression of Wnt biological activity while tissues and organs from Klotho-deficient animals showed evidence of increased Wnt signaling.

Administration and Pharmaceutical Compositions

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of Formula (1), (2), (2A), (3), (3') or (4) and at least one other therapeutic agent as a combined preparation for simultaneous, separate or sequential use in therapy. In one embodiment, the therapy is the treatment of a disease or condition mediated by Wnt. Products provided as a combined preparation include a composition comprising a compound of Formula (1), (2), (2A), (3), (3') or (4), and the other therapeutic agent(s) together in the same pharmaceutical composition, or the compound of Formula (1), (2), (2A), (3), (3') or (4) and the other therapeutic agent(s) in separate form, e.g. in the form of a kit.

In one embodiment, the invention provides a pharmaceutical composition comprising a compound of Formula (1), (2), (2A), (3), (3') or (4), and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of Formula (1), (2), (2A), (3), (3') or (4). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of Formula (1), (2), (2A), (3), (3') and (4) for treating a disease or condition mediated by Wnt, wherein the medicament is prepared for administration with another therapeutic agent.

The invention also provides the use of another therapeutic agent for treating a disease or condition mediated by Wnt, wherein the medicament is administered with a compound of Formula (1), (2), (2A), (3), (3') or (4).

The invention also provides a compound of Formula (1), (2), (2A), (3), (3') and (4) for use in a method of treating a disease or condition mediated by Wnt, wherein the compound of Formula (1), (2), (2A), (3), (3') or (4) is prepared for administration with another therapeutic agent. The invention also provides another therapeutic agent for use in a method of treating a disease or condition mediated by Wnt, wherein the other therapeutic agent is prepared for administration with a compound of Formula (1), (2), (2A), (3), (3') or (4). The invention also provides a compound of Formula (1), (2), (2A), (3), (3') and (4) for use in a method of treating a disease or condition mediated by Wnt, wherein the compound of Formula (1), (2), (2A), (3), (3') or (4) is administered with another therapeutic agent. The invention also provides another therapeutic agent for use in a method of treating a disease or condition mediated by Wnt, wherein the other therapeutic agent is administered with a compound of Formula (1), (2), (2A), (3), (3') or (4).

The invention also provides the use of a Formula (1), (2), (2A), (3), (3') and (4) for treating a disease or condition mediated by Wnt, wherein the patient has previously (e.g. within 24 hours) been treated with another therapeutic agent. The invention also provides the use of another therapeutic agent for treating a disease or condition mediated by Wnt, wherein the patient has previously (e.g. within 24 hours) been treated with a compound of Formula (1), (2), (2A), (3), (3') or (4).

In one embodiment, the other therapeutic agent is a chemotherapeutic agent. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Furthermore, a "chemotherapeutic agent" may include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA®pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Processes for Making Compounds of the Invention

Typically, the compounds of Formula (1), (2), (2A), (3), (3') and (4) can be prepared according to any one of Schemes I, II and III, provided infra.

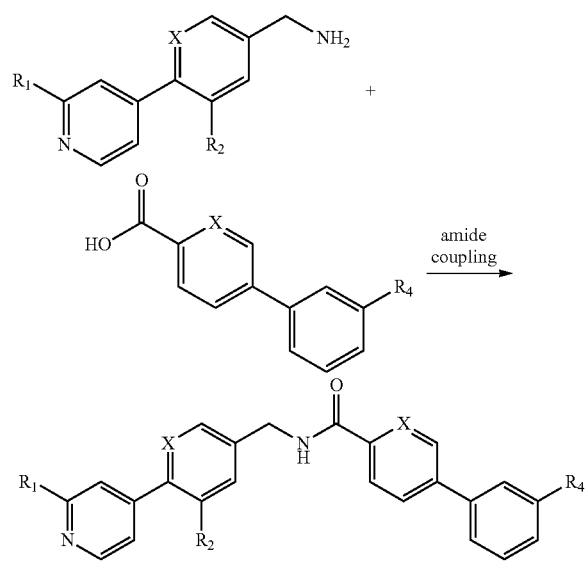

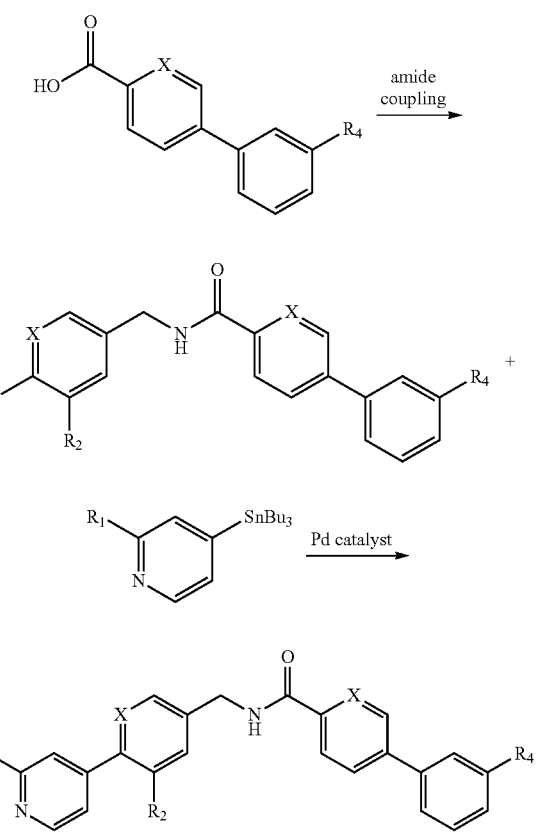

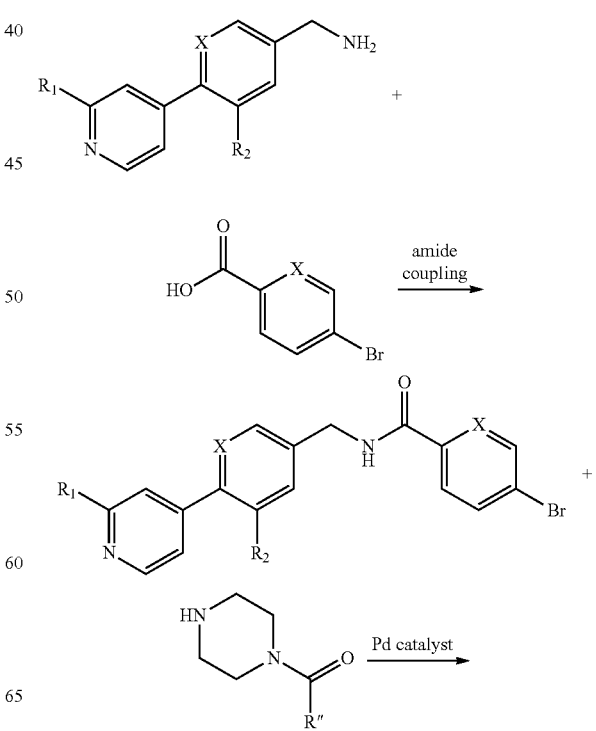

-continued
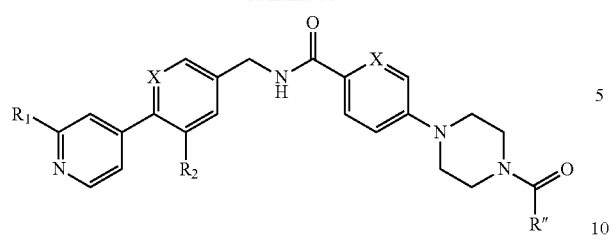
Various amine reagents can be made according to any one of Scheme IV, V, VI and VII:
Scheme IV
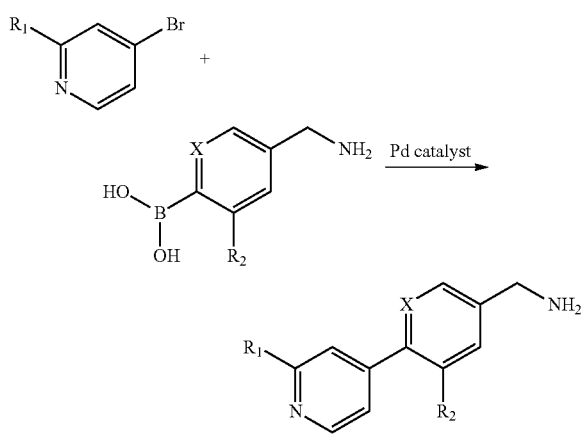
Scheme V
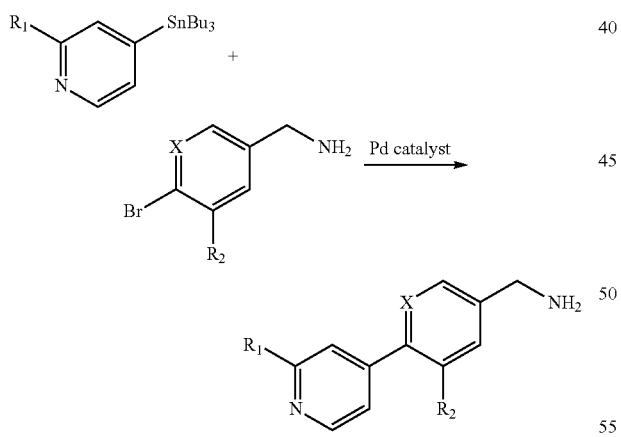
Scheme VI
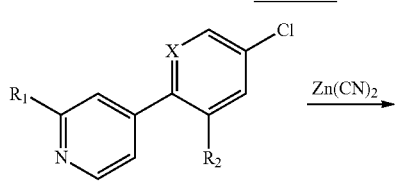
-continued
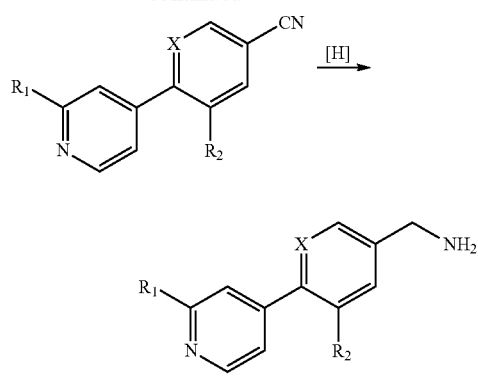
Scheme VII
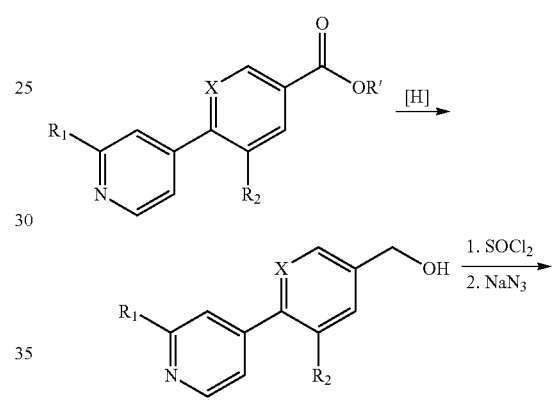
Various acid reagents may be made according to any one of Scheme VIII, IX, X and XI:
Scheme VIII
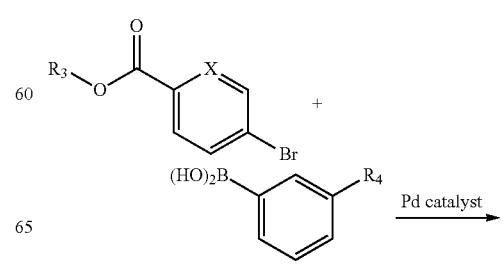

-continued

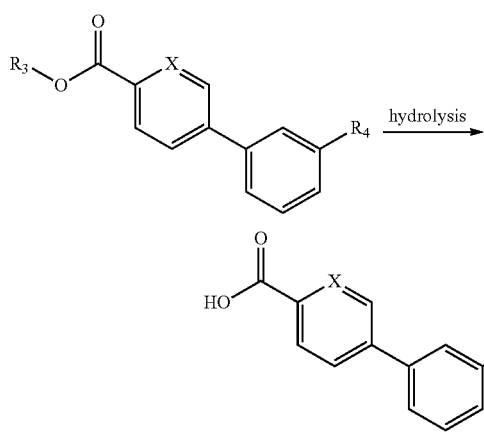

Scheme IX

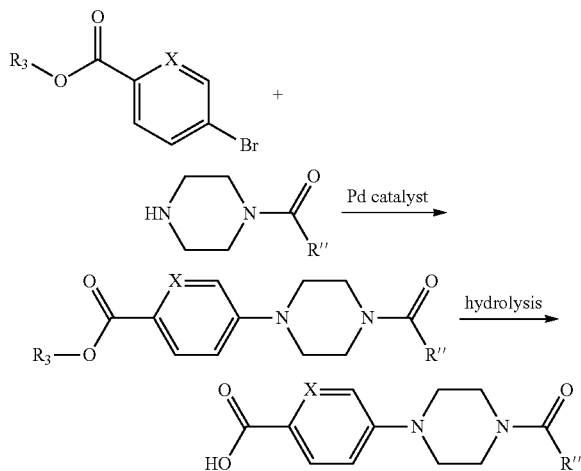

Scheme X

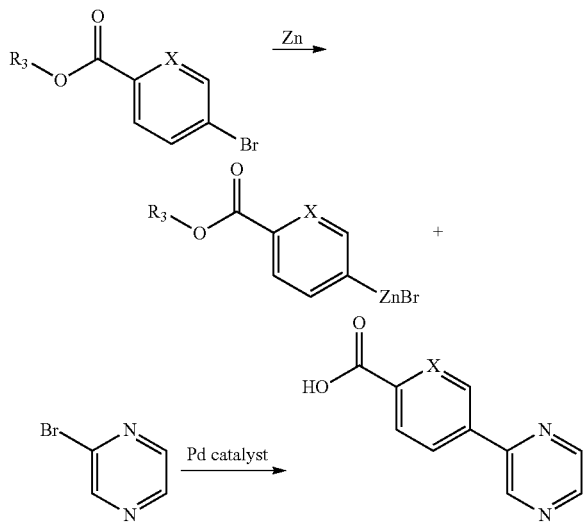

Scheme XI

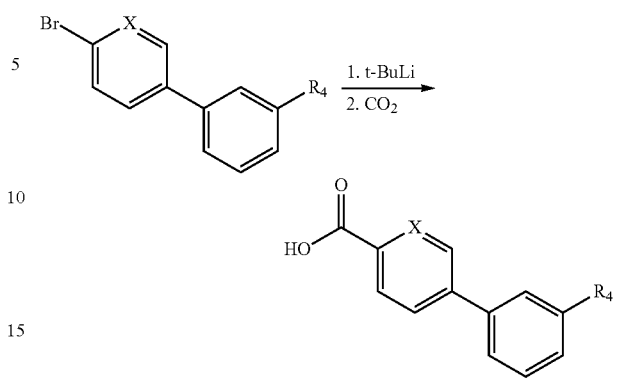

The invention also relates to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. Compounds of the invention and intermediates can also be converted into each other according to methods generally known to those skilled in the art. Intermediates and final products can be worked up and/or purified according to standard methods, e.g. using chromatographic methods, distribution methods, (re-) crystallization, and the like.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps mentioned herein before and hereinafter can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers. Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules. In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers. Salts can be converted into the free compounds in accordance with methods known to those skilled in the art. Metal and ammonium salts can be converted, for example, by treatment with suitable acids, and acid addition salts, for example, by treatment with a suitable basic agent.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, may also be obtained in the form of hydrates, or their crystals may, for example, include the solvent used for crystallization. Different crystalline forms may be present. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21). All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

General Conditions

Mass spectra were collected on Agilent HPLC/MSD systems using electrospray ionization. [M+H]$^+$ refers to monoisotopic molecular weights.

If not indicated otherwise, the analytical HPLC conditions are as follows: The instrument consists of an Agilent 1100 binary pump with degasser, autosampler and photodiode array detector, a Sedere 75 ELSD and an Agilent 1946 MSD mass spectrometer. The column used was a Waters Atlantis dC18, 50×2.1, 5.0 um. Method described as follows:

mobile phase A: H$_2$O+0.05% TFA
mobile phase B: Acetonitrile+0.035% TFA

| Time (min) | Flow rate (mL/min) | % A | % B |
|---|---|---|---|
| 0.00 | 1.00 | 90 | 10 |
| 3.0 | 1.00 | 5 | 95 |
| 3.01 | 1.00 | 0 | 100 |
| 3.49 | 1.00 | 0 | 100 |
| 3.5 | 1.00 | 90 | 10 |

Example 1

N-(4-(pyridazin-4-yl)benzyl)biphenyl-4-carboxamide (1)

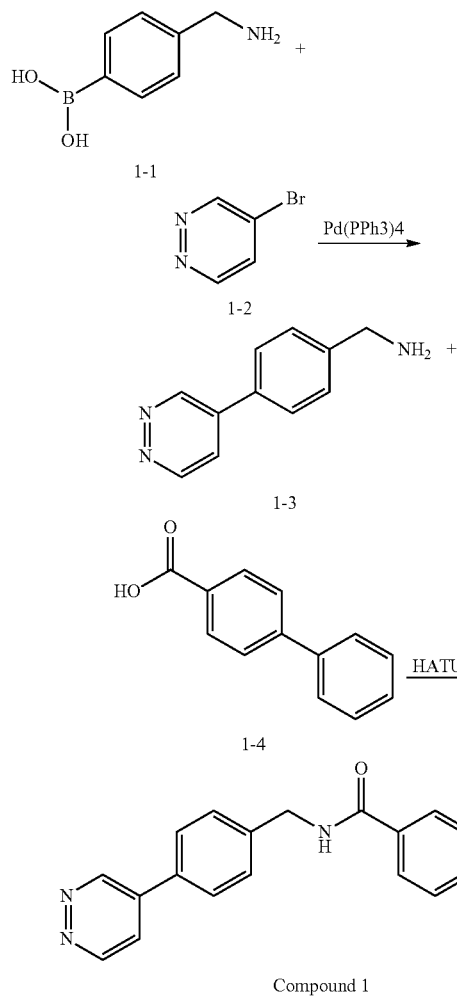

Compound 1

Step 1: To a sealed tube was added 4-(aminomethyl)phenylboronic acid 1-1 (1.87 g, 10 mmol), 4-bromopyridazine 1-2 (1.58 g, 10 mmol), Pd(PPh$_3$)$_4$ (230 mg, 0.2 mmol), saturated Na$_2$CO$_3$ (15 mL), ethanol (15 mL) and toluene (45 mL). The reaction was heated to 110° C. and stirred for 2 hours. The reaction was cooled down to room temperature. The solvent was removed by rotary evaporation. The residue was dissolved in 10% methanol in DCM. The salt was removed by filtration. The filtrate was dried. The crude product was purified by silica-gel flash chromatography, eluted with 10% methanol in DCM to give (4-(pyridazin-4-yl)phenyl)methanamine 1-3 as off-white solid. MS m/z 186.2 (M+1).

Step 2: To a mixture of (4-(pyridazin-4-yl)phenyl)methanamine 1-3 (19 mg, 0.1 mmol), biphenyl-4-carboxylic acid 1-4 (20 mg, 0.1 mmol) and O-(7-azabenzotriazol-1-yl)-N,N,N',N'-tetramethyluroniumhexafluorophosphate (HATU) (38 mg, 0.1 mmol) in DMF (0.5 mL) was added DIEA (0.052 mL, 0.3 mmol) at room temperature. The mixture was stirred at room temperature for 2 hours. The reaction mixture was diluted into DMSO and purified by HPLC to give N-(4-(pyridazin-4-yl)benzyl)biphenyl-4-carboxamide 1 as a white solid. MS m/z 366.2 (M+1). $^1$H NMR 400 MHz (DMSO-d$_6$) δ9.59 (m, 1H), 9.21 (dd, 1H), 9.16 (t, 1H), 7.96 (m, 3H), 7.87 (d, 2H), 7.74 (d, 2H), 7.69 (m, 2H), 7.47-7.41 (m, 4H), 7.37 (m, 1H), 4.52 (d, 2H).

Example 2

5-(3-Fluorophenyl)-N-((6-(1,1-dioxide-thiomorpholino)pyridin-3-yl)methyl)picolinamide (6)

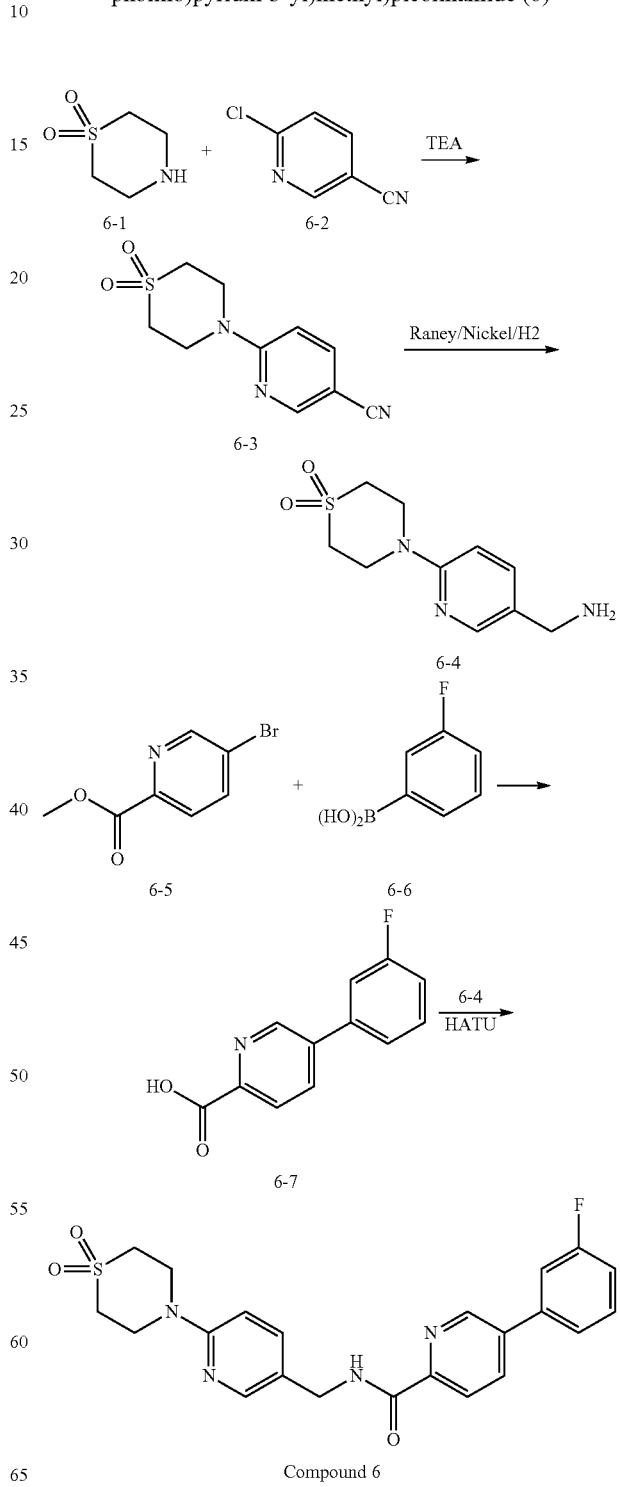

Compound 6

Step 1: To a microwave reaction vessel was added 1,1-dioxide-thiomorpholine 6-1 (1.25 g, 9.3 mmol), 6-chloronicotinonitrile 6-2 (1.21 g, 8.8 mmol), triethylamine (3 mL, 21.6 mmol) and butanol (5 mL). The reaction was irradiated in microwave at 160° C. for 30 mins. After cooling to room temperature, the reaction formed a solid cake. The cake was triturated in 10 mL H₂O at 90° C. After being cooled down, the solid was collected by filtration to give 6-(1,1-dioxide-thiomorpholino)nicotinonitrile 6-3 as off-white solid. MS m/z 238.1 (M+1).

Step 2: To the solution of 6-(1,1-dioxide-thiomorpholino) nicotinonitrile 6-3 (1.13 g, 4.8 mmol) in methanol (15 ml) and THF (9 ml) was added Raney-Nickel (0.7 g) and aqueous ammonium (3 mL). The reaction was stirred under hydrogen balloon at 35° C. for 4 hours. After removing the Raney-Nickel by filtering through celite pad, the filtrate was concentrated to give (6-(1,1-dioxide-thiomorpholino)pyridin-3-yl) methanamine 6-4 as a light green solid. MS m/z 242.1 (M+1).

Step 3: To a round bottom flask was added methyl 5-bromopicolinate 6-5 (900 mg, 4.2 mmol), 3-fluorophenylboronic acid 6-6 (875 mg, 6.3 mmol), Pd(PPh₃)₄ (482 mg, 0.42 mmol), saturated Na₂CO₃ (3 mL), ethanol (3 mL) and toluene (9 mL). The reaction was refluxed at 100° C. for 3 hours. The reaction was cooled down to room temperature, and the precipitate was collected by filtration and briefly washed with ethyl acetate. The sodium salt was acidified with 1N HCl to give 5-(3-fluorophenyl)picolinic acid 6-7 as a white solid. MS m/z 218.1 (M+1).

Step 4: To a mixture of 5-(3-fluorophenyl)picolinic acid 6-7 (22 mg, 0.1 mmol), (6-(1,1-dioxide-thiomorpholino)pyridin-3-yl)methanamine 6-4 (21 mg, 0.1 mmol) and O-(7-azabenzotriazol-1-yl)-N,N,N',N'-tetramethyluronium-hexafluorophosphate (HATU) (38 mg, 0.1 mmol) in DMF (0.5 mL) was added DIEA (0.052 mL, 0.3 mmol) at room temperature. The mixture was stirred at room temperature for 2 hours. The reaction mixture was diluted into DMSO and purified by HPLC to give 5-(3-fluorophenyl)-N-46-(1,1-dioxide-thiomorpholino)pyridin-3-yl)methyl)picolinamide 6 as a white solid. MS m/z 441.2 (M+1). ¹H NMR 400 MHz (DMSO-d₆) δ 9.37 (t, 1H), 8.98 (s, 1H), 8.34 (dd, 1H), 8.16 (d, 1H), 8.12 (d, 1H), 7.73-7.56 (m, 4H), 7.33 (m, 1H), 7.00 (d, 1H), 4.41 (d, 2H), 4.03 (b, 4H), 3.07 (b, 4H).

Example 3

5-(3-Fluorophenyl)-N-((6-(1,1-dioxide-thiomorpholino)pyridin-3-yl)methyl)picolinamide (8)

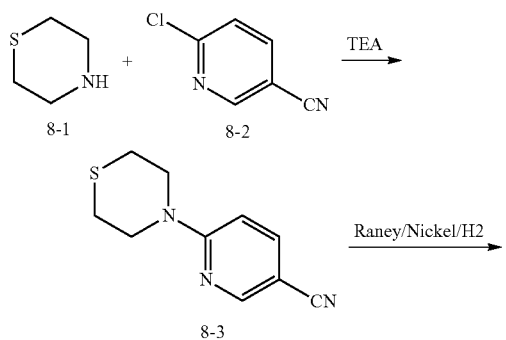

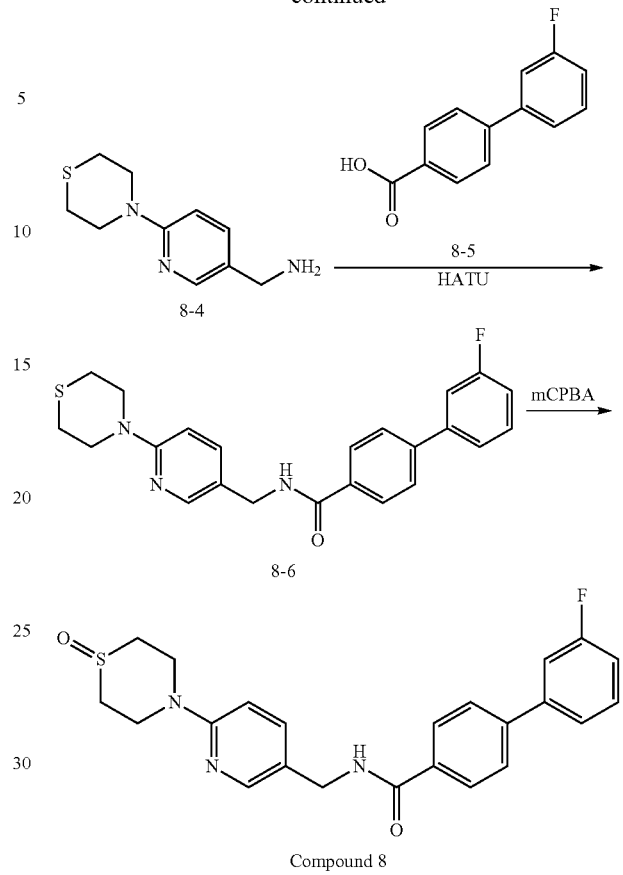

Compound 8

Step 1: To a round bottom flask was added thiomorpholine 8-1 (3.6 g, 34.8 mmol), 6-chloronicotinonitrile 8-2 (4.0 g, 29 mmol), triethylamine (8 mL, 58 mmol) and butanol (10 mL). The reaction was stirred at 100° C. for 1 hour. After cooling to room temperature, the reaction formed a solid cake. The cake was triturated in 50 mL H₂O at 100° C. After cooling, the solid was collected by filtration to give 6-thiomorpholinonicotinonitrile 8-3 as an off-white solid. MS m/z 206.1 (M+1).

Step 2: To the solution of 6-thiomorpholinonicotinonitrile 8-3 (1.0 g, 4.8 mmol) in methanol (15 ml) and THF (9 ml) was added Raney-Nickel (0.7 g) and aqueous ammonium (3 mL). The reaction was stirred under hydrogen balloon at 35° C. for 4 hours. After removing the Raney-Nickel by filtering through celite pad, the filtrate was concentrated to give (6-thiomorpholinopyridin-3-yl)methanamine 8-4 as a light green solid. MS m/z 210.1 (M+1).

Step 3: To a mixture of 3'-fluorobiphenyl-4-carboxylic acid 8-5 (51 mg, 0.24 mmol), (6-thiomorpholinopyridin-3-yl) methanamine 8-4 (45 mg, 0.21 mmol) and O-(7-azabenzotriazol-1-yl)-N,N,N',N'-tetramethyluroniumhexafluorophosphate (HATU) (91 mg, 0.24 mmol) in DMF (1.0 mL) was added DIEA (0.1 mL, 0.64 mmol) at room temperature. The mixture was stirred at room temperature for 2 hours. The reaction mixture was diluted into DMSO and purified by HPLC to give 3'-fluoro-N-((6-thiomorpholinopyridin-3-yl) methyl)biphenyl-4-carboxamide 8-6. MS m/z 408.2 (M+1).

Step 4: To a solution of 3'-fluoro-N-((6-thiomorpholinopyridin-3-yl)methyl)biphenyl-4-carboxamide 8-6 (44 mg, 0.11 mmol) in DCM (15 mL) at 0° C. was added mCPBA in DCM (5 mL) dropwise. The reaction was stirred at 0° C. for 2 hours. The solvent was removed by rotary evaporation. The crude product was purified by HPLC to give 3'-fluoro-N-((6-(1-oxide-thiomorpholino)pyridin-3-yl)methyl)biphenyl-4-carboxamide 8 as a white solid. MS m/z 424.2 (M+1). $^1$H NMR 400 MHz (DMSO-$d_6$) δ 9.31 (t, 1H), 8.34 (s, 1H), 8.18 (d, 2H), 8.03 (d, 2H), 7.80-7.68 (m, 4H), 7.47 (m, 1H), 7.19 (d, 1H), 4.59 (d, 2H), 4.30 (m, 2H), 4.15 (t, 2H), 3.08 (t, 2H), 2.86 (m, 2H).

Example 4

N-(4-(pyridin-3-yl)benzyl)biphenyl-4-carboxamide (10)

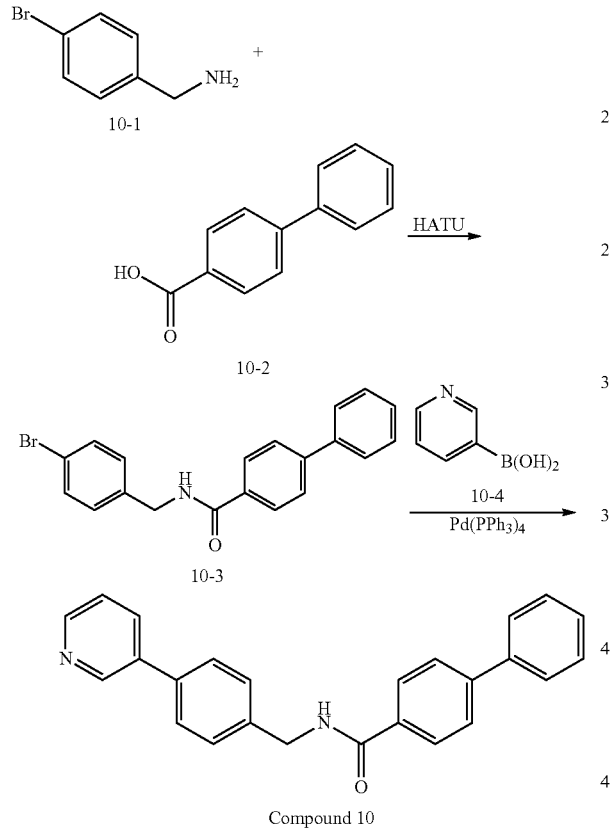

Compound 10

Step 1: To a solution of biphenyl-4-carboxylic acid 10-2 (0.89 g, 4.5 mmol), O-(7-azabenzotriazol-1-yl)-N,N,N',N'-tetramethyluroniumhexafluorophosphate (HATU) (1.7 g, 4.5 mmol) and DIEA (2.34 mL, 13.5 mmol) in DMF (15.0 mL) was added (4-bromophenyl)methanamine 10-1 (1.0 g, 4.5 mmol) at room temperature. The reaction was stirred at room temperature for 1 hour. Ethyl acetate was added to the reaction mixture, and the resulting precipitate was collected by vacuum filtration to give N-(4-bromobenzyl)biphenyl-4-carboxamide 10-3 as a white solid. MS m/z 366.2 (M+1).

Step 2: To a sealed tube was added pyridin-3-ylboronic acid 10-4 (25 mg, 0.21 mmol), N-(4-bromobenzyl)biphenyl-4-carboxamide $10^{-3}$ (50 mg, 0.14 mmol), Pd(PPh$_3$)$_4$ (16 mg, 0.014 mmol), saturated Na$_2$CO$_3$ (2.1 mL), ethanol (0.7 mL) and toluene (0.7 mL). The reaction was heated to 110° C. and stirred for 2 hours. After cooling to room temperature, the reaction was diluted into ethyl acetate, washed with brine. The organic phase was taken to dryness by rotary evaporation. The residue was purified by HPLC to give N-(4-(pyridin-3-yl)benzyl)biphenyl-4-carboxamide 10 as off-white solid. MS m/z 385.2 (M+1). $^1$H NMR 400 MHz (DMSO-$d_6$) δ 9.18 (t, 1H), 8.89 (s, 1H), 8.57 (d, 1H), 8.08 (m, 3H), 7.81 (d, 2H), 7.75-7.70 (m, 4H), 7.52-7.42 (m, 6H), 4.57 (d, 2H).

Example 5

N-(4-(2-methylpyridin-4-yl)benzyl)-4-(pyridin-2-yl)benzamide (13)

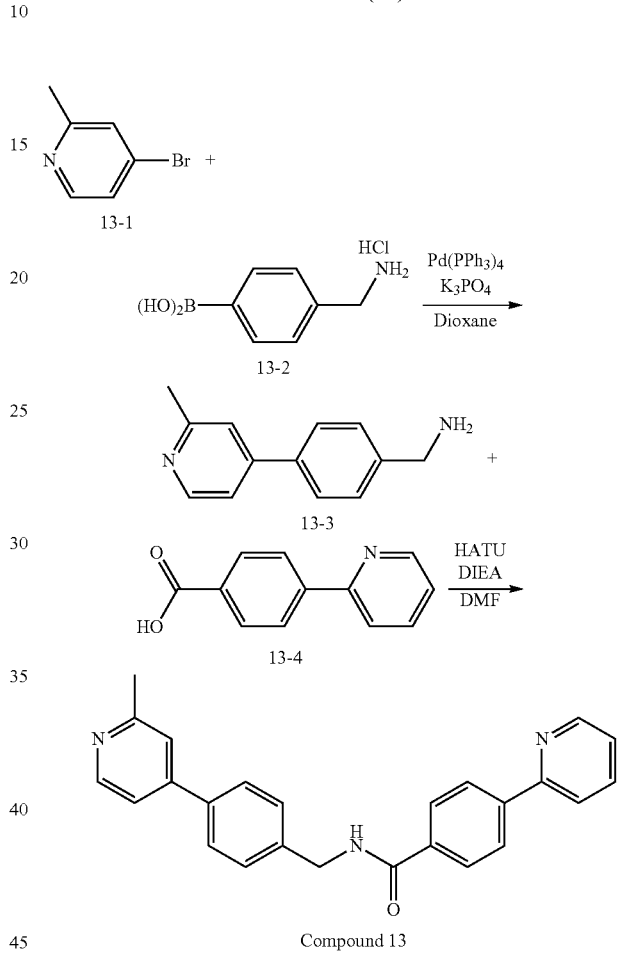

Compound 13

Step 1: A mixture of 4-bromo-2-methylpyridine 13-1 (516 mg, 3.00 mmol), (4-(aminomethyl)phenyl)boronic acid hydrochloride 13-2 (422 mg, 2.25 mmol), Pd(PPh$_3$)$_4$ (173 mg, 0.15 mmol) and K$_3$PO$_4$ (1.7 g, 8 mmol) in anhydrous dioxane (10 mL) was stirred at 96° C. under argon overnight. After cooling to room temperature, the mixture was filtered through celite and washed with ethyl acetate. The filtrate was concentrated by rotavap and the residue subjected to silica gel column chromatography with 7% ammonia-saturated methanol in dichloromethane as eluent to give (4-(2-methylpyridin-4-yl)phenyl)methanamine 13-3 as an oil.

Step 2: To a mixture of (4-(2-methylpyridin-4-yl)phenyl)methanamine 13-3 (10 mg, 0.05 mmol), 4-(pyridin-2-yl)benzoic acid 13-4 (10 mg, 0.05 mmol), and HATU (23 mg, 0.06 mmol) were added N,N-diisopropylethylamine (DIEA, 17 μL, 0.1 mmol) and DMF (0.5 mL). The solution was stirred overnight at room temperature and was subjected directly to reverse phase preparative HPLC to yield N-(4-(2-methylpyridin-4-yl)benzyl)-4-(pyridin-2-yl)benzamide 13 as white powder. MS m/z 380.2 (M+1). $^1$H NMR 400 MHz (CDCl$_3$) δ

8.65-8.60 (m, 1H), 8.41 (d, 1H), 7.99-7.85 (m, 4H), 7.80-7.70 (m, 2H), 7.65-7.50 (m, 3H), 7.45 (d, 2H), 7.34 (bs, 1H), 7.32-7.27 (m, 2H), 4.66 (d, 2H), 2.56 (s, 3H).

Example 6

N-(3-fluoro-4-(2-methylpyridin-4-yl)benzyl)-4-(pyrimidin-5-yl)benzamide (15)

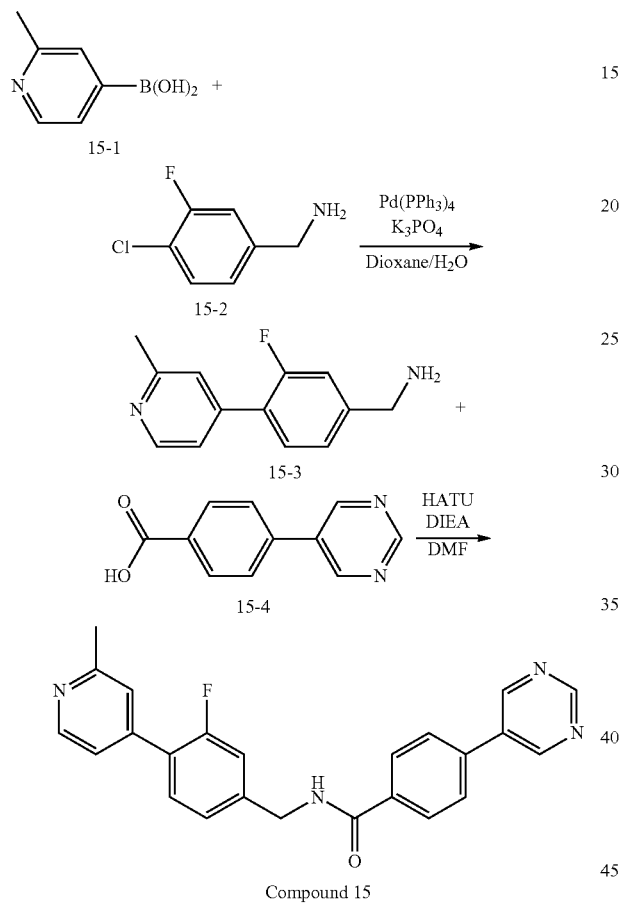

Compound 15

Step 1: A mixture of (2-methylpyridin-4-yl)boronic acid 15-1 (822 mg, 6.2 mmol), (4-chloro-3-fluorophenyl)methanamine 15-2 (798 mg, 5.00 mmol), Pd(PPh$_3$)$_4$ (173 mg, 0.15 mmol) and K$_3$PO$_4$ (1.59 g, 7.50 mmol) in dioxane (10 mL) and water (1 mL) was stirred at 96° C. under argon overnight. After cooling to room temperature, the mixture was filtered through celite, washed with ethyl acetate, and dried with Na$_2$SO$_4$. The filtrate was concentrated by rotavap and the residue subjected to silica gel column chromatography with 6% ammonia-saturated methanol in dichloromethane as eluent to give (3-fluoro-4-(2-methylpyridin-4-yl)phenyl)methanamine 15-3 as an oil.

Step 2: To a mixture of (3-fluoro-4-(2-methylpyridin-4-yl)phenyl)methanamine 15-3 (10.8 mg, 0.05 mmol), 4-(pyrimidin-5-yl)benzoic acid 15-4 (10.0 mg, 0.05 mmol), and HATU (23 mg, 0.06 mmol) were added N,N-diisopropylethylamine (DIEA, 17 μL, 0.1 mmol) and DMF (0.5 mL). The solution was stirred overnight at room temperature and was subjected directly to reverse phase preparative HPLC to yield N-(3-fluoro-4-(2-methylpyridin-4-yl)benzyl)-4-(pyrimidin-5-yl)benzamide 15 as a white powder. MS m/z 399.2 (M+1).

Example 7

N-((2'-methyl-[2,4'-bipyridin]-5-yl)methyl)-4-(pyrazin-2-yl)benzamide (18)

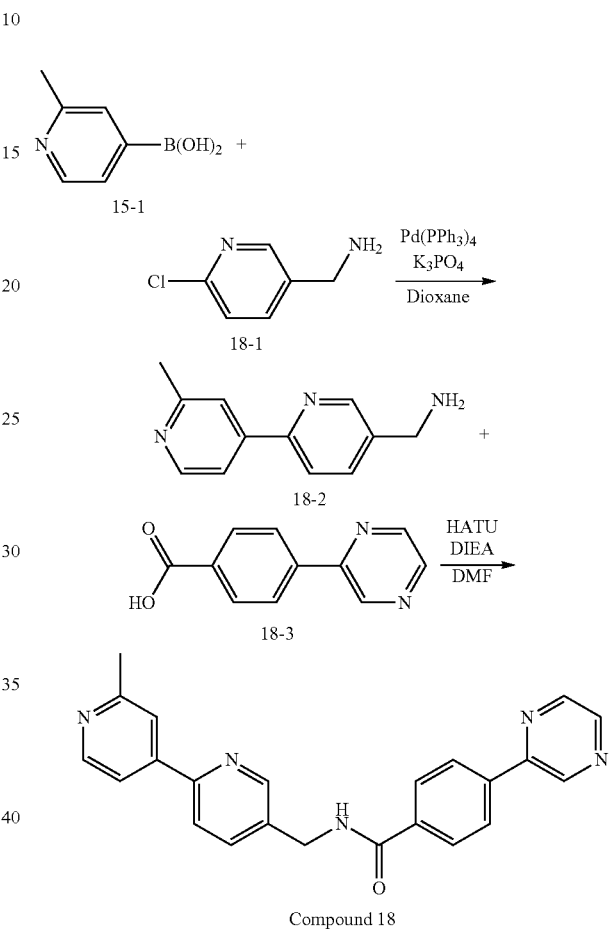

Compound 18

Step 1: A mixture of (2-methylpyridin-4-yl)boronic acid 15-1 (476 mg, 3.48 mmol), (6-chloropyridin-3-yl)methanamine 18-1 (496 mg, 3.48 mmol), Pd(PPh$_3$)$_4$ (202 mg, 0.175 mmol) and K$_3$PO$_4$ (1113 mg, 5.25 mmol) in dioxane (5 mL) was stirred at 96° C. under argon overnight. After cooling to room temperature, the mixture was filtered through celite and washed with ethyl acetate. The filtrate was concentrated by rotavap and the residue subjected to silica gel column chromatography with 7% ammonia-saturated methanol in dichloromethane as eluent to give (2'-methyl-[2,4'-bipyridin]-5-yl)methanamine 18-2 as an oil.

Step 2: To a mixture of (2'-methyl-[2,4'-bipyridin]-5-yl)methanamine 18-2 (10.0 mg, 0.05 mmol), 4-(pyrazin-2-yl)benzoic acid 18-3 (10.0 mg, 0.05 mmol), and HATU (23 mg, 0.06 mmol) were added N,N-diisopropylethylamine (DIEA, 17 μL, 0.1 mmol) and DMF (0.5 mL). The solution was stirred overnight at room temperature and was subjected directly to reverse phase preparative HPLC to yield N-42'-methyl-[2,4'-bipyridin]-5-yl)methyl)-4-(pyrazin-2-yl)benzamide 18 as a white powder. MS m/z 382.2 (M+1). $^1$H NMR 400 MHz (CDCl$_3$) δ 9.06 (d, 1H), 8.73 (d, 1H), 8.66 (dd, 1H), 8.59 (d, 1H), 8.56 (d, 1H), 8.15-8.08 (m, 2H), 8.00-7.91 (m, 2H), 7.86 (dd, 1H), 7.80-7.73 (m, 2H), 7.65 (dd, 1H), 6.90 (t, 1H), 4.76 (d, 2H), 2.64 (s, 3H).

Example 8

6-(4-Acetylpiperazin-1-yl)-N-(3-fluoro-4-(2-methylpyridin-4-yl)benzyl)nicotinamide (20)

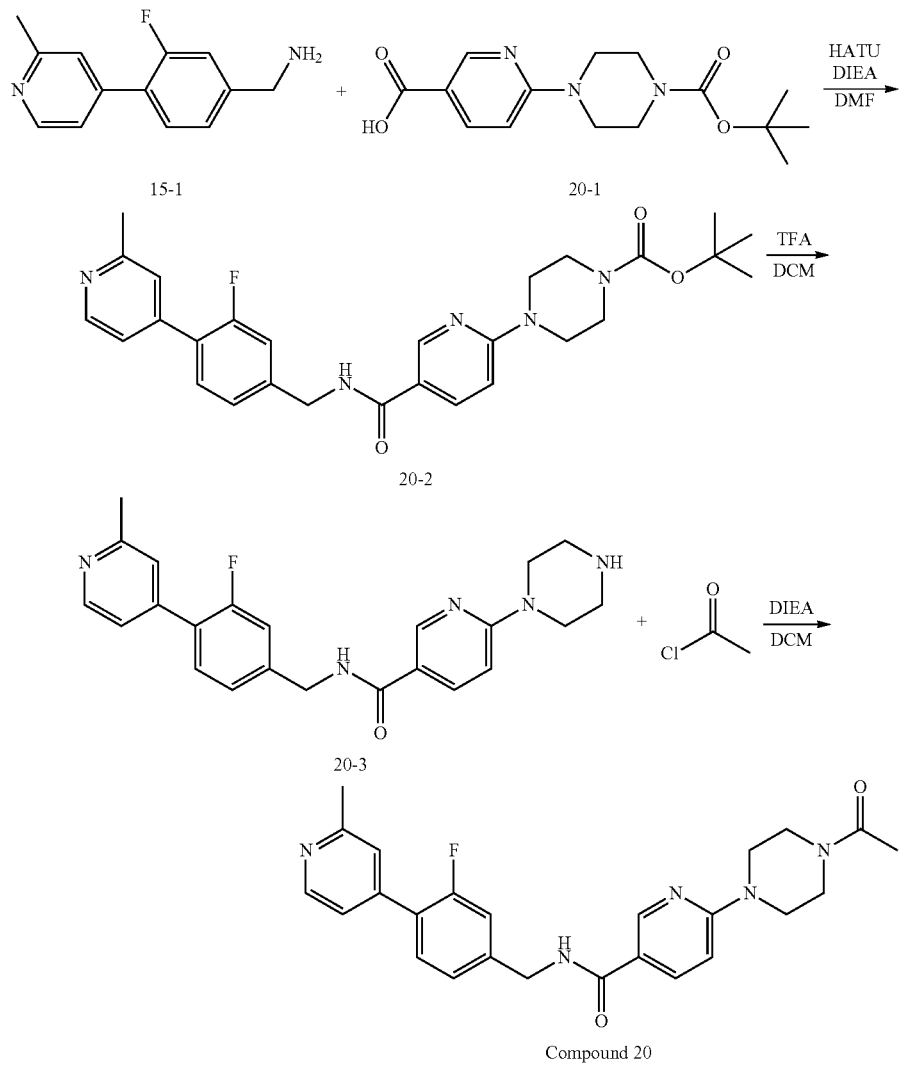

Step 1: To a mixture of (3-fluoro-4-(2-methylpyridin-4-yl)phenyl)methanamine 15-1 (64 mg, 0.296 mmol), 6-(4-(tert-butoxycarbonyl)piperazin-1-yl)nicotinic acid 20-1 (96 mg, 0.313 mmol) and HATU (124 mg, 0.326 mmol) were added N,N-diisopropylethylamine (DIEA, 78 µL, 0.447 mmol) and DMF (1.0 mL). The solution was stirred overnight. The mixture was then diluted with ethyl acetate (30 mL), and washed with 10% $Na_2CO_3$ aqueous solution, saturated $NH_4Cl$ aqueous solution and water. After the organic solution was dried over $Na_2SO_4$, the solvent was evaporated under reduced pressure and dried under vacuum, resulting in crude tert-butyl 4-(5-((3-fluoro-4-(2-methylpyridin-4-yl)benzyl)carbamoyl)pyridin-2-yl)piperazine-1-carboxylate 20-2.

Step 2: The crude tert-butyl 4-(5-((3-fluoro-4-(2-methylpyridin-4-yl)benzyl)carbamoyl)pyridin-2-yl)piperazine-1-carboxylate 20-2 in dichloromethane (2 mL) was treated with trifluoroacetic acid (TFA, 0.5 mL), and the solution was stirred overnight at room temperature. Evaporation under reduced pressure (with the addition of some toluene to aid evaporation of the residual TFA) followed by lyophilization gave crude N-(3-fluoro-4-(2-methylpyridin-4-yl)benzyl)-6-(piperazin-1-yl)nicotinamide 20-3.

Step 3: To a solution of crude N-(3-fluoro-4-(2-methylpyridin-4-yl)benzyl)-6-(piperazin-1-yl)nicotinamide 20-3 (10 mg, 0.025 mmol) and DIEA (21.8 µL, 0.125 mmol) in dichloromethane (1.0 mL) was added acetyl chloride (3.6 µL, 0.05 mmol), and the solution was stirred 30 minutes at room temperature. The solution was diluted with ethyl acetate (30 mL) and washed with 10% $Na_2CO_3$ aqueous solution and water. After the organic phase was dried over $Na_2SO_4$, the solvent was evaporated under reduced pressure and the residue subjected to preparative reverse phase HPLC to give 6-(4-acetylpiperazin-1-yl)-N-(3-fluoro-4-(2-methylpyridin-4-yl)benzyl)nicotinamide 20 as a solid. MS m/z 448.2 (M+1). $^1$H NMR 400 MHz (CDCl$_3$) δ 8.63 (d, 1H), 8.54 (d, 1H), 7.98 (dd, 1H), 7.42 (dd, 1H), 7.33 (bs, 1H), 7.29-7.25 (m, 1H), 7.22

(dd, 1H), 7.16 (dd, 1H), 6.64 (d, 1H), 6.61 (t, 1H), 4.67 (d, 2H), 3.78-3.70 (m, 4H), 3.65-3.54 (m, 4H), 2.61 (s, 3H), 2.14 (s, 3H).

Example 9

N-(3-fluoro-4-(1-methyl-6-oxo-1,6-dihydropyridin-3-yl)benzyl)-4-(pyrazin-2-yl)benzamide

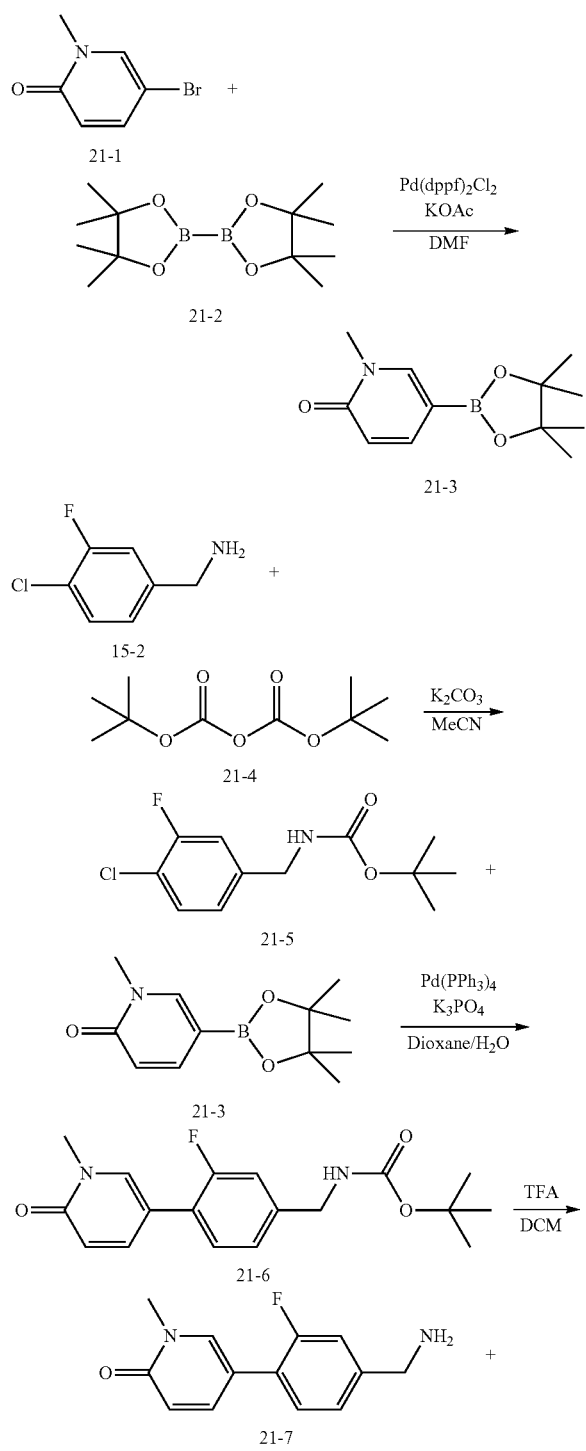

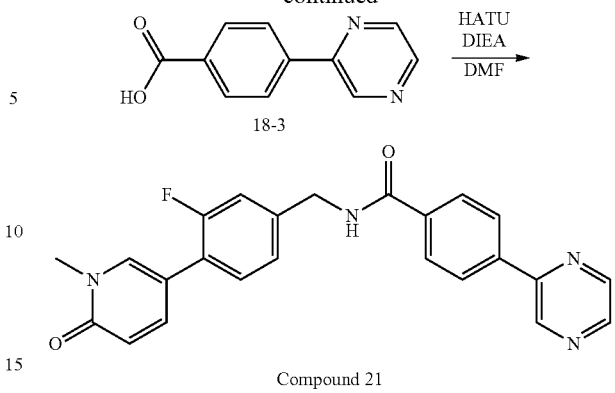

Step 1: A mixture of 5-bromo-1-methylpyridin-2(1H)-one 21-1 (350 mg, 1.87 mmol), (4,4',4',5,5,5',5'-heptamethyl-[2,2'-bi(1,3,2-dioxaborolan)]-4-yl)methylium 21-2 (617 mg, 2.43 mmol), potassium acetate (550 mg, 5.61 mmol) and Pd(dppf)$_2$Cl$_2$ dichloromethane complex (82 mg, 0.1 mmol) in DMF (10 mL) was stirred at 80° C. for 10 hours. After cooling to room temperature, the mixture was filtered through celite, concentrated by evaporation under reduced pressure and then redistributed between ethyl acetate and water. The organic phase was dried over Na$_2$SO$_4$ and concentrated by evaporation under reduced pressure. The resulting residue was subjected to silica gel column chromatography with 1:1 ethyl acetate/hexanes as eluent to give 1-methyl-5-(4,4,5,5-tetramethyl-1,3,2-dioxaborolan-2-yl)pyridin-2(1H)-one 21-3.

Step 2: To a solution of (4-chloro-3-fluorophenyl)methanamine 15-2 (320 mg, 2.0 mmol) in acetonitrile (5 mL) at 0° C. was added Boc anhydride 21-4 (458 mg, 2.1 mmol) and K$_2$CO$_3$ (303 mg, 2.2 mmol), and the mixture was stirred overnight at room temperature. The mixture was filtered, evaporated with rotavap, and redistributed between ethyl acetate and 5% aqueous Na$_2$CO$_3$ solution. Then the organic phase was dried over Na$_2$SO$_4$ and concentrated with rotavap. The residue was subjected to column chromatography with 1:1 ethyl acetate/hexanes as eluent to give tert-butyl 4-chloro-3-fluorobenzylcarbamate 21-5 as an oil.

Step 3: A mixture of 1-methyl-5-(4,4,5,5-tetramethyl-1,3,2-dioxaborolan-2-yl)pyridin-2(1H)-one 21-3 (78 mg, 0.33 mmol), tert-butyl 4-chloro-3-fluorobenzylcarbamate 21-5 (94 mg, 0.36 mmol), Pd(PPh$_3$)$_4$ (38 mg, 0.033 mmol) and K$_3$PO$_4$ (140 mg, 0.66 mmol) in dioxane (1.2 mL) and water (0.1 mL) was stirred at 96° C. under argon overnight. After cooling to room temperature, the mixture was filtered through celite and concentrated by evaporation under reduced pressure. The residue was subjected to silica gel column chromatography to give crude tert-butyl 3-fluoro-4-(1-methyl-6-oxo-1,6-dihydropyridin-3-yl)benzylcarbamate 21-6.

Step 4: The crude tert-butyl 3-fluoro-4-(1-methyl-6-oxo-1,6-dihydropyridin-3-yl)benzylcarbamate 21-6 (10 mg, obtained in Step 3) was stirred with trifluoroacetic acid (TFA, 0.3 mL) in dichloromethane (1 mL) overnight. Evaporation under reduced pressure (with the addition of some toluene to aid evaporation of the residual TFA) followed by lyophilization gave the crude 5-(4-(aminomethyl)-2-fluorophenyl)-1-methylpyridin-2(1H)-one 21-7.

Step 5: To a mixture of the 5-(4-(aminomethyl)-2-fluorophenyl)-1-methylpyridin-2(1H)-one 21-7 (obtained in Step 4), 4-(pyrazin-2-yl)benzoic acid 18-3 (5.0 mg, 0.025 mmol), and HATU (9.5 mg, 0.025 mmol) were added N,N-diisopropylethylamine (DIEA, 17 μL, 0.1 mmol) and DMF (0.5 mL).

The solution was stirred overnight at room temperature and was subjected directly to reverse phase preparative HPLC to give N-(3-fluoro-4-(1-methyl-6-oxo-1,6-dihydropyridin-3-yl)benzyl)-4-(pyrazin-2-yl)benzamide 21 (2.5 mg). MS m/z 415.2 (M+1).

Example 10

N-((2'-fluoro-[2,4'-bipyridin]-5-yl)methyl)-4-(pyrazin-2-yl)benzamide (24)

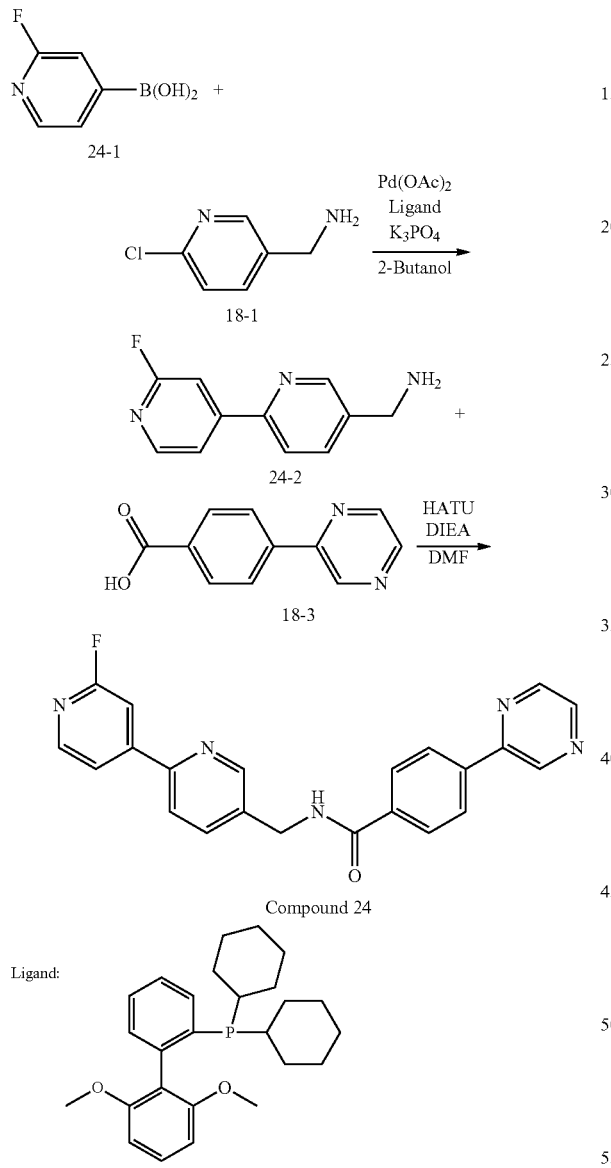

Step 1: A mixture of (2-fluoropyridin-4-yl)boronic acid 24-1 (200 mg, 1.42 mmol), (6-chloropyridin-3-yl)methanamine 18-1 (142 mg, 1.00 mmol), Pd(OAc)₂ (12 mg, 0.05 mmol), dicyclohexyl(2',6'-dimethoxy-[1,1'-biphenyl]-2-yl)phosphine (41 mg, 0.1 mmol) and K₃PO₄ (424 mg, 2.00 mmol) in 2-butanol (1 mL) was stirred at 100° C. under argon overnight. After cooling to room temperature, the mixture was filtered through celite (washed with ethyl acetate), concentrated by rotavap and the residue subjected to silica gel column chromatography with 7% ammonia-saturated methanol in dichloromethane as eluent to give (2'-fluoro-[2,4'-bipyridin]-5-yl)methanamine 24-2 as an oil.

Step 2: To a mixture of (2'-fluoro-[2,4'-bipyridin]-5-yl)methanamine 24-2 (15 mg, 0.074 mmol), 4-(pyrazin-2-yl)benzoic acid 18-3 (18 mg, 0.09 mmol), and HATU (36 mg, 0.095 mmol) were added N,N-diisopropylethylamine (DIEA, 26 µL, 0.15 mmol) and DMF (0.6 mL). The solution was stirred overnight at room temperature and was subjected directly to reverse phase preparative HPLC to yield N-((2'-fluoro-[2,4'-bipyridin]-5-yl)methyl)-4-(pyrazin-2-yl)benzamide 24 as a solid. MS m/z 386.2 (M+1).

Example 11

4-(Pyrazin-2-yl)-N-(4-(2-(trifluoromethyl)pyridin-4-yl)benzyl)benzamide (28)

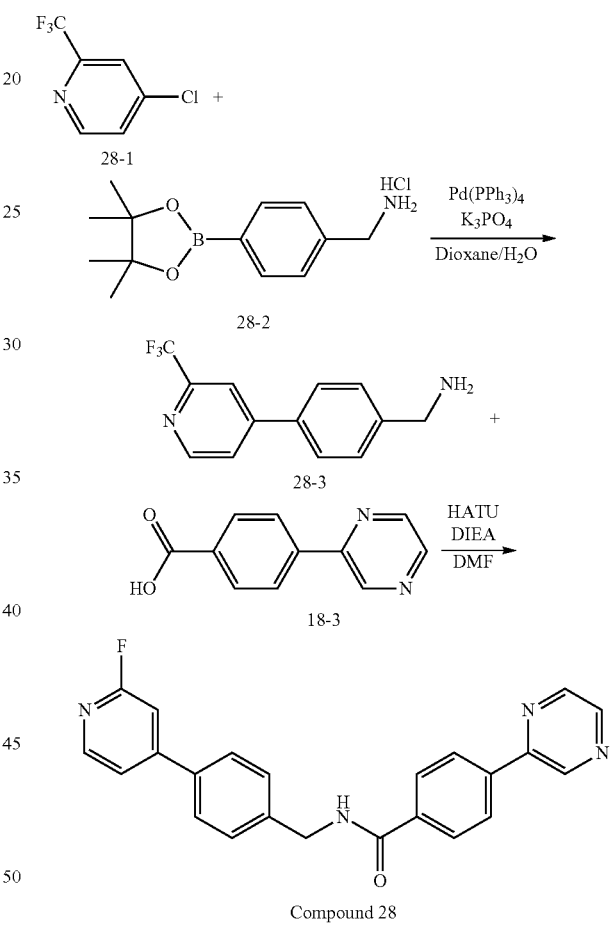

Step 1: A mixture of 4-chloro-2-(trifluoromethyl)pyridine 28-1 (54 mg, 0.3 mmol), (4-(4,4,5,5-tetramethyl-1,3,2-dioxaborolan-2-yl)phenyl)methanamine hydrochloride 28-2 (81 mg, 0.3 mmol), Pd(PPh₃)₄ (35 mg, 0.03 mmol) and K₃PO₄ (212 mg, 1.0 mmol) in dioxane (1.6 mL) and water (0.2 mL) was stirred at 96° C. under argon overnight. After cooling to room temperature, the mixture was filtered through celite (washed with ethyl acetate) and the filtrate was redistributed between ethyl acetate and water. The organic phase was dried over Na₂SO₄ and concentrated with rotavap. The residue was subjected to silica gel column chromatography with 7% ammonia-saturated methanol in dichloromethane as eluent to give (4-(2-(trifluoromethyl)pyridin-4-yl)phenyl)methanamine 28-3 as an oil.

Step 2: To a mixture of (4-(2-(trifluoromethyl)pyridin-4-yl)phenyl)methanamine 28-3 (16 mg, 0.063 mmol), 4-(pyrazin-2-yl)benzoic acid 18-3 (13 mg, 0.065 mmol), and HATU (26 mg, 0.068 mmol) were added N,N-diisopropylethylamine (DIEA, 17 µL, 0.1 mmol) and DMF (0.5 mL). The solution was stirred overnight at room temperature and was subjected directly to reverse phase preparative HPLC to yield 4-(pyrazin-2-yl)-N-(4-(2-(trifluoromethyl)pyridin-4-yl)benzyl)benzamide 28 as a solid. MS m/z 435.0 (M+1).

Example 12

N-((2'-fluoro-3-methyl-2,4'-bipyridin-5-yl)methyl)-5-(3-fluorophenyl)picolinamide (30)

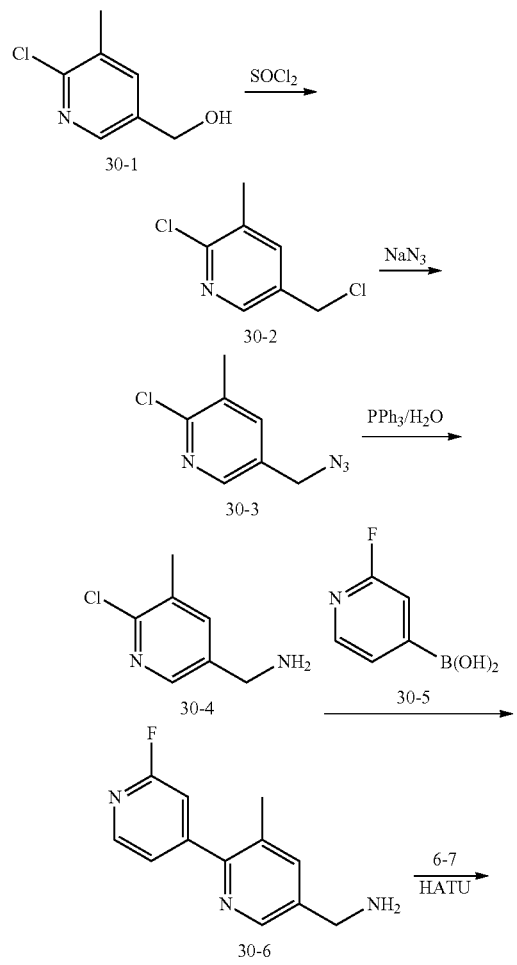

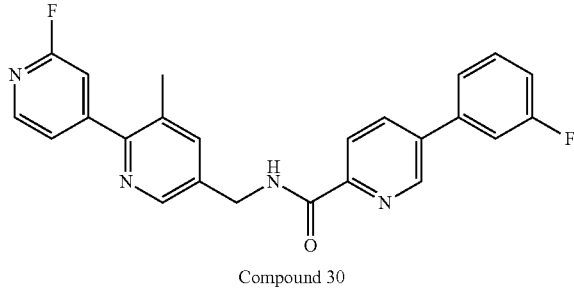

Compound 30

Step 1: To a solution of (6-chloro-5-methylpyridin-3-yl)methanol 30-1 (2.51 g) in anhydrous DCM (30 mL) was added SOCl$_2$ (6.6 mL) at 0° C. The reaction was warmed to room temperature and stirred for 2 hours. The solvent and excess SOCl$_2$ were removed by rotary evaporation. The crude product was partitioned between ethyl acetate and saturated sodium bicarbonate. The organic phase was washed with brine and dried over Na$_2$SO$_4$.

Step 2: To the solution of 2-chloro-5-(chloromethyl)-3-methylpyridine 30-2 (2.7 g, 15.4 mmol) in DMF (20 mL) was added sodium azide (1.5 g, 23.1 mmol) and H$_2$O (1 mL). The reaction was stirred at room temperature for 3 hours. The reaction mixture was partitioned between ethyl acetate and saturate sodium bicarbonate. The organic phase was washed with brine and dried over Na$_2$SO$_4$.

Step 3: To the solution of 5-(azidomethyl)-2-chloro-3-methylpyridine 30-3 (2.0 g, 11 mmol) in THF (20 mL) was added PPh$_3$ (3.17, 12 mmol) slowly. After 2 hours, H$_2$O was added to the reaction mixture and the reaction was stirred for additional 15 hours, and the solvent was removed. The crude product was partitioned between ethyl acetate (50 mL) and 0.2 N HCl (50 mL). The aqueous phase was dried to give (6-chloro-5-methylpyridin-3-yl)methanamine HCl salt 30-4 as a white solid.

Step 4: To a reaction vial was added (6-chloro-5-methylpyridin-3-yl)methanamine HCl salt 30-4 (738 mg, 3.8 mmol), 2-fluoropyridin-4-ylboronic acid 30-5 (800 mg, 5.7 mmol), Pd(OAc)$_2$ (106 mg, 0.47 mmol), S-Phos (194 mg, 0.47 mmol) and K$_3$PO$_4$ (2.0 g, 9.5 mmol). The vial was evacuated and backfilled with nitrogen, and 2-butanol (5 mL) was added via syringe. The reaction was stirred at room temperature for 10 mins and then 100° C. for 3 hours. After cooling to room temperature, the reaction mixture was partitioned between DCM and H$_2$O, and extracted with DCM three times. The organic phase was combined and dried. The crude product was purified by silica gel flash chromatography, eluted with 10% methanol in DCM to give (2'-fluoro-3-methyl-2,4'-bipyridin-5-yl)methanamine 30-5. MS m/z 218.2 (M+1).

Step 5: To a mixture of 5-(3-fluorophenyl)picolinic acid 6-7 (32 mg, 0.15 mmol), (2'-fluoro-3-methyl-2,4'-bipyridin-5-yl)methanamine 30-5 (28 mg, 0.13 mmol) and O-(7-azabenzotriazol-1-yl)-N,N,N',N'-tetramethyluroniumhexafluorophosphate (HATU) (60 mg, 0.16 mmol) in DMF (1.0 mL) was added DIEA (0.068 mL, 0.39 mmol) at room temperature. The mixture was stirred at room temperature for 2 hours. The reaction mixture was diluted into DMSO and purified by HPLC to give N-((2'-fluoro-3-methyl-2,4'-bipyridin-5-yl)methyl)-5-(3-fluorophenyl)picolinamide 30 as a white solid. MS m/z 417.2 (M+1). $^1$H NMR 400 MHz (DMSO-d$_6$) δ 9.54 (t, 1H), 8.95 (dd, 1H), 8.47 (d, 1H), 8.29 (m, 2H), 8.07 (dd, 1H), 7.69 (m, 2H), 7.63 (m, 1H), 7.55 (m, 1H), 7.48 (m, 1H), 7.29 (m, 2H), 4.52 (d, 2H), 2.28 (s, 3H).

Example 13

5-(3-Fluorophenyl)-N-((2'-(trifluoromethyl)-2,4'-bipyridin-5-yl)methyl)picolinamide (33)

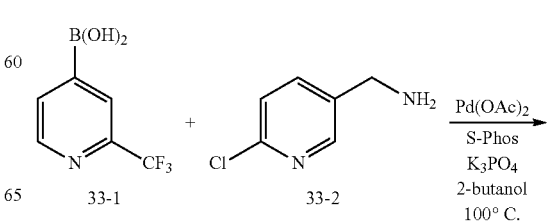

-continued

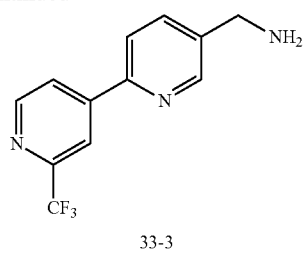

33-3

-continued

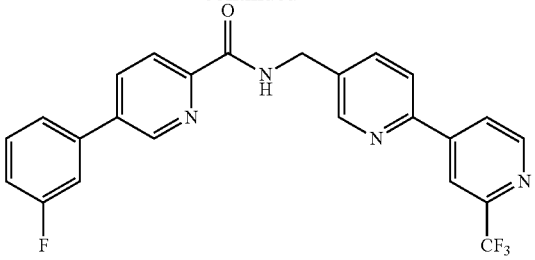

Compound 33

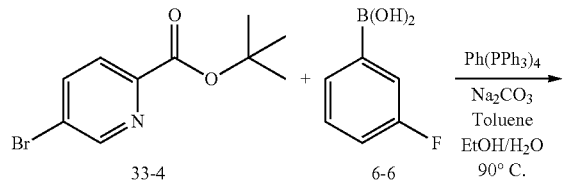

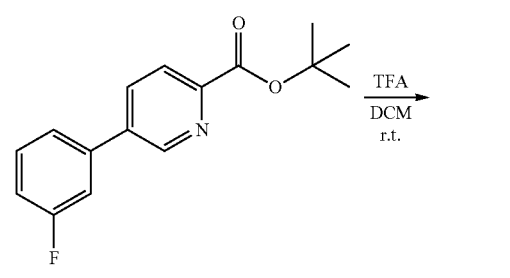

33-5

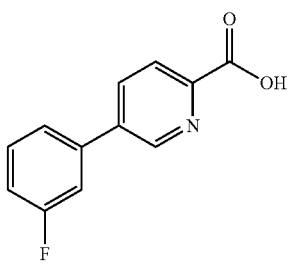

6-7

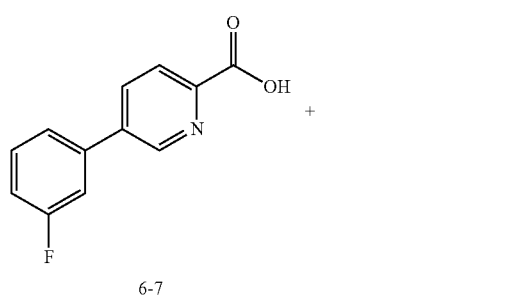

6-7

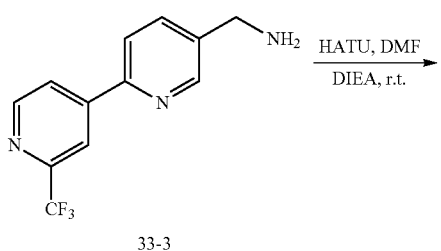

33-3

Step 1: To a flask containing (6-chloropyridin-3-yl)methanamine 33-2 (375 mg, 2.63 mmol), 2-(trifluoromethyl)pyridin-4-ylboronic acid 33-1 (500 mg, 2.63 mmol), Pd(OAc)₂ (34 mg, 0.15 mmol), 2-dicyclohexylphosphino-2',6'-dimethoxybiphenyl (S-Phos) (124 mg, 0.30 mmol) and potassium phosphate (1.90 g, 9.00 mmol) under argon was added 2-butanol (4 mL). The mixture was stirred at 100° C. for 10 hours. After cooling to room temperature, the mixture was filtered through celite cake. The filtrate was diluted with ethyl acetate, washed with H₂O and brine, dried over Na₂SO₄, and concentrated to dryness by rotary evaporation. The crude product was purified by silica gel flash chromatography, eluted with 5% methanol containing ~7N ammonia in dichloromethane to give (2'-(trifluoromethyl)-2,4'-bipyridin-5-yl)methanamine 33-3 as a yellow solid. MS m/z 254.1 (M+1)

Step 2: To a reaction flask was added tert-butyl 5-bromopicolinate 33-4 (516 mg, 2.00 mmol), 3-fluorophenylboronic acid 6-6 (280 mg, 2.00 mmol), Pd(PPh₃)₄ (140 mg, 0.20 mmol), toluene (10 mL), ethanol (2 mL) and 2M Na₂CO₃ (3 mL). The reaction mixture was bubbled with nitrogen for 2 minutes and stirred at 90° C. for 10 hours with the flask sealed. After cooling to room temperature, the reaction mixture was diluted with ethyl acetate (100 mL) and washed with saturated NaHCO₃ aqueous solution, H₂O and brine. The organic phase was dried over Na₂SO₄ and concentrated to dryness by rotary evaporation. The crude product was purified by silica gel flash chromatography, and eluted with 30% hexanes in ethyl acetate to give tert-butyl 5-(3-fluorophenyl)picolinate 33-5 as a white solid. MS m/z 274.1 (M+1).

Step 3: To a solution of tert-butyl 5-(3-fluorophenyl)picolinate 33-5 (414 mg, 1.51 mmol) in dichloromethane (3 mL) was added TFA (1.5 mL) dropwise at room temperature. The mixture was stirred at room temperature for 2 hours. The mixture was diluted with dichloromethane (100 mL) and H₂O (100 mL), adjusted with Na₂CO₃ to pH around 4, and separated. The organic layer was washed with H₂O and brine, dried over Na₂SO₄, concentrated to dryness to afford 5-(3-fluorophenyl)picolinic acid 6-7 as an off-white solid. MS m/z 218.1 (M+1)

Step 4: To a mixture of 5-(3-fluorophenyl)picolinic acid 6-7 (22 mg, 0.10 mmol), tert-butyl 5-(3-fluorophenyl)picolinate 33-3 (25 mg, 0.10 mmol) and O-(7-azabenzotriazol-1-yl)-N,N,N',N'-tetramethyluroniumhexafluorophosphate (HATU) (38 mg, 0.10 mmol) in DMF (1 mL) was added N,N-diisopropylethylamine (DIEA) (0.5 mL, 0.30 mmol). The mixture was stirred at room temperature for 2 hours. The solvent was removed by rotary evaporation. The residue was purified by reverse phase HPLC to give 5-(3-fluorophenyl)-N-q2'-(trifluoromethyl)-2,4'-bipyridin-5-yl)methyl)picolinamide 33 as a white powder. MS m/z 453.70 (M+1); ¹H NMR 400 MHz (DMSO-d₆) δ 9.63 (t, 1H, J=6.4 Hz), 9.01 (d, 1H, J=1.6 Hz), 8.89 (d, 1H, J=5.2 Hz), 8.77 (d, 1H, J=1.6 Hz), 8.50 (s, 1H), 8.38-8.33 (m, 2H), 8.26 (d, 1H, J=8.0 Hz), 8.13

(d, 1H, J=8.0 Hz), 7.95 (dd, 1H, J₁=8.2 Hz, J₂=2.0 Hz), 7.75-7.68 (m, 2H), 7.62-7.56 (m, 1H), 7.32 (m, 1H), 4.62 (d, 2H, J=6.4 Hz).

Example 14

6'-(Dimethylamino)-N-((2'-fluoro-2,4'-bipyridin-5-yl)methyl)-3,3'-bipyridine-6-carboxamide (38)

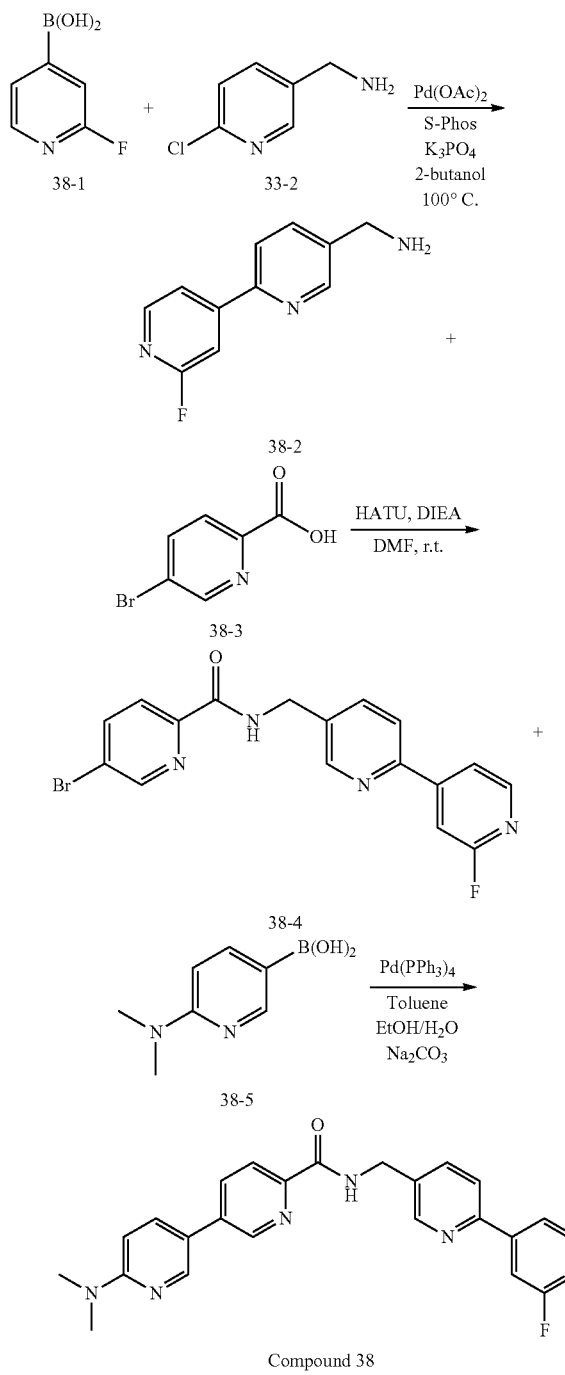

Compound 38

Step 1: To a flask containing (6-chloropyridin-3-yl)methanamine 33-2 (642 mg, 4.50 mmol), 2-fluoropyridin-4-ylboronic acid 38-1 (634 mg, 4.50 mmol), Pd(OAc)₂ (51 mg, 0.23 mmol), S-Phos (186 mg, 0.45 mmol) and potassium phosphate (2.85 g, 13.50 mmol) under argon was added 2-butanol (5 mL). The mixture was stirred at 100° C. for 10 hours. After cooling to room temperature, the mixture was filtered through celite cake. The filtrate was diluted with ethyl acetate, washed with H₂O and brine, dried over Na₂SO₄, and concentrated to dryness by rotary evaporation. The crude product was purified by silica gel flash chromatography, eluted with 5% methanol containing ~7N ammonia in dichloromethane to give (2'-fluoro-2,4'-bipyridin-5-yl)methanamine 38-2 as yellow solid. MS m/z 204.1 (M+1)

Step 2: To a mixture of 5-bromopicolinic acid 38-3 (309 mg, 1.53 mmol), (2'-fluoro-2,4'-bipyridin-5-yl)methanamine 38-2 (312 mg, 1.53 mmol) and HATU (582 mg, 1.53 mmol) in DMF (7 mL) was added DIEA (0.76 mL, 4.59 mmol). The mixture was stirred at room temperature for 2 hours. The mixture was diluted with ethyl acetate (100 mL), washed with H₂O and brine, dried over Na₂SO₄, and concentrated to dryness by rotary evaporation. The crude product was purified by silica gel flash chromatography, eluted with 5% methanol containing ~7N ammonia in dichloromethane to give 5-bromo-N-((2'-fluoro-2,4'-bipyridin-5-yl)methyl)picolinamide 38-4 as yellow solid. MS m/z 387.1 (M+1)

Step 3: To a tube was added 5-bromo-N-((2'-fluoro-2,4'-bipyridin-5-yl)methyl)picolinamide 38-4 (38 mg, 0.10 mmol), 6-(dimethylamino)pyridin-3-ylboronic acid 38-5 (33 mg, 0.20 mmol), Pd(PPh₃)₄ (11 mg, 0.01 mmol), toluene (0.4 mL), ethanol (0.1 mL) and 2M Na₂CO₃ (0.15 mL). The reaction mixture was bubbled with nitrogen for 2 minutes and stirred at 90° C. for 10 hours with the tube sealed. After cooling to room temperature, the reaction mixture was diluted with ethyl acetate (100 mL) and washed with saturated NaHCO₃ aqueous solution, H₂O and brine. The organic phase was dried over Na₂SO₄ and concentrated to dryness by rotary evaporation. The crude product was purified with reverse phase HPLC to give 6'-(dimethylamino)-N-((2'-fluoro-2,4'-bipyridin-5-yl)methyl)-3,3'-bipyridine-6-carboxamide 38 as a white powder. MS m/z 429.20 (M+1); ¹H NMR 400 MHz (DMSO-d₆) δ 9.52 (t, 1H, J=6.4 Hz), 8.94 (d, 1H, J=2.4 Hz), 8.73 (d, 1H, J=2.0 Hz), 8.60 (d, 1H, J=2.4 Hz), 8.35 (d, 1H, J=5.2 Hz), 8.22 (m, 1H), 8.15 (d, 1H, J=8.0 Hz), 8.06-7.93 (m, 4H), 7.80 (s, 1H), 6.78 (d, 1H, J=9.2 Hz), 4.60 (d, 2H, J=6.4 Hz), 3.09 (s, 6H).

Example 15

5-(Pyrazin-2-yl)-N-((2'-(trifluoromethyl)-2,4'-bipyridin-5-yl)methyl)picolinamide (41)

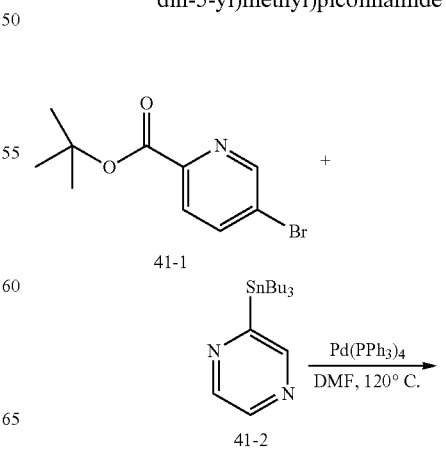

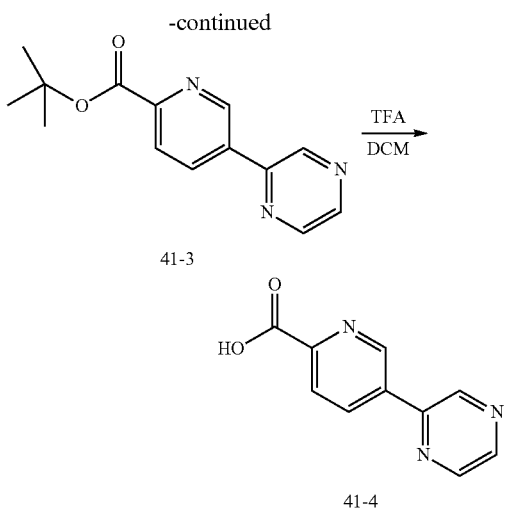

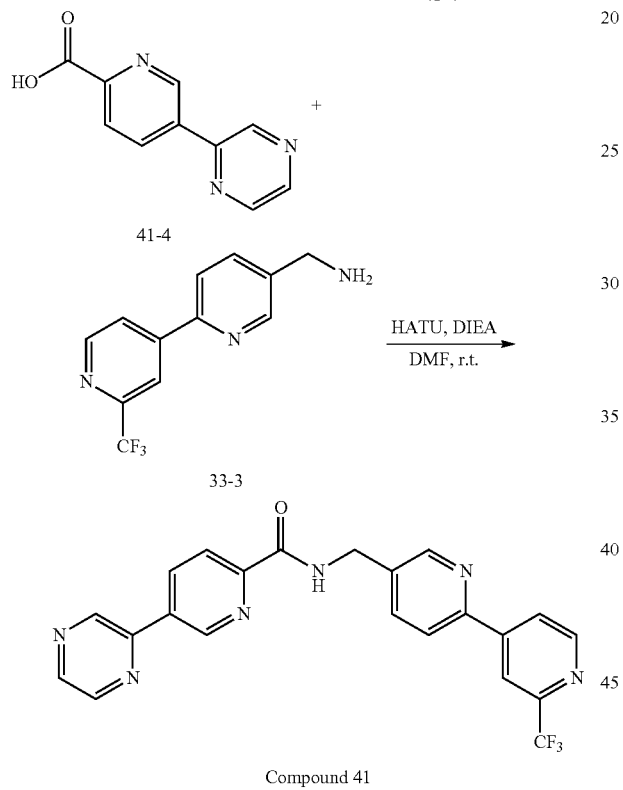

Compound 41

Step 1: To a flask containing tert-butyl 5-bromopicolinate 41-1 (1.55 g, 6.0 mmol), 2-(tributylstannyl)pyrazine 41-2 (2.21 g, 6.0 mmol) and Pd(PPh$_3$)$_4$ (426 mg, 0.6 mmol) under argon was added DMF (15 mL). The mixture was stirred at 120° C. for 10 hours. After cooling to room temperature, the mixture was diluted with ethyl acetate, washed with H$_2$O and brine, dried over Na$_2$SO$_4$, and concentrated to dryness by rotary evaporation. The crude product was purified by silica gel flash chromatography, eluted with 5% methanol in dichloromethane to give tert-butyl 5-(pyrazin-2-yl)picolinate 41-3 as a pale yellow solid. MS m/z 258.1 (M+1)

Step 2: To a solution of tert-butyl 5-(pyrazin-2-yl)picolinate 41-3 (1.11 g, 4.32 mmol) in dichloromethane (4.5 mL) was added TFA (4.5 mL) dropwise at room temperature. The mixture was stirred for 10 hours, and then the solvents were removed by rotary evaporation. The resulting pale yellow oil was further dried under lyophilizer to afford 5-(pyrazin-2-yl) picolinic acid 41-4 in TFA salt as a pale yellow solid. MS m/z 202.1 (M+1)

Step 3: To a mixture of 5-(pyrazin-2-yl)picolinic acid 41-4 (20 mg, 0.10 mmol), (2'-(trifluoromethyl)-2,4'-bipyridin-5-yl)methanamine 33-3 (25 mg, 0.10 mmol) and HATU (38 mg, 0.10 mmol) in DMF (0.5 mL) was added DIEA (0.05 mL, 0.30 mmol). The mixture was stirred at room temperature for 2 hours. The solvent was removed by rotary evaporation. The crude product was purified by reverse phase HPLC to give 5-(pyrazin-2-yl)-N-42'-(trifluoromethyl)-2,4'-bipyridin-5-yl)methyl)picolinamide 41 as a white powder. MS m/z 437.10 (M+1); $^1$H NMR 400 MHz (DMSO-d$_6$) δ 9.50 (t, 1H, J=6.4 Hz), 9.44 (m, 2H), 8.89 (d, 1H, J=5.2 Hz), 8.83-8.82 (m, 1H), 8.78 (m, 1H), 8.75-8.70 (m, 2H), 8.50 (s, 1H), 8.37 (dd, J$_1$=5.0 Hz, J$_2$=1.2 Hz), 8.27-8.20 (m, 2H), 7.97 (dd, 1H, J$_1$=8.2 Hz, J$_2$=2.4 Hz), 4.63 (d, 2H, J=6.4 Hz).

Example 16

6-(Pyrazin-2-yl)-N-((2'-(trifluoromethyl)-2,4'-bipyridin-5-yl)methyl)nicotinamide (42)

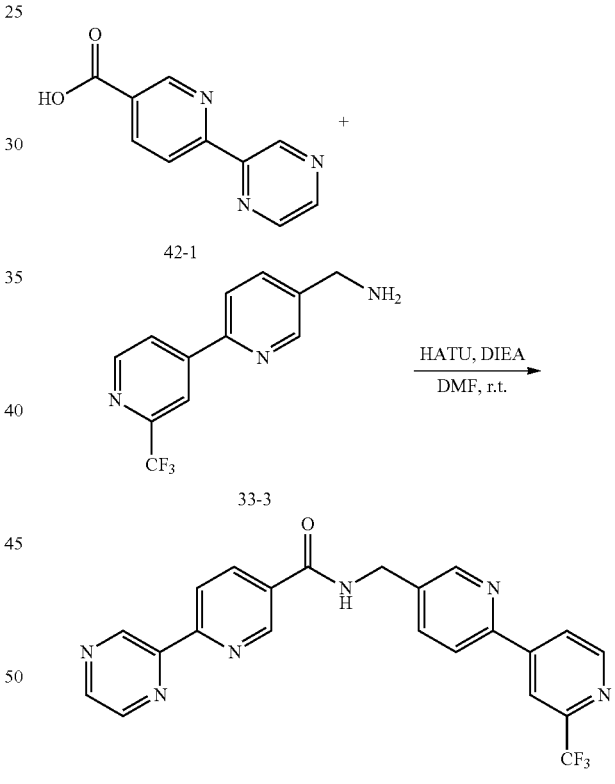

Compound 42

To a mixture of 6-(pyrazin-2-yl)nicotinic acid 42-1 (20 mg, 0.10 mmol), (2'-(trifluoromethyl)-2,4'-bipyridin-5-yl)methanamine 33-3 (25 mg, 0.10 mmol) and HATU (38 mg, 0.10 mmol) in DMF (0.5 mL) was added DIEA (0.05 mL, 0.30 mmol) at the room temperature. The mixture was stirred for 2 hours. The solvent was removed by rotary evaporation. The crude product was purified by reverse phase HPLC to give 6-(pyrazin-2-yl)-N-42'-(trifluoromethyl)-2,4'-bipyridin-5-yl)methyl)nicotinamide 42 as a white powder. MS m/z 437.10 (M+1); $^1$H NMR 400 MHz (DMSO-d$_6$) δ 9.58 (d, 1H, J=1.2 Hz), 9.50 (t, 1H, J=6.0 Hz), 9.20 (m, 1H), 8.89 (d, 1H, J=5.2

Hz), 8.81-8.77 (m, 3H), 8.52 (s, 1H), 8.45 (m, 2H), 8.39 (dd, $J_1$=5.0 Hz, $J_2$=1.2 Hz), 8.29 (d, 1H, J=8.4 Hz), 7.99 (dd, 1H, $J_1$=8.2 Hz, $J_2$=2.0 Hz), 4.65 (d, 2H, J=5.6 Hz).

Example 17

N-((2'-Fluoro-2,4'-bipyridin-5-yl)methyl)-5-(3-(methylsulfonyl)phenyl)picolinamide (43)

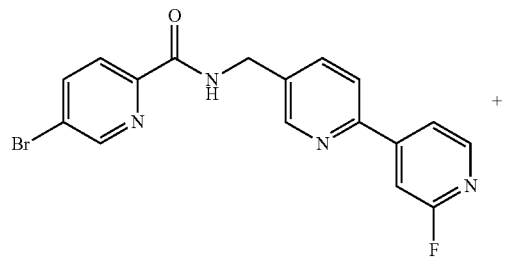

38-4

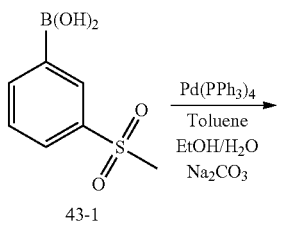

43-1

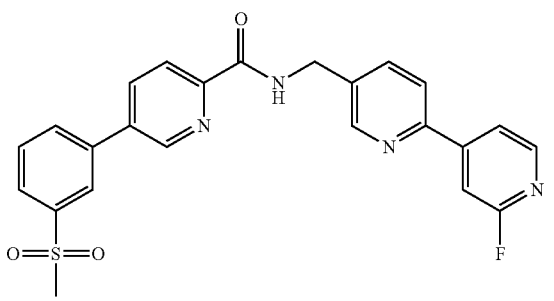

Compound 43

Step 1: To a tube was added 5-bromo-N-((2'-fluoro-2,4'-bipyridin-5-yl)methyl)picolinamide 38-4 (38 mg, 0.10 mmol), 3-(methylsulfonyl)phenylboronic acid 43-1 (33 mg, 0.20 mmol), Pd(PPh$_3$)$_4$ (11 mg, 0.01 mmol), toluene (0.4 mL), ethanol (0.1 mL) and 2M Na$_2$CO$_3$ (0.15 mL). The reaction mixture was bubbled with nitrogen for 2 minutes and stirred at 90° C. for 10 hours with the tube sealed. After cooling to room temperature, the reaction mixture was diluted with ethyl acetate (100 mL) and washed with saturated NaHCO$_3$ aqueous solution, H$_2$O and brine. The organic phase was dried over Na$_2$SO$_4$ and concentrated to dryness by rotary evaporation. The crude product was purified with reverse phase HPLC to give N-((2'-fluoro-2,4'-bipyridin-5-yl)methyl)-5-(3-(methylsulfonyl)phenyl)picolinamide 43 as a white powder. MS m/z 463.10 (M+1); $^1$H NMR 400 MHz (DMSO-d$_6$) δ 9.63 (t, 1H, J=6.0 Hz), 9.06 (d, 1H, J=1.6 Hz), 8.75 (d, 1H, J=1.6 Hz), 8.42 (dd, $J_1$=8.4 Hz, $J_2$=2.0 Hz), 8.35 (d, 1H, J=5.2 Hz), 8.31 (m, 1H), 8.20-8.15 (m, 3H), 8.03-8.01 (m, 2H), 7.94 (dd, 1H, $J_1$=8.2 Hz, $J_2$=2.0 Hz), 7.85-7.80 (m, 2H), 4.62 (d, 2H, J=6.4 Hz), 3.30 (s, 3H).

Example 18

N-((2'-fluoro-[2,4'-bipyridin]-5-yl)methyl)-2-oxo-2H-[1,3'-bipyridine]-6'-carboxamide (44)

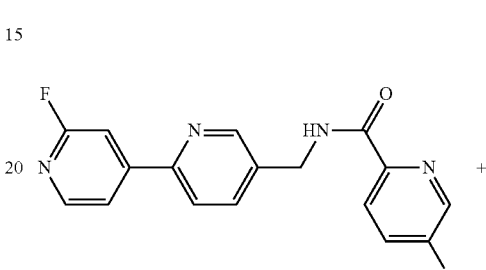

38-4

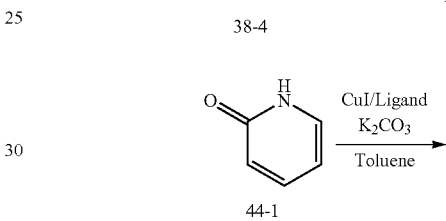

44-1

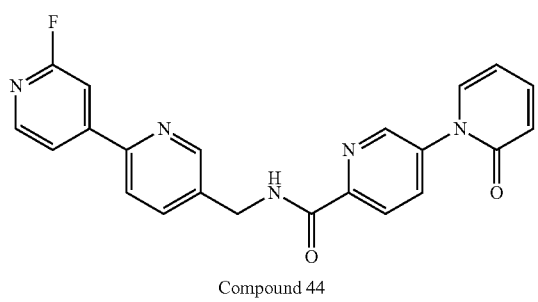

Compound 44

Ligand:

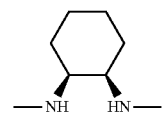

A mixture of 5-bromo-N-42'-fluoro-[2,4'-bipyridin]-5-yl)methyl)picolinamide 38-4 (38.6 mg, 0.1 mmol), 2-hydroxypyridine 44-1 (19.0 mg, 0.2 mmol), CuI (9.5 mg, 0.05 mmol), trans-N1,N2-dimethylcyclohexane-1,2-diamine (7.1 mg, 0.05 mmol) and K$_2$CO$_3$ (28 mg, 0.20 mmol) in toluene (0.6 mL) was stirred at 108° C. for 8 hours. After cooling to room temperature, the mixture was filtered through celite (washed with ethyl acetate) and the filtrate was concentrated with rotavap. The residue was subjected to preparative reverse phase HPLC separation to give N-42'-fluoro-[2,4'-bipyridin]-5-yl)methyl)-2-oxo-2H-[1,3'-bipyridine]-6'-carboxamide 44 as a solid.

Example 19

6-(4-Acetylpiperazin-1-yl)-N-((3-fluoro-2'-(trifluoromethyl)-[2,4'-bipyridin]-5-yl)methyl)nicotinamide (46)

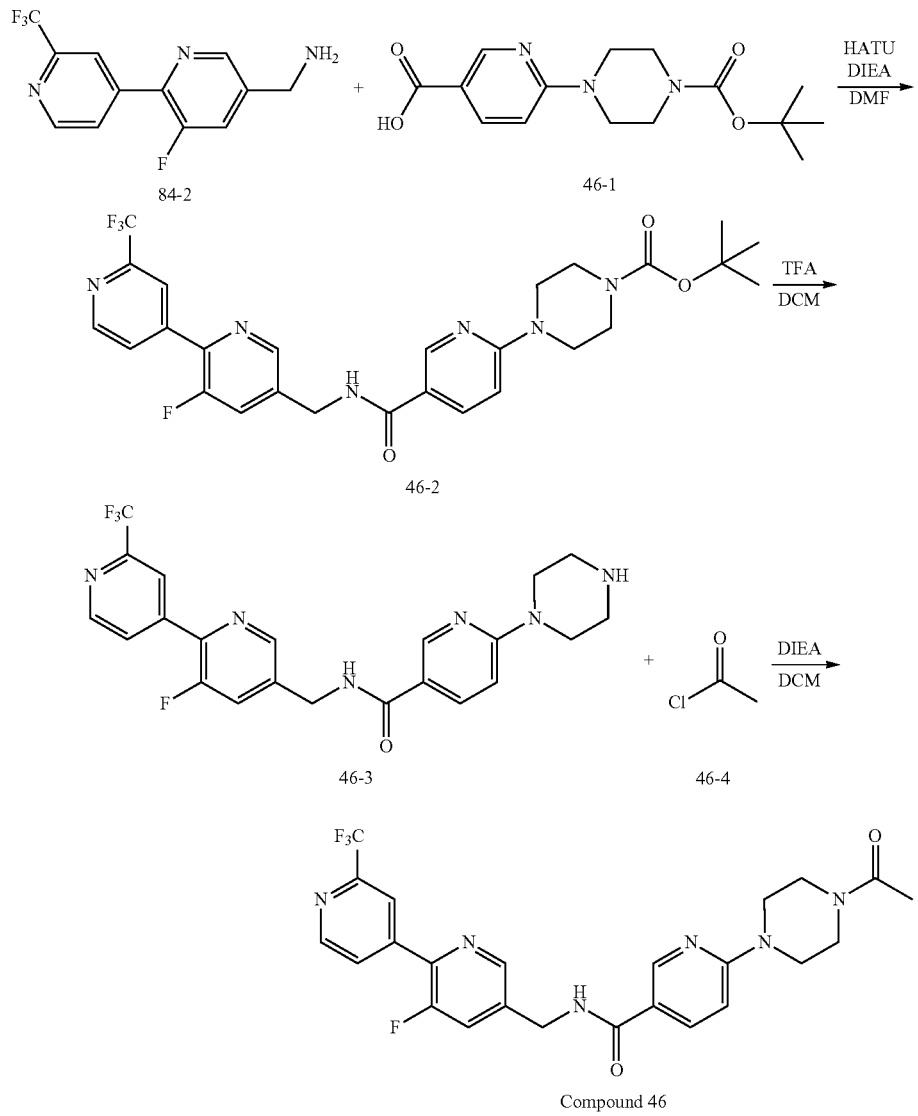

Compound 46

Step 1: To a mixture of (3-fluoro-2'-(trifluoromethyl)-[2,4'-bipyridin]-5-yl)methanamine 84-2 (53 mg, 0.195 mmol), 6-(4-(tert-butoxycarbonyl)piperazin-1-yl)nicotinic acid 46-1 (16 mg, 0.195 mmol), and HATU (81.5 mg, 0.214 mmol) were added N,N-diisopropylethylamine (DIEA, 52 μL, 0.298 mmol) and DMF (1.0 mL). The solution was stirred overnight at room temperature and was subjected to silica gel column chromatography with 1:1 ethyl acetate/hexanes as eluent to give tert-butyl 4-(5-(((3-fluoro-2'-(trifluoromethyl)-[2,4'-bipyridin]-5-yl)methyl)carbamoyl)pyridin-2-yl)piperazine-1-carboxylate 46-2.

Step 2: To a solution of the tert-butyl 4-(5-(((3-fluoro-2'-(trifluoromethyl)-[2,4'-bipyridin]-5-yl)methyl)carbamoyl)pyridin-2-yl)piperazine-1-carboxylate 46-2 in DCM (3.0 mL) was added trifluoroacetic acid (1.0 mL) and the solution was stirred overnight. The reaction mixture was concentrated, redistributed between ethyl acetate and 5% $Na_2CO_3$ solution and the organic phase dried over $Na_2SO_4$. Concentration with rotavap gave crude N-((3-fluoro-2'-(trifluoromethyl)-[2,4'-bipyridin]-5-yl)methyl)-6-(piperazin-1-yl)nicotinamide 46-3.

Step 3: To a solution of N-((3-fluoro-2'-(trifluoromethyl)-[2,4'-bipyridin]-5-yl)methyl)-6-(piperazin-1-yl)nicotinamide 46-3 (35 mg, 0.076 mmol) and DIEA (27 μL, 0.155 mmol) in DCM (1.0 mL) was added acetyl chloride 46-4 (7 μL, 0.095 mmol). After 20 minutes stirring, the mixture was diluted with ethyl acetate, washed with water, and dried over $Na_2SO_4$. After evaporation of the solvents followed by preparative reverse phase HPLC separation gave 6-(4-acetylpiperazin-1-yl)-N-((3-fluoro-2'-(trifluoromethyl)-[2,4'-bipyridin]-5-yl)methyl)nicotinamide as a solid 46. MS m/z 503.2 (M+1). $^1$H NMR 400 MHz ($CDCl_3$) δ 8.76 (d, 1H), 8.58 (d, 1H), 8.54-8.50 (m, 1H), 8.29 (bs, 1H), 8.07 (d, 1H), 7.97 (dd, 1H), 7.60 (dd, 1H), 6.62 (d, 1H), 4.63 (s, 2H), 3.72-3.65 (m, 4H), 3.61-3.55 (m, 4H), 2.10 (s, 3H).

Example 20

5-(4-Acetylpiperazin-1-yl)-N-((3-methyl-2'-(trifluoromethyl)-2,4'-bipyridin-5-yl)methyl)picolinamide (48)

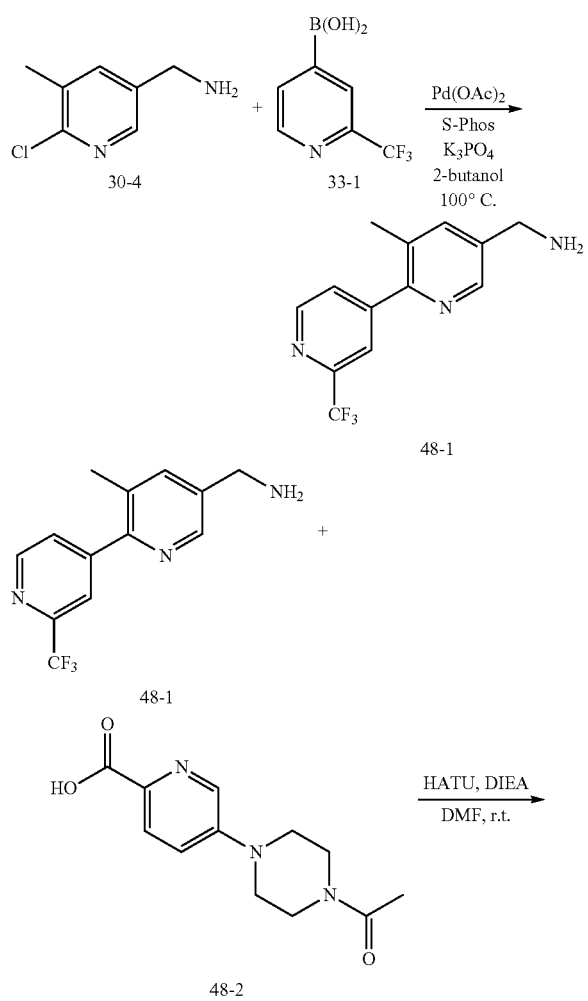

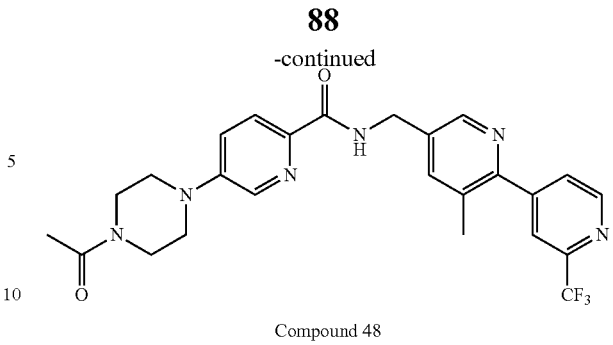

Compound 48

Step 1: To a flask containing (6-chloro-5-methylpyridin-3-yl)methanamine 30-4 (500 mg, 2.20 mmol), 2-(trifluoromethyl)pyridin-4-ylboronic acid 33-1 (418 mg, 2.20 mmol), Pd(OAc)$_2$ (29 mg, 0.11 mmol), S-Phos (91 mg, 0.22 mmol) and potassium phosphate (1.40 g, 6.60 mmol) under Argon was added 2-butanol (4 mL). The mixture was stirred at 100° C. for 10 hours. After cooling to room temperature, the mixture was filtered through celite cake. The filtrate was diluted with ethyl acetate, washed with H$_2$O and brine, dried over Na$_2$SO$_4$, and concentrated to dryness by rotary evaporation. The crude product was purified by silica gel flash chromatography, and eluted with 5% methanol containing ~7N ammonia in dichloromethane to give (2'-(trifluoromethyl)-2,4'-bipyridin-5-yl)methanamine 48-1 as a dark yellow solid. MS m/z 268.1 (M+1)

Step 2: To a mixture of (2'-(trifluoromethyl)-2,4'-bipyridin-5-yl)methanamine 48-1 (27 mg, 0.10 mmol), 5-(4-acetylpiperazin-1-yl)picolinic acid 48-2 (25 mg, 0.10 mmol) and HATU (38 mg, 0.10 mmol) in DMF (0.6 mL) was added DIEA (0.08 mL, 0.50 mmol). The mixture was stirred at room temperature for 2 hours. The solvent was removed by rotary evaporation. The crude product was purified by reverse phase HPLC to give 5-(4-acetylpiperazin-1-yl)-N-((3-methyl-2'-(trifluoromethyl)-2,4'-bipyridin-5-yl)methyl)picolinamide 48 as a white powder. MS m/z 499.20 (M+1); $^1$H NMR 400 MHz (DMSO-d$_6$) δ 9.20 (t, 1H, J=6.4 Hz), 8.86 (d, 1H, J=5.2 Hz), 8.53 (m, 1H), 8.32 (d, 1H, J=2.8 Hz), 8.04 (s, 1H), 7.93-7.86 (m, 2H), 7.72 (m, 1H), 7.43 (dd, 1H, J$_1$=8.8 Hz, J$_2$=2.8 Hz), 4.52 (d, 2H, J=6.4 Hz), 3.60-3.58 (m, 4H), 3.41-3.38 (m, 4H), 2.36 (s, 3H), 2.05 (s, 3H).

Example 21

Methyl 4-(6-((3-fluoro-2'-(trifluoromethyl)-2,4'-bipyridin-5-yl)methylcarbamoyl)pyridin-3-yl)piperazine-1-carboxylate (49)

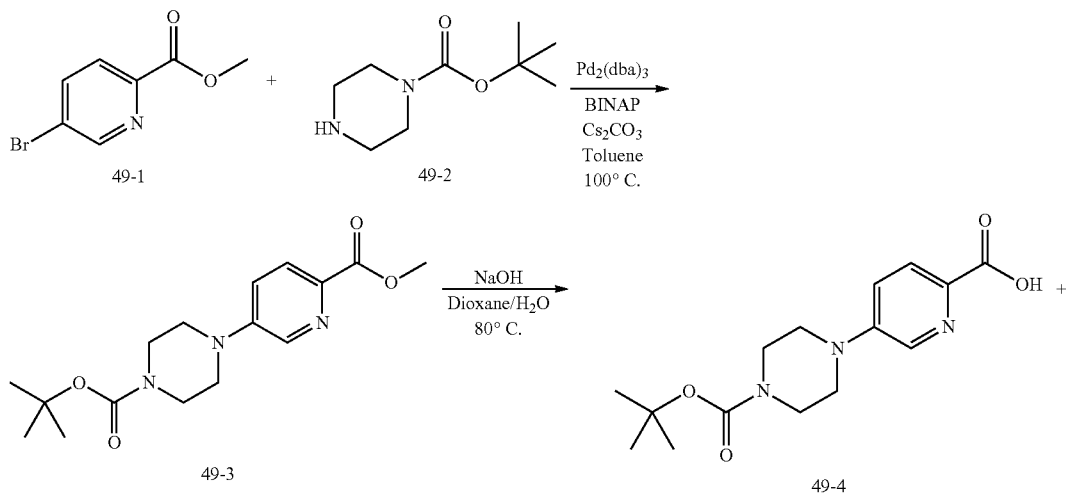

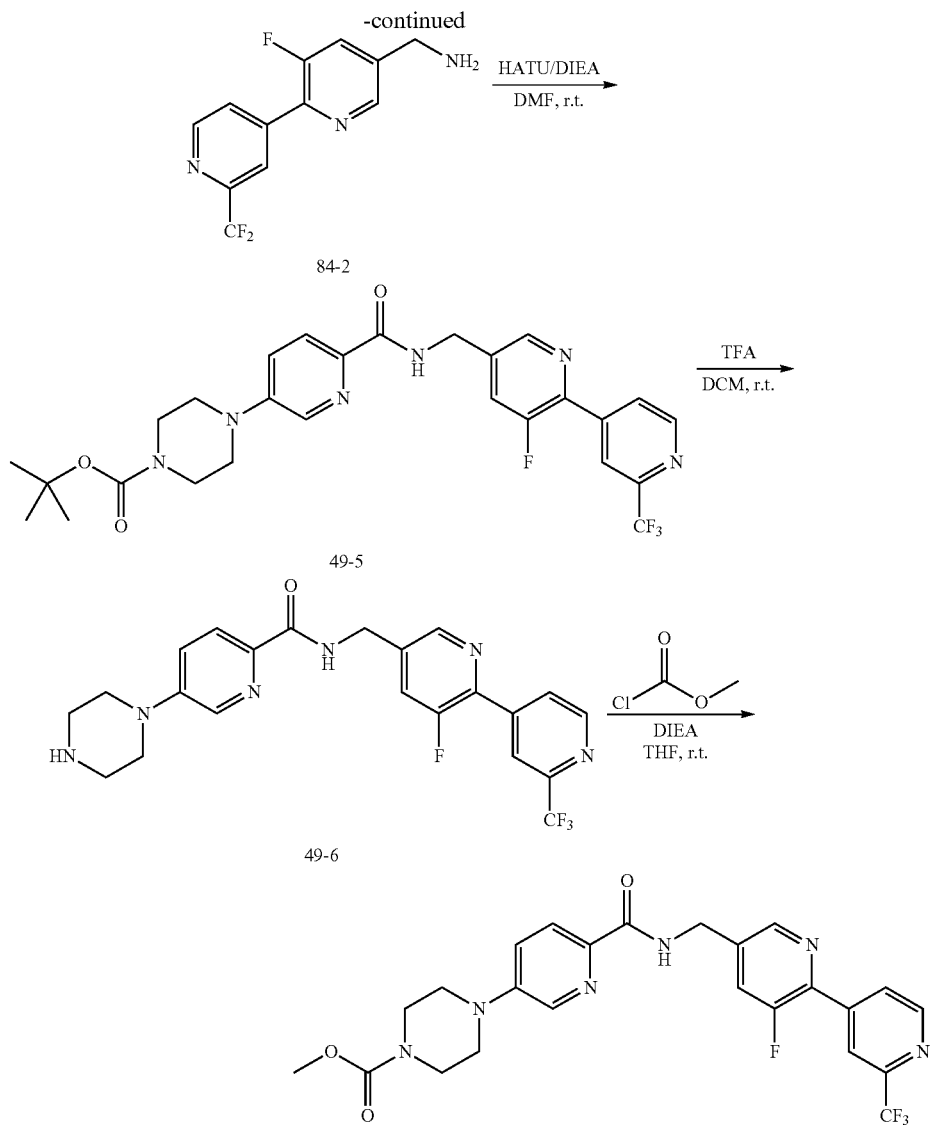

Step 1: To a flask containing methyl 5-bromopicolinate 49-1 (1.48 g, 6.85 mmol), tert-butyl piperazine-1-carboxylate 49-2 (1.53 g, 8.22 mmol), Pd$_2$(dba)$_3$ (315 mg, 0.34 mmol), BINAP (462 mg, 0.69 mmol) and Cs$_2$CO$_3$ (5.50 g, 17.20 mmol) under argon was added anhydrous toluene (30 mL). The mixture was stirred at 100° C. for 10 hours. After cooling to room temperature, the solvent was removed by rotary evaporation. The residue was redissolved in ethyl acetate (100 mL), washed with H$_2$O and brine, dried over Na$_2$SO$_4$, and concentrated to dryness by rotary evaporation. The crude product was purified by silica gel flash chromatography, eluted with 5% methanol in dichloromethane to give tert-butyl 4-(6-(methoxycarbonyl)pyridin-3-yl)piperazine-1-carboxylate 49-3 as a yellow solid. MS m/z 322.1 (M+1)

Step 2: A mixture of tert-butyl 4-(6-(methoxycarbonyl)pyridin-3-yl)piperazine-1-carboxylate 49-3 (1.93 g, 6.01 mmol) and NaOH (530 mg, 13.26 mmol) in dioxane (15 mL) and H$_2$O (15 mL) was stirred at 80° C. for 2 hours. Dioxane was removed by rotary evaporation and the resulting solution was acidified to pH around 4 by 1N HCl aqueous solution, followed by extraction with ethyl acetate (60 mL×3). The combined organic layers were washed with H$_2$O and brine, dried over Na$_2$SO$_4$, and concentrated to dryness by rotary evaporation to afford 5-(4-(tert-butoxycarbonyl)piperazin-1-yl)picolinic acid 49-4 as a yellow solid. MS m/z 308.1 (M+1)

Step 3: To a mixture of 5-(4-(tert-butoxycarbonyl)piperazin-1-yl)picolinic acid 49-4 (92 mg, 0.3 mmol), (3-fluoro-2'-(trifluoromethyl)-2,4'-bipyridin-5-yl)methanamine 84-2 (81 mg, 0.3 mmol) and HATU (114 mg, 0.3 mmol) in DMF (1.5 mL) was added DIEA (0.15 mL, 0.9 mmol). The mixture was stirred at room temperature for 2 hours. The mixture was diluted with ethyl acetate (100 mL), washed with H$_2$O and brine, dried over Na$_2$SO$_4$, and concentrated to dryness by rotary evaporation. The crude product was purified by silica gel flash chromatography, and eluted with 5% methanol in dichloromethane to give tert-butyl 4-(6-((3-fluoro-2'-(trifluoromethyl)-2,4'-bipyridin-5-yl)methylcarbamoyl)pyridin-3-yl)piperazine-1-carboxylate 49-5 as a pale yellow oil. MS m/z 561.2 (M+1)

Step 4: To a solution of tert-butyl 4-(6-((3-fluoro-2'-(trifluoromethyl)-2,4'-bipyridin-5-yl)methylcarbamoyl)pyridin- 3-yl)piperazine-1-carboxylate 49-5 (106 mg, 0.21 mmol) in dichloromethane (2 mL) was added TFA (1 mL) dropwise. The mixture was stirred at room temperature for 2 hours, and the solvents were removed by rotary evaporation. The residue was dissolved in ethyl acetate (100 mL), washed with saturated aqueous NaHCO$_3$ solution, H$_2$O and brine, dried over Na$_2$SO$_4$ and concentrated to dryness by rotary evaporation to give N-((3-fluoro-2'-(trifluoromethyl)-2,4'-bipyridin-5-yl)methyl)-5-(piperazin-1-yl)picolinamide 49-6 as yellow solid. MS m/z 461.2 (M+1)

Step 5: To a solution of N-((3-fluoro-2'-(trifluoromethyl)-2,4'-bipyridin-5-yl)methyl)-5-(piperazin-1-yl)picolinamide 49-6 (64 mg, 0.14 mmol) and DIEA (0.07 mL, 0.42 mmol) in THF (1 mL) was added methyl chloroformate (13 uL, 0.17 mmol) dropwise at room temperature. The mixture was stirred for 2 hours. The solvent was removed by rotary evaporation. The crude product was purified by reverse phase HPLC to give methyl 4-(6-((3-fluoro-2'-(trifluoromethyl)-2,4'-bipyridin-5-yl)methylcarbamoyl)pyridin-3-yl)piperazine-1-carboxylate 93 as a white powder. MS m/z 519.20 (M+1); $^1$H NMR 400 MHz (DMSO-d$_6$) δ 9.28 (t, 1H, J=6.4 Hz), 8.92 (d, 1H, J=5.2 Hz), 8.62 (m, 1H), 8.32 (m, 2H), 8.20 (d, 1H, J=5.2 Hz), 7.88-7.82 (m, 2H), 7.43 (dd, 1H, J$_1$=7.0 Hz, J$_2$=3.2 Hz), 4.59 (d, 2H, J=6.4 Hz), 3.73 (s, 3H), 3.54-3.51 (m, 4H), 3.37-3.35 (m, 4H).

Example 22

N-((3-Methyl-2'-(trifluoromethyl)-2,4'-bipyridin-5-yl)methyl)-5-(pyrazin-2-yl)picolinamide (55)

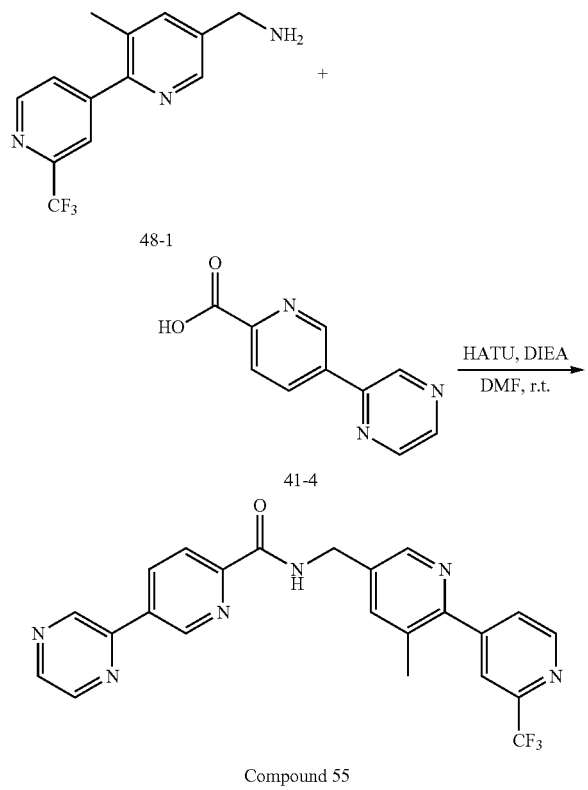

Compound 55

To a mixture of (2'-(trifluoromethyl)-2,4'-bipyridin-5-yl)methanamine 48-1 (27 mg, 0.10 mmol), 5-(pyrazin-2-yl)picolinic acid 41-4 (21 mg, 0.10 mmol) and HATU (38 mg, 0.10 mmol) in DMF (0.6 mL) was added DIEA (0.05 mL, 0.30 mmol). The mixture was stirred at room temperature for 2 hours. The solvent was removed by rotary evaporation. The crude product was purified by reverse phase HPLC to give N-((3-methyl-2'-(trifluoromethyl)-2,4'-bipyridin-5-yl)methyl)-5-(pyrazin-2-yl)picolinamide 55 as a white powder. MS m/z 451.20 (M+1); $^1$H NMR 400 MHz (DMSO-d$_6$) δ 9.67 (t, 1H, J=6.0 Hz), 9.45 (d, 1H, J=1.2 Hz), 9.40 (d, 1H, J=0.8 Hz), 8.87-8.82 (m, 2H), 8.74-8.57 (m, 2H), 8.57 (m, 1H), 8.20 (d, 1H, J=8.4 Hz), 8.05 (m, 1H), 7.93 (dd, 1H, J$_1$=9.6 Hz, J$_2$=1.2 Hz), 7.77 (m, 1H), 4.59 (d, 2H, J=6.0 Hz), 2.38 (s, 3H).

Example 23

N-((2-oxo-1-(2-(trifluoromethyl)pyridin-4-yl)-1,2-dihydropyridin-4-yl)methyl)-5-(pyrazin-2-yl)picolinamide (56)

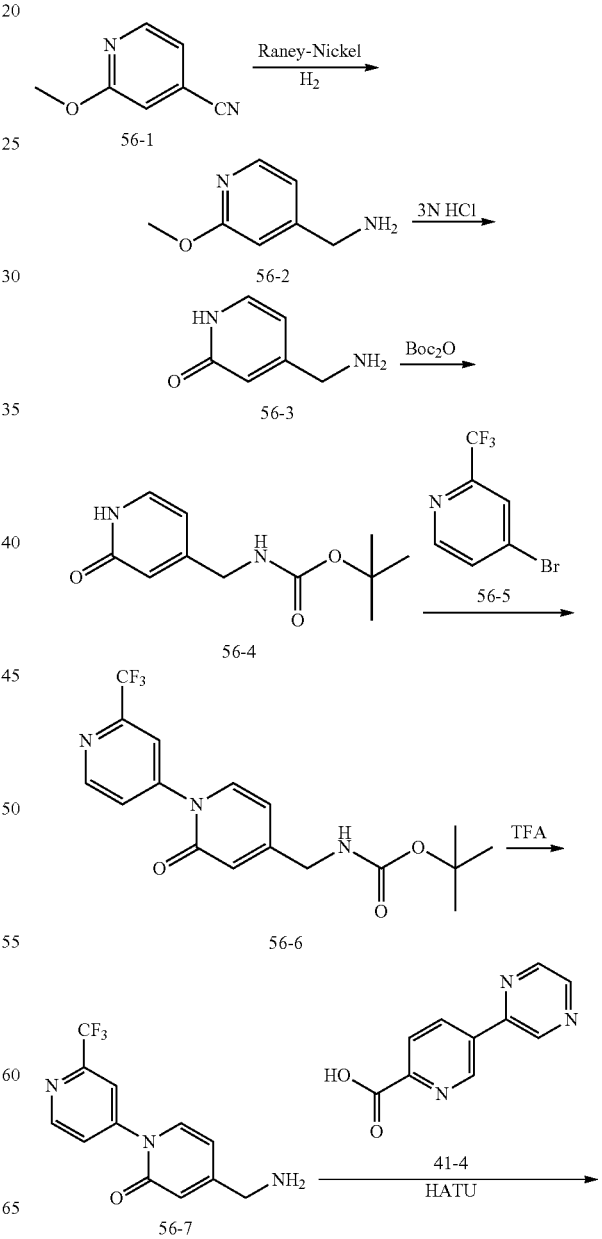

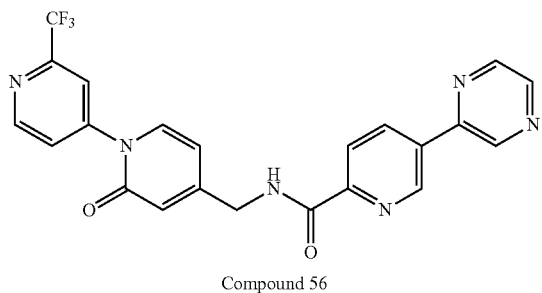

Compound 56

Step 1: To the solution of 2-methoxyisonicotinonitrile 56-1 (1.1 g, 8.2 mmol) in methanol with 7 N $NH_3$ was added Raney-Nickel (1.0 g). The reaction was shaken under $H_2$ at 50 psi at room temperature in Parr shaker for 12 hours. The Raney-Nickel was removed by rotary evaporation and the filtrate was taken to dryness by rotary evaporation to give crude (2-methoxypyridin-4-yl)methanamine 56-2. MS m/z 139.2 (M+1).

Step 2: The starting material (2-methoxypyridin-4-yl)methanamine 56-2 in 3N HCl was refluxed at 110° C. for 12 hours. The reaction was taken to dryness by rotary evaporation to give crude 4-(aminomethyl)pyridin-2(1H)-one 56-3.

Step 3: To the solution of 4-(aminomethyl)pyridin-2(1H)-one 56-3 in dioxane (25 mL) was added 1N NaOH (25 mL) and $Boc_2O$ (1.78 g, 8.1 mmol) subsequently. The reaction was stirred at room temperature for 12 hours. The reaction was neutralized with 1N $NaHSO_4$ followed by extraction with ethyl acetate 4 times. The organic phase was combined and dried. The crude product was purified by silica gel flash chromatography, eluted with 5% methanol in DCM to give tert-butyl (2-oxo-1,2-dihydropyridin-4-yl)methylcarbamate 56-4 as a white solid. MS m/z 225.2 (M+1).

Step 4: To a reaction vessel containing a stir bar was charged with tert-butyl (2-oxo-1,2-dihydropyridin-4-yl)methylcarbamate 56-4 (72 mg, 0.32 mmol), CuI (12 mg, 0.06 mmol), and $K_2CO_3$ (88 mg, 0.64 mmol). The reaction vessel was evacuated and backfilled with nitrogen. A solution of 4-bromo-2-(trifluoromethyl)pyridine 56-5 (94 mg, 0.42 mmol) and (1R,2R)—$N^1,N^2$-dimethylcyclohexane-1,2-diamine (9 mg, 0.06 mmol) in toluene (3 mL) was added via syringe. The reaction was stirred at room temperature for 20 minutes, then 110° C. overnight. The reaction mixture was diluted into ethyl acetate and filtered through celite pad to remove salt. The filtrate was dried and the residue was purified by silica gel flash chromatography, and eluted with 50% ethyl acetate to give tert-butyl (2-oxo-1-(2-(trifluoromethyl)pyridin-4-yl)-1,2-dihydropyridin-4-yl)methylcarbamate 56-6. MS m/z 370.2 (M+1).

Step 5: To the solution of tert-butyl (2-oxo-1-(2-(trifluoromethyl)pyridin-4-yl)-1,2-dihydropyridin-4-yl)methylcarbamate 56-6 (95 mg, 0.26 mmol) in DCM (2 mL) was added TFA (2 mL) at room temperature. The reaction was stirred at room temperature for 30 minutes. The solvent and TFA was removed by rotary evaporation to give crude 4-(aminomethyl)-1-(2-(trifluoromethyl)pyridin-4-yl)pyridin-2(1H)-one 56-7. MS m/z 270.2 (M+1).

Step 6: To a mixture of 5-(pyrazin-2-yl)picolinic acid 41-4 (28 mg, 0.14 mmol), 4-(aminomethyl)-1-(2-(trifluoromethyl)pyridin-4-yl)pyridin-2(1H)-one 56-7 (35 mg, 0.13 mmol) and O-(7-azabenzotriazol-1-yl)-N,N,N',N'-tetramethyluronium-hexafluorophosphate (HATU) (49 mg, 0.13 mmol) in DMF (1.0 mL) was added DIEA (0.09 mL, 0.52 mmol) at room temperature. The mixture was stirred at room temperature for 2 hours. The reaction mixture was diluted into DMSO and purified by HPLC to give N-((2-oxo-1-(2-(trifluoromethyl)pyridin-4-yl)-1,2-dihydropyridin-4-yl)methyl)-5-(pyrazin-2-yl)picolinamide 56 as a white solid. MS m/z 453.2 (M+1). $^1$H NMR 400 MHz (DMSO-$d_6$) δ 9.57 (t, 1H), 9.40 (d, 1H), 9.36 (dd, 1H), 8.86 (d, 1H), 8.77 (dd, 1H), 8.69 (m, 2H), 8.16 (dd, 1H), 8.07 (d, 1H), 7.84 (dd, 1H), 7.73 (d, 1H), 6.37 (dd, 1H), 6.31 (b, 1H), 4.36 (d, 2H).

Example 24

N-((3-Methyl-2'-(trifluoromethyl)-2,4'-bipyridin-5-yl)methyl)-4-(pyrazin-2-yl)benzamide (58)

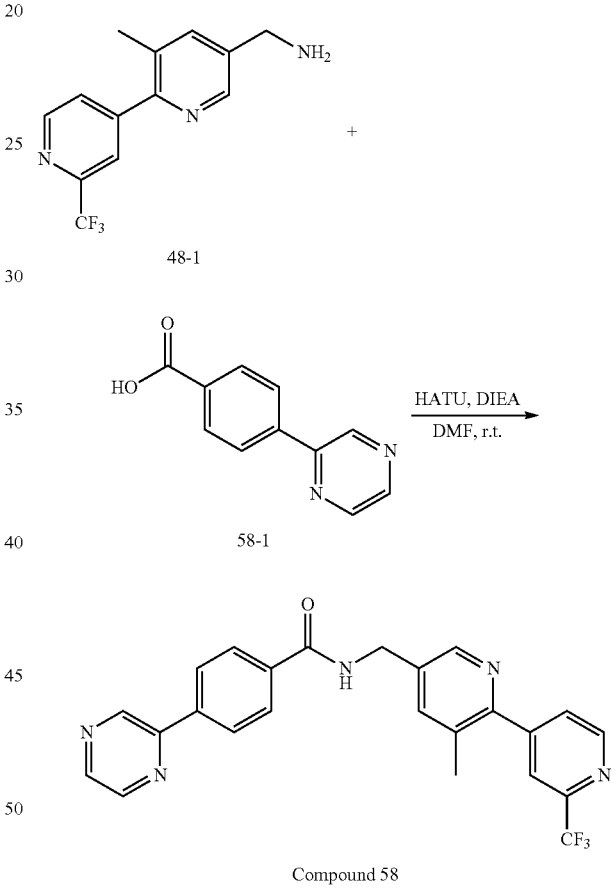

Compound 58

To a mixture of (2'-(trifluoromethyl)-2,4'-bipyridin-5-yl)methanamine 48-1 (40 mg, 0.15 mmol), 4-(pyrazin-2-yl)benzoic acid 58-1 (30 mg, 0.15 mmol) and HATU (57 mg, 0.15 mmol) in DMF (0.9 mL) was added DIEA (0.08 mL, 0.45 mmol). The mixture was stirred at room temperature for 2 hours. The solvent was removed by rotary evaporation. The crude product was purified by reverse phase HPLC to give N-((3-methyl-2'-(trifluoromethyl)-2,4'-bipyridin-5-yl)methyl)-4-(pyrazin-2-yl)benzamide 58 as a white powder. MS m/z 450.20 (M+1); $^1$H NMR 400 MHz (DMSO-$d_6$) δ 9.35 (d, 1H, J=1.6 Hz), 9.30 (t, 1H, J=6.0 Hz), 8.86 (d, 1H, J=4.8 Hz), 8.76 (m, 1H), 8.67 (d, 1H, J=2.4 Hz), 8.57 (m, 1H), 8.30-8.27

(m, 2H), 8.08-8.06 (m, 3H), 7.94 (dd, 1H, $J_1$=5.0 Hz, $J_2$=1.2 Hz), 7.77 (m, 1H), 4.85 (d, 2H, J=6.0 Hz), 2.40 (s, 3H).

Example 25

N-((2',3-dimethyl-2,4'-bipyridin-5-yl)methyl)-5-(pyrazin-2-yl)picolinamide (63)

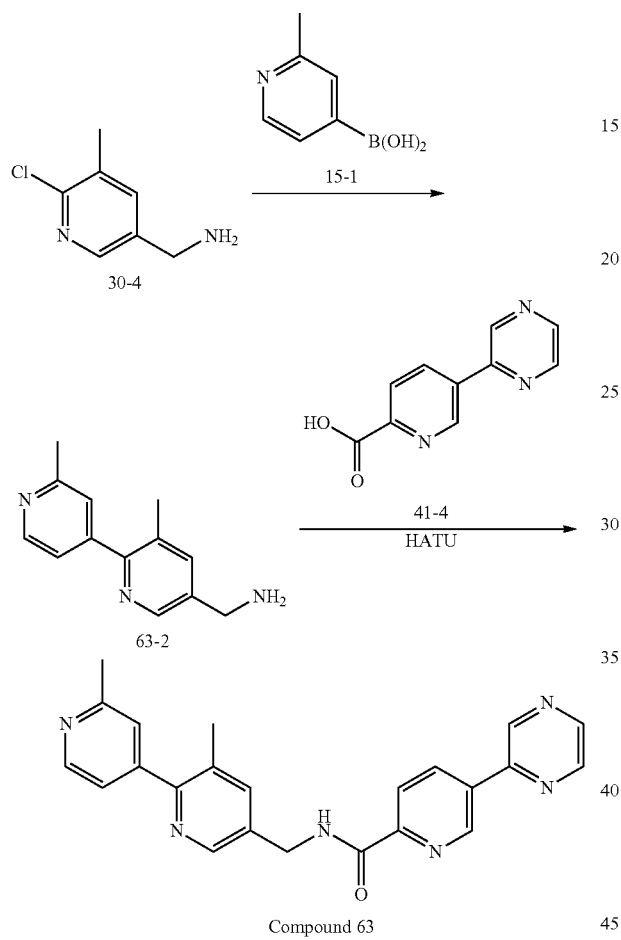

Step 1: To a reaction vial was added (6-chloro-5-methylpyridin-3-yl)methanamine 30-4 (500 mg, 2.6 mmol), 2-methylpyridin-4-ylboronic acid 15-1 (460 mg, 3.38 mmol), Pd(OAc)$_2$ (58 mg, 0.26 mmol), S-Phos (150 mg, 0.37 mmol) and K$_3$PO$_4$ (1.65 g, 7.8 mmol). The vial was evacuated and backfilled with nitrogen. 2-butanol (5 mL) was added via syringe. The reaction was stirred at room temperature for 10 mins and then 110° C. for 2 hours. After cooling to room temperature, the reaction mixture was diluted into 10% methanol in DCM, and filtered through celite pad. The filtrate was dried and the crude product was purified by silica gel flash chromatography, and eluted with 10% methanol in DCM to give (2',3-dimethyl-2,4'-bipyridin-5-yl)methanamine 63-2 as an oil. MS m/z 214.2 (M+1).

Step 2: To a mixture of 5-(pyrazin-2-yl)picolinic acid 41-4 (20 mg, 0.1 mmol), (2',3-dimethyl-2,4'-bipyridin-5-yl) methanamine 63-2 (21 mg, 0.1 mmol) and O-(7-azabenzotriazol-1-yl)-N,N,N',N'-tetramethyluroniumhexafluorophosphate (HATU) (38 mg, 0.1 mmol) in DMF (1.0 mL) was added DIEA (0.053 mL, 0.3 mmol) at room temperature. The mixture was stirred at room temperature for 2 hours. The reaction mixture was diluted into DMSO and purified by HPLC to give N-((2',3-dimethyl-2,4'-bipyridin-5-yl)methyl)-5-(pyrazin-2-yl)picolinamide 63 as white solid. MS m/z 397.2 (M+1). $^1$H NMR 400 MHz (DMSO-d$_6$) δ 9.59 (t, 1H), 9.39 (d, 1H), 9.33 (d, 1H), 8.76 (m, 1H), 8.68 (m, 2H), 8.45 (d, 1H), 8.15 (d, 1H), 7.65 (d, 1H), 7.34 (b, 1H), 7.27 (d, 1H), 4.51 (d, 2H), 2.46 (s, 3H), 2.26 (s, 3H).

Example 26

N-((5-Methyl-6-(2-oxo-1,2-dihydropyridin-4-yl) pyridin-3-yl)methyl)-5-(pyrazin-2-yl)picolinamide (66)

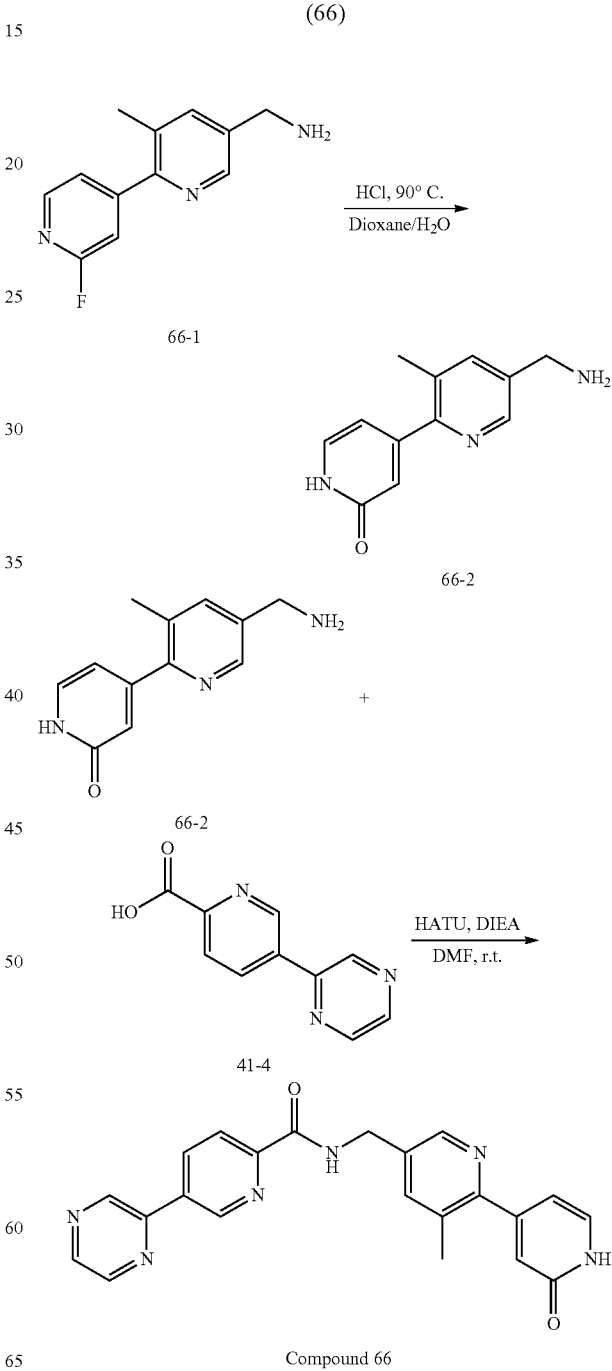

Step 1: To a mixture of (2'-fluoro-3-methyl-2,4'-bipyridin-5-yl)methanamine 66-1 (65 mg, 0.30 mmol) in dioxane (0.6 mL) and H₂O (0.2 mL) was added a few drops of aqueous concentrated HCl solution. The mixture was stirred at 90° C. for 10 hours, and then concentrated to dryness by rotary evaporation to give 4-(5-(aminomethyl)-3-methylpyridin-2-yl)pyridin-2(1H)-one 66-2 as yellow solid.

Step 2: To a mixture of 4-(5-(aminomethyl)-3-methylpyridin-2-yl)pyridin-2(1H)-one 66-2,5-(pyrazin-2-yl)picolinic acid 41-4 (42 mg, 0.20 mmol) and HATU (76 mg, 0.20 mmol) in DMF (0.9 mL) was added DIEA (0.2 mL, 1.20 mmol). The mixture was stirred at room temperature for 2 hours. The solvent was removed by rotary evaporation. The crude product was purified by reverse phase HPLC to give N-((5-methyl-6-(2-oxo-1,2-dihydropyridin-4-yl)pyridin-3-yl)methyl)-5-(pyrazin-2-yl)picolinamide 66 as a white powder. MS m/z 399.20 (M+1); $^1$H NMR 400 MHz (DMSO-d₆) δ 9.62 (t, 1H, J=6.4 Hz), 9.45 (d, 1H, J=1.6 Hz), 9.39 (m, 1H), 8.83-8.82 (m, 1H), 8.74-8.70 (m, 2H), 8.47 (m, 1H), 8.20 (dd, 1H, J₁=8.2 Hz, J₂=0.4 Hz), 7.68 (m, 1H), 7.42 (d, 1H, J=6.8 Hz), 4.55 (d, 2H, J=6.4 Hz), 2.31 (s, 3H).

Example 27

6'-(2-Oxopyrrolidin-1-yl)-N-((2'-(trifluoromethyl)-[2,4'-bipyridin]-5-yl)methyl)-[3,3'-bipyridine]-6-carboxamide (72)

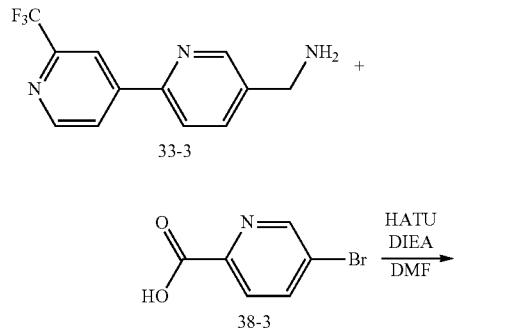

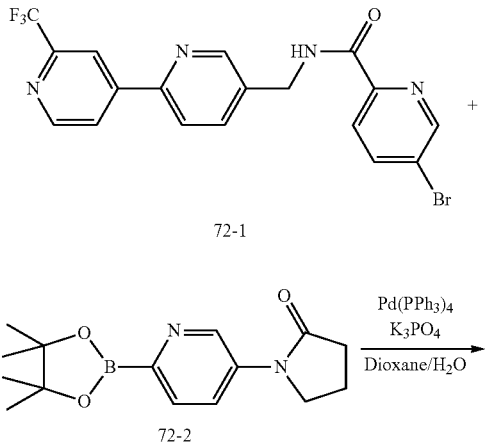

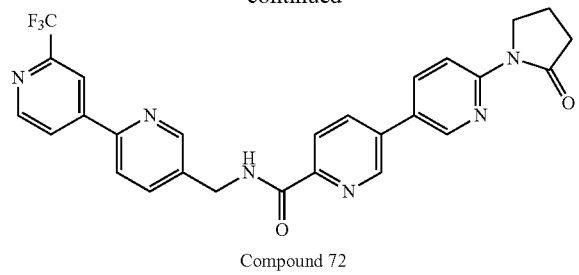

Compound 72

Step 1: To a mixture of (2'-(trifluoromethyl)-[2,4'-bipyridin]-5-yl)methanamine 33-3 (105 mg, 0.39 mmol), 5-bromopicolinic acid 38-3 (83 mg, 0.41 mmol), and HATU (164 mg, 0.43 mmol) were added N,N-diisopropylethylamine (DIEA, 103 μL, 0.59 mmol) and DMF (2.0 mL). After stirring at room temperature 4 hours, the mixture was diluted with ethyl acetate (60 mL) and washed with water (2×50 mL). The organic phase was dried over Na₂SO₄ and concentrated with rotavap. The residue was subjected to silica gel column chromatography with 1:2 hexanes/ethyl acetate as eluent to give 5-bromo-N-((2'-(trifluoromethyl)-[2,4'-bipyridin]-5-yl)methyl)picolinamide 72-1.

Step 2: A mixture of 5-bromo-N-((2'-(trifluoromethyl)-[2,4'-bipyridin]-5-yl)methyl)picolinamide 72-1 (22 mg, 0.05 mmol), 1-(5-(4,4,5,5-tetramethyl-1,3,2-dioxaborolan-2-yl)pyridin-2-yl)pyrrolidin-2-one 72-2 (29 mg, 0.1 mmol), Pd(PPh₃)₄ (12 mg, 0.01 mmol) and K₃PO₄ (21 mg, 0.1 mmol) in dioxane (0.5 mL) and water (0.1 mL) was stirred at 96° C. under argon overnight. After cooling to room temperature, the mixture was filtered through celite (washed with ethyl acetate) and the filtrate was redistributed between ethyl acetate and water. The organic phase was dried over Na₂SO₄ and concentrated with rotavap. The residue was subjected to preparative reverse phase HPLC separation to give 6'-(2-oxopyrrolidin-1-yl)-N-((2'-(trifluoromethyl)-[2,4'-bipyridin]-5-yl)methyl)-[3,3'-bipyridine]-6-carboxamide 72 as a solid. MS m/z 519.2 (M+1). $^1$H NMR 400 MHz (CDCl₃) δ 8.83 (d, 1H), 8.79 (d, 1H), 8.76 (dd, 1H), 8.62 (dd, 1H), 8.57 (dd, 1H), 8.52 (t, 1H), 8.34-8.29 (m, 2H), 8.10-8.02 (m, 2H), 7.96-7.88 (m, 2H), 7.84 (d, 1H), 4.79 (d, 2H), 4.16 (t, 2H), 2.71 (t, 2H), 2.18 (t, 2H).

Example 28

N-((2',5-dimethyl-3,4'-bipyridin-6-yl)methyl)-5-(pyrazin-2-yl)picolinamide (81)

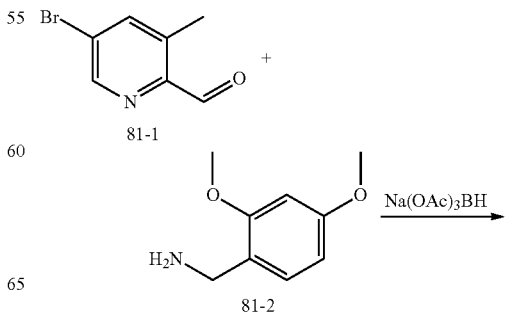

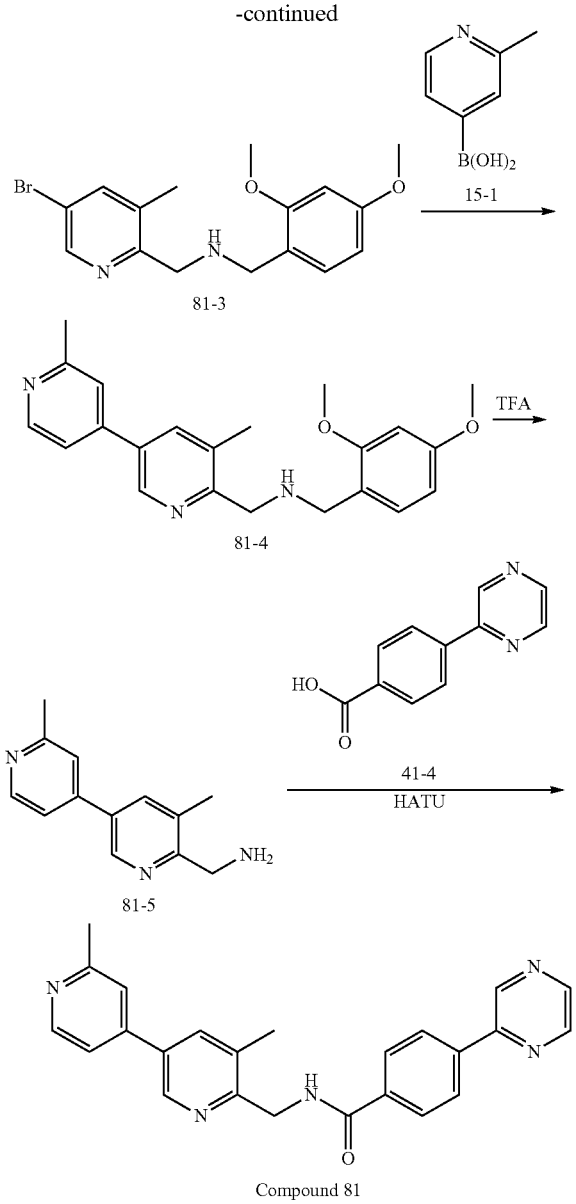

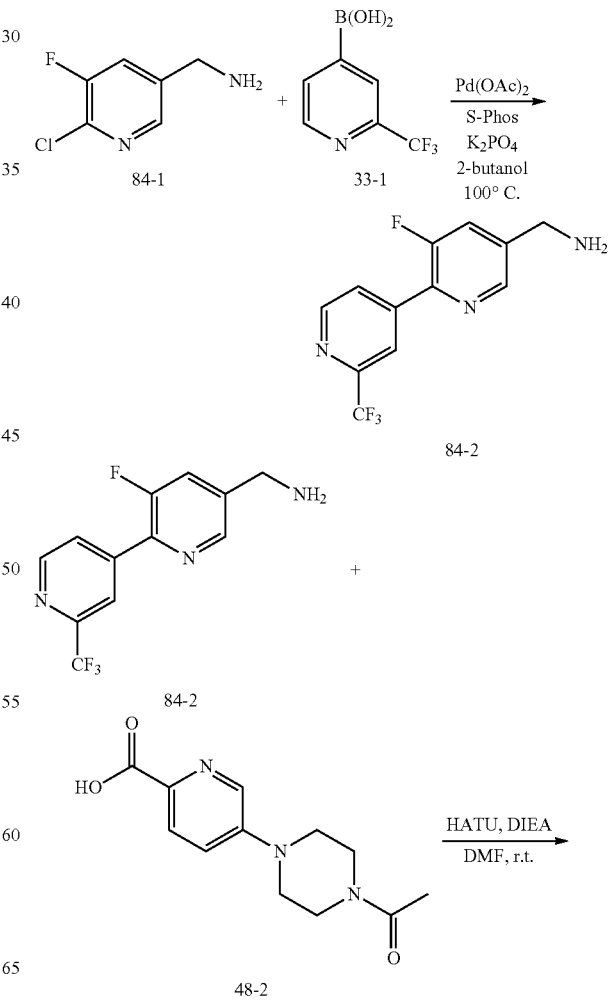

Step 3: To the reaction vessel containing N-(2,4-dimethoxybenzyl)-1-(2',5-dimethyl-3,4'-bipyridin-6-yl)methanamine 81-4 (0.54 g, 1.5 mmol) was added trifluoroacetic acid (2 mL). The reaction was stirred at room temperature for 2 hours. TFA was removed by rotary evaporation to give crude (2',5-dimethyl-3,4'-bipyridin-6-yl)methanamine 81-5. MS m/z 214.2 (M+1).

Step 4: To a mixture of 5-(pyrazin-2-yl)picolinic acid 41-4 (20 mg, 0.1 mmol), (2',5-dimethyl-3,4'-bipyridin-6-yl)methanamine 81-5 (21 mg, 0.1 mmol) and O-(7-azabenzotriazol-1-yl)-N,N,N',N'-tetramethyluroniumhexafluorophosphate (HATU) (38 mg, 0.1 mmol) in DMF (1.0 mL) was added DIEA (0.053 mL, 0.3 mmol) at room temperature. The mixture was stirred at room temperature for 2 hours. The reaction mixture was diluted into DMSO and purified by HPLC to give N-42',5-dimethyl-[3,4'-bipyridin]-6-yl)methyl)-5-(pyrazin-2-yl)picolinamide 81 as a white solid. MS m/z 397.2 (M+1). $^1$H NMR 400 MHz (DMSO-$d_6$) δ 9.60 (t, 1H), 9.54 (d, 1H), 9.52 (d, 1H), 8.99 (d, 1H), 8.91 (m, 1H), 8.82-8.80 (m, 2H), 8.66 (d, 1H), 8.33 (d, 1H), 8.20 (d, 1H), 7.87 (s, 1H), 7.79 (b, 1H), 4.81 (d, 2H), 2.64 (s, 3H), 2.51 (s, 3H).

Example 29

5-(4-Acetylpiperazin-1-yl)-N-((3-fluoro-2'-(trifluoromethyl)-2,4'-bipyridin-5-yl)methyl)picolinamide (84)

Step 1: To the solution of 5-bromo-3-methylpicolinaldehyde 81-1 (1.0 g, 5 mmol), (2,4-dimethoxyphenyl)methanamine 81-2 (0.83 g, 5 mmol), acetic acid (0.9 g, 15 mmol) in DMF (10 mL) was added Na(OAc)$_3$BH (2.46 g, 15 mmol) at room temperature. The reaction was stirred at room temperature overnight. The reaction was diluted with ethyl acetate and washed with aqueous Na$_2$CO$_3$ and brine. The organic phase was dried to give crude 1-(5-bromo-3-methylpyridin-2-yl)-N-(2,4-dimethoxybenzyl)methanamine 81-3. MS m/z 351.2 (M+1).

Step 2: To a round bottom flask was added 1-(5-bromo-3-methylpyridin-2-yl)-N-(2,4-dimethoxybenzyl)methanamine 81-3 (1.5 g, 4.3 mmol), 2-methylpyridin-4-ylboronic acid 15-1 (589 mg, 4.3 mmol), Pd(PPh$_3$)$_4$ (248 mg, 0.22 mmol), saturated Na$_2$CO$_3$ (10 mL), ethanol (10 mL) and toluene (30 mL). The reaction was refluxed at 120° C. for 30 hours. After cooling to room temperature, the reaction was diluted into ethyl acetate and washed with brine. The solvent was removed by rotary evaporation. The crude product was purified by silica gel flash chromatography to give N-(2,4-dimethoxybenzyl)-1-(2',5-dimethyl-3,4'-bipyridin-6-yl)methanamine 81-4. MS m/z 364.2 (M+1).

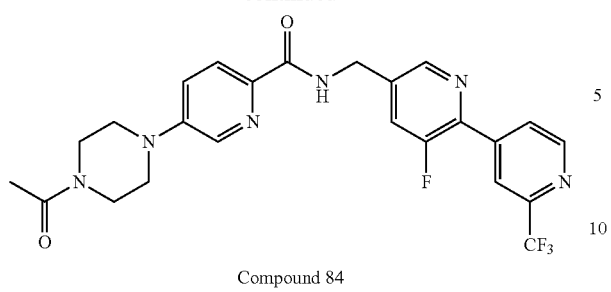

Compound 84

Step 1: To a flask containing (6-chloro-5-fluoropyridin-3-yl)methanamine 84-1 (353 mg, 2.20 mmol), 2-(trifluoromethyl)pyridin-4-ylboronic acid 33-1 (418 mg, 2.20 mmol), Pd(OAc)$_2$ (29 mg, 0.11 mmol), S-Phos (91 mg, 0.22 mmol) and potassium phosphate (1.40 g, 6.60 mmol) under Argon was added 2-butanol (4 mL). The mixture was stirred at 100° C. for 10 hours. After cooling to room temperature, the mixture was filtered through celite cake. The filtrate was diluted with ethyl acetate, washed with H$_2$O and brine, dried over Na$_2$SO$_4$, and concentrated to dryness by rotary evaporation. The crude product was purified by silica gel flash chromatography, and eluted with 5% methanol containing ~7N ammonia in dichloromethane to give (3-fluoro-2'-(trifluoromethyl)-2,4'-bipyridin-5-yl)methanamine 84-2 as a pale yellow solid. MS m/z 268.1 (M+1)

Step 2: To a mixture of (3-fluoro-2'-(trifluoromethyl)-2,4'-bipyridin-5-yl)methanamine 84-2 (54 mg, 0.20 mmol), 5-(4-acetylpiperazin-1-yl)picolinic acid 48-2 (50 mg, 0.20 mmol) and HATU (76 mg, 0.20 mmol) in DMF (0.9 mL) was added DIEA (0.16 mL, 1.00 mmol). The mixture was stirred at room temperature for 2 hours. The solvent was removed by rotary evaporation. The crude product was purified by reverse phase HPLC to give 5-(4-acetylpiperazin-1-yl)-N-((3-fluoro-2'-(trifluoromethyl)-2,4'-bipyridin-5-yl)methyl)picolinamide 84 as a white powder. MS m/z 503.20 (M+1); $^1$H NMR 400 MHz (DMSO-d$_6$) δ 9.28 (t, 1H, J=6.4 Hz), 8.92 (d, 1H, J=5.2 Hz), 8.62 (m, 1H), 8.32 (m, 2H), 8.20 (d, 1H, J=4.8 Hz), 7.88-7.82 (m, 2H), 7.43 (dd, 1H, J$_1$=9.0 Hz, J$_2$=3.2 Hz), 4.59 (d, 2H, J=6.4 Hz), 3.61-3.58 (m, 4H), 3.41-3.39 (m, 4H), 2.05 (s, 3H).

Example 30

1-(3-Fluorophenyl)-N-((2'-methyl-[2,4'-bipyridin]-5-yl)methyl)-2-oxo-1,2-dihydropyridine-4-carboxamide (89)

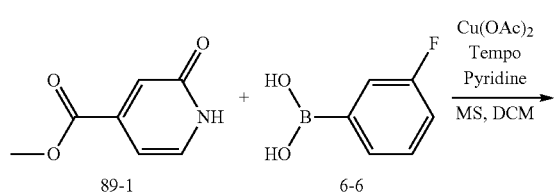

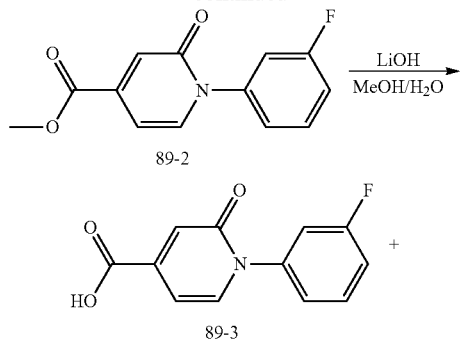

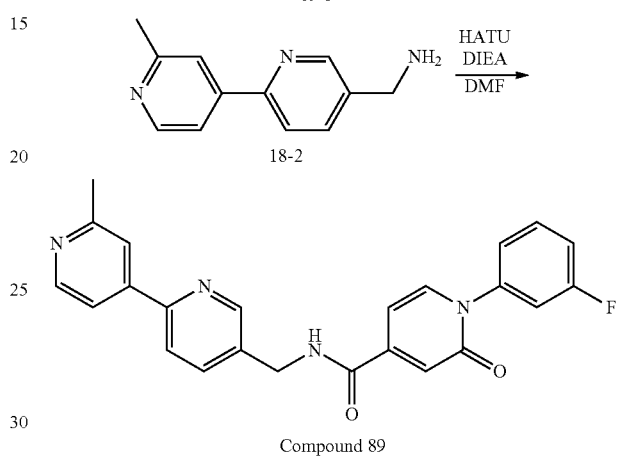

Compound 89

Step 1: A mixture of methyl 2-oxo-1,2-dihydropyridine-4-carboxylate 89-1 (153 mg, 1.00 mmol), (3-fluorophenyl)boronic acid 6-6 (280 mg, 2.00 mmol), Cu(OAc)$_2$ (36 mg, 0.2 mmol), molecular sieves (4 Å, activated, 200 mg), pyridine (162 μL, 2.0 mmol) and TEMPO (2,2,6,6-tetramethyl-1-piperidinyloxy, free radical, 172 mg, 1.1 mmol) in DCM (2.0 mL) was stirred at room temperature under dry air. The mixture was then filtered through celite (washed with ethyl acetate); and the filtrate was washed with 5% ammonia solution, dried with Na$_2$SO$_4$ and concentrated with rotavap. The residue was subjected to silica gel column chromatography with 1:3 ethyl acetate/DCM as eluent to give methyl 1-(3-fluorophenyl)-2-oxo-1,2-dihydropyridine-4-carboxylate as a solid 89-2.

Step 2: To a solution of methyl 1-(3-fluorophenyl)-2-oxo-1,2-dihydropyridine-4-carboxylate 89-2 (50 mg, 0.202 mmol) in water (0.5 mL) and methanol (0.5 mL) was added LiOH (20 mg, 0.835 mmol). After stirring at room temperature for 30 minutes, the mixture was concentrated with rotavap and the residue extracted with ethyl acetate, which was then evaporated to give crude 1-(3-fluorophenyl)-2-oxo-1,2-dihydropyridine-4-carboxylic acid 89-3.

Step 3: To a mixture of (2'-methyl-[2,4'-bipyridin]-5-yl)methanamine 18-2 (14 mg, 0.07 mmol), 1-(3-fluorophenyl)-2-oxo-1,2-dihydropyridine-4-carboxylic acid 89-3 (16 mg, 0.07 mmol), and HATU (29 mg, 0.076 mmol) were added N,N-diisopropylethylamine (DIEA, 17 μL, 0.098 mmol) and DMF (0.5 mL). The solution was stirred overnight at room temperature and subjected to reverse phase preparative HPLC separation to yield 1-(3-fluorophenyl)-N-((2'-methyl-[2,4'-bipyridin]-5-yl)methyl)-2-oxo-1,2-dihydropyridine-4-carboxamide 89. MS m/z 415.2 (M+1).

Example 31

N-(4-(4-methyl-1H-imidazol-1-yl)benzyl)biphenyl-4-carboxamide (92)

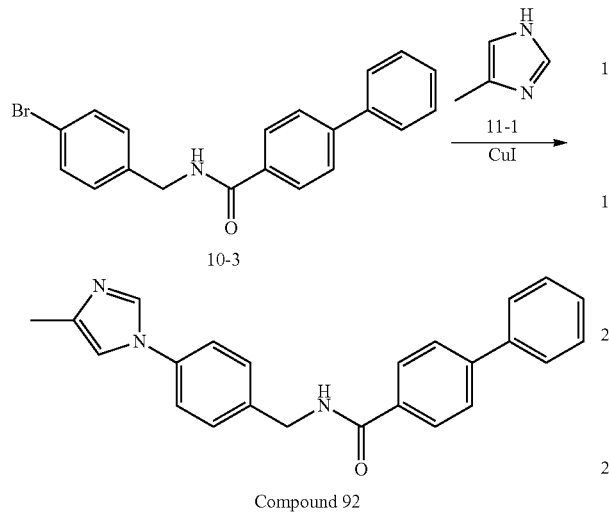

Compound 92

To a reaction vessel was added N-(4-bromobenzyl)biphenyl-4-carboxamide 10-3 (50 mg, 0.14 mmol), 4-methyl-1H-imidazole 11-1 (17 mg, 0.2 mmol), CuI (9 mg, 0.05 mmol), 1,3-di(pyridin-2-yl)propane-1,3-dione (15 mg, 0.07 mmol), $Cs_2CO_3$ (89 mg, 0.27 mmol) and DMF (0.7 mL). The reaction was flushed with nitrogen and stirred at 110° C. overnight. After cooling to room temperature, the reaction was diluted into ethyl acetate. The salt was removed by filtration and filtrate was dried. The residue was purified by HPLC to give N-(4-(4-methyl-1H-imidazol-1-yl)benzyl)biphenyl-4-carboxamide 92. MS m/z 368.2 (M+1). $^1$H NMR 400 MHz (DMSO-$d_6$) δ 9.16 (t, 1H), 8.17 (s, 1H), 8.02 (d, 2H), 7.81 (d, 2H), 7.75 (d, 2H), 7.58 (d, 2H), 7.52-7.40 (m, 6H), 4.54 (d, 2H), 2.17 (s, 3H).

Example 32

N-((1-(2-Fluoroisonicotinoyl)piperidin-4-yl)methyl)-6-(3-fluorophenyl)nicotinamide (93)

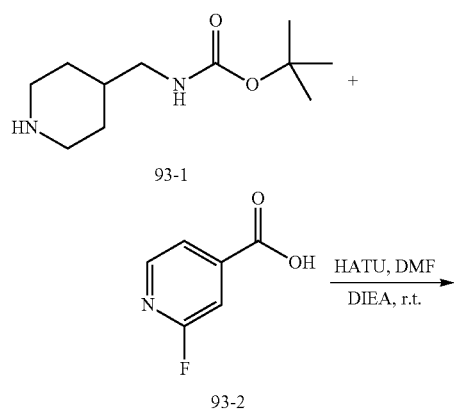

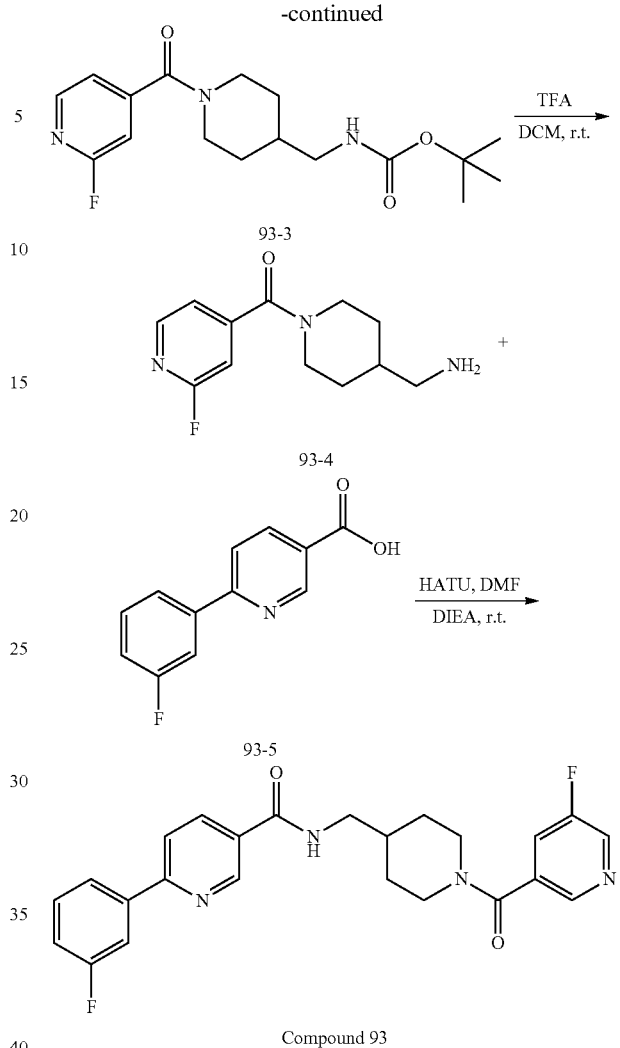

Compound 93

Step 1: To a mixture of tert-butyl piperidin-4-ylmethylcarbamate 93-1 (1.07 g, 5.0 mmol), 2-fluoroisonicotinic acid 93-2 (706 mg, 5.0 mmol) and HATU (1.90 g, 5.0 mmol) in DMF (20 mL) was added DIEA (2.5 mL, 15.0 mmol) at room temperature. The mixture was stirred for 2 hours. The mixture was diluted with ethyl acetate (100 mL), washed with $H_2O$ and brine, dried over $Na_2SO_4$, and concentrated to dryness by rotary evaporation. The crude product was purified by silica gel flash chromatography, and eluted with 5% methanol in dichloromethane to give tert-butyl (1-(2-fluoroisonicotinoyl)piperidin-4-yl)methylcarbamate 93-3 as a pale yellow solid. MS m/z 338.1 (M+1)

Step 2: To a solution of tert-butyl (1-(2-fluoroisonicotinoyl)piperidin-4-yl)methylcarbamate 93-3 (1.81 g, 5.0 mmol) in dichloromethane (10 mL) was added TFA (5 mL) dropwise at room temperature. The mixture was stirred for 10 hours, and then the solvents were removed by rotary evaporation. The residue was dissolved in ethyl acetate (100 mL), washed with saturated aqueous $NaHCO_3$ solution, $H_2O$ and brine, dried over $Na_2SO_4$ and concentrated to dryness by rotary evaporation to give (4-(aminomethyl)piperidin-1-yl)(2-fluoropyridin-4-yl)methanone 93-4 as a yellow oil. MS m/z 238.1 (M+1)

Step 3: To a mixture of (4-(aminomethyl)piperidin-1-yl)(2-fluoropyridin-4-yl)methanone 93-4 (47 mg, 0.20 mmol), 6-(3-fluorophenyl)nicotinic acid 93-5 (43 mg, 0.20 mmol) and HATU (76 mg, 0.20 mmol) in DMF (1 mL) was added DIEA (0.16 mL, 0.50 mmol). The mixture was stirred at room temperature for 2 hours. The solvent was removed by rotary evaporation. The crude product was purified by reverse phase HPLC to give N-41-(2-fluoroisonicotinoyl)piperidin-4-yl)methyl)-6-(3-fluorophenyl)nicotinamide 93 as a white powder. MS m/z 437.20 (M+1); $^1$H NMR 400 MHz (DMSO-$d_6$) δ 9.14 (d, 1H, J=1.6 Hz), 8.83 (t, 1H, J=6.0 Hz), 8.39-8.33 (m, 2H), 8.20 (d, 1H, J=8.4 Hz), 8.07-8.00 (m, 2H), 7.65-7.59 (m, 1H), 7.42-7.37 (m, 2H), 7.30 (m, 1H), 4.52 (d, 1H, J=13.2 Hz), 3.45-3.27 (m, 3H), 3.12-3.06 (m, 1H), 2.88-2.84 (m, 1H), 1.94-1.86 (m, 2H), 1.70 (d, 1H, J=12.8 Hz), 1.29-1.22 (m, 2H).

Example 33

N-((2'-methyl-[2,4'-bipyridin]-5-yl)methyl)-6-phenoxynicotinamide (94)

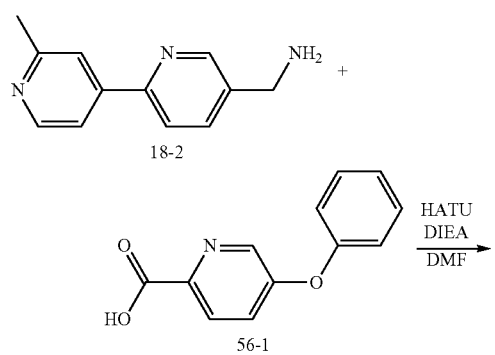

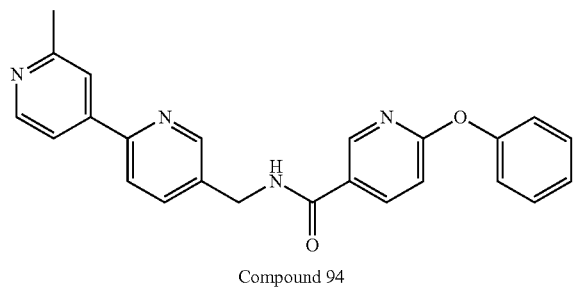

Compound 94

To a mixture of (2'-methyl-[2,4'-bipyridin]-5-yl)methanamine 18-2 (20 mg, 0.10 mmol), 6-phenoxynicotinic acid 56-1 (21.5 mg, 0.10 mmol), and HATU (40 mg, 0.105 mmol) were added N,N-diisopropylethylamine (DIEA, 26 μL, 0.15 mmol) and DMF (0.5 mL). The solution was stirred overnight at room temperature and was subjected to reverse phase preparative HPLC separation to yield N-((2'-methyl-[2,4'-bipyridin]-5-yl)methyl)-6-phenoxynicotinamide 94 as a solid. MS m/z 397.2 (M+1).

Example 34

N-((2',3-dimethyl-[2,4'-bipyridin]-5-yl)methyl)-5-(pyrazin-2-yl)picolinamide fumarate

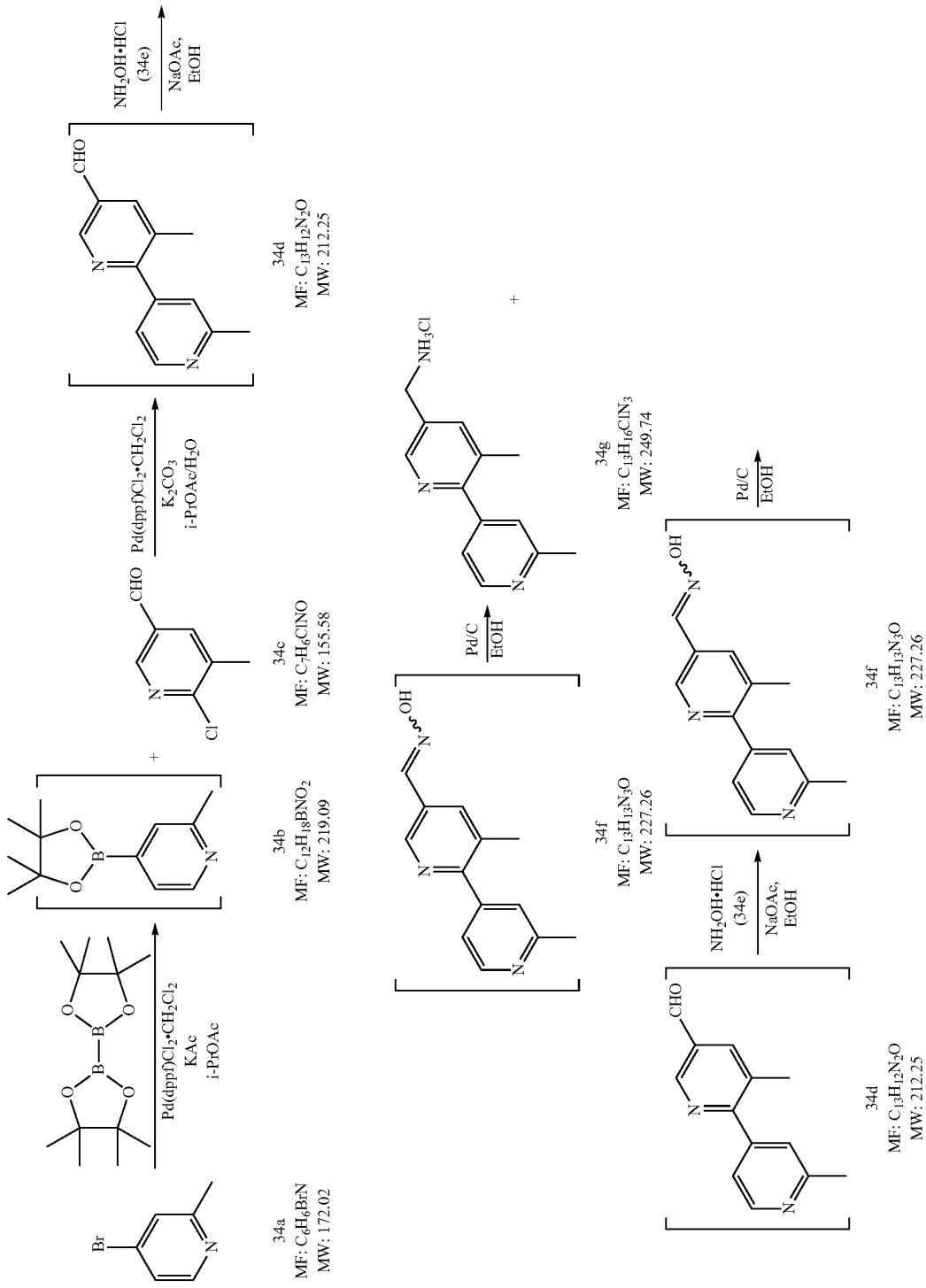

-continued
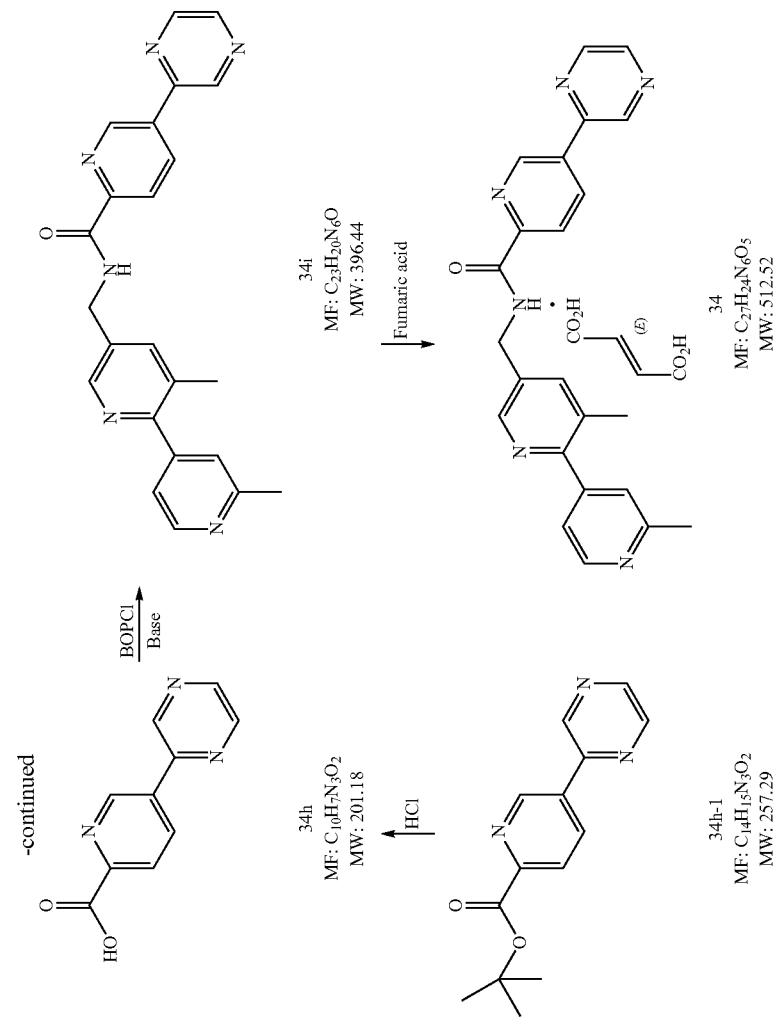

-continued
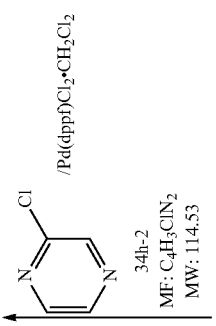
34h-2
MF: C$_4$H$_3$ClN$_2$
MW: 114.53
Pd(dppf)Cl$_2$·CH$_2$Cl$_2$
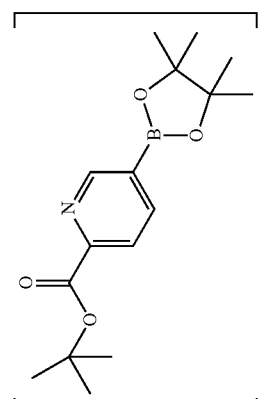
34h-3
MF: C$_{16}$H$_{24}$BNO$_4$
MW: 305.18
Pd(dppf)Cl$_2$·CH$_2$Cl$_2$
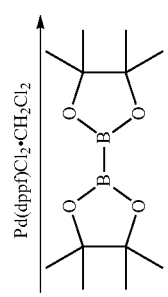
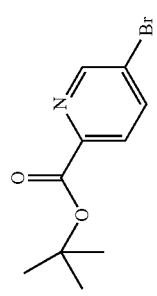
34h-4
MF: C$_{10}$H$_{12}$BrNO$_2$
MW: 258.11

Preparation of Intermediates

2-methyl-4-(4,4,5,5-tetramethyl-1,3,2-dioxaborolan-2-yl)pyridine (34b)

To a 5-L four-necked flask equipped with an overhead stirrer, a thermocouple and a condenser was charged 4-bromo-2-methylpyridine (34a, 192.7 g, 1120 mmol), 4,4, 4',4',5,5,5',5'-octamethyl-2,2'-bi(1,3,2-dioxaborolane) (312.9 g, 1232 mmol), Pd(dppf)Cl$_2$·CH$_2$Cl$_2$ (4.57 g, 5.6 mmol), KOAc (219.7 g, 2240 mmol), and iso-propyl acetate (1920 mL). The mixture was stirred at 75° C. for 18 h, cooled to 50° C. and filtered through Celite. Concentration of the filtrate to almost dryness afforded the crude 2-methyl-4-(4,4, 5,5-tetramethyl-1,3,2-dioxaborolan-2-yl)pyridine (34b) as a black oil.

2',3-dimethyl-[2,4'-bipyridine]-5-carbaldehyde (34d)

To a 5-L four-necked flask equipped with an overhead stirrer, a thermocouple and a condenser was charged with 2-methyl-4-(4,4,5,5-tetramethyl-1,3,2-dioxaborolan-2-yl) pyridine (34b, 1120 mmol), 6-chloro-5-methylnicotinaldehyde (34c, 174.3 g, 1120 mmol), Pd(dppf)Cl$_2$·CH$_2$Cl$_2$ (4.57 g, 5.6 mmol), K$_2$CO$_3$ (309.6 g, 2240 mmol), and iso-propyl acetate (1120 mL)/water (1120 mL). The mixture was stirred at 75° C. for 4 h, and cooled to 30° C. The organic layer was separated, washed with 10% NaCl (1120 g), and treated with activated charcoal (50 g) at 50° C. for 2 h before cooling to rt and filtered through Celite. Concentration of the filtrate to almost dryness afforded the crude 2',3-dimethyl-[2,4'-bipyridine]-5-carbaldehyde (34d) as a brown oil.

2',3-dimethyl-[2,4'-bipyridine]-5-carbaldehyde oxime (34f)

To a 5-L four-necked flask equipped with an overhead stirrer, and a thermocouple was charged with 2',3-dimethyl-[2,4'-bipyridine]-5-carbaldehyde (34d, 1120 mmol), hydrochloro hydroxyamine (34e, 140.1 g, 2016 mmol), and ethanol (1600 mL). The mixture was stirred at 23° C. for 2 h before the addition of NaOAc (183.8 g, 2240 mmol, 2 eq) and iso-propyl acetate (2 L)/water (2 L). The aqueous layer was back-extracted with iso-propyl acetate (2 L) after the layer separation. The combined organic layers were concentrated to almost dryness to afford the crude 2',3-dimethyl-[2,4'-bipyridine]-5-carbaldehyde oxime (34f) as a brown oil.

(2',3-dimethyl-[2,4'-bipyridin]-5-yl)methanamine hydrochloride (34g)

To a 2-L Parr-Shaker Reactor was charged 2',3-dimethyl-[2,4'-bipyridine]-5-carbaldehyde oxime (34f, 560 mmol), Pd/C (23 g, 112 mmol, 50 wt % wet), conc. HCl (94 mL), and ethanol (600 mL). The reaction mixture was shaked at rt under 40 psi H$_2$ until H$_2$ was consumed. After filtration through Celite, the filtrate was solvent-exchanged to ethanol by repeating the concentration and refilling with ethanol twice. The product was stirred in ethanol/iso-propyl acetate (800 mL, v 1/1) at rt for 18 h. The solid was collected by filtration and rinsed with EtOH/iso-propyl acetate (400 mL, v 1/1). The wet cake was dried at 50° C. under vacuum for 18 h to afford (2',3-dimethyl-[2,4'-bipyridin]-5-yl)methanamine hydrochloride (34g) as a light yellow powder. $^1$H NMR (500 MHz, DMSO-d$_6$) δ ppm 2.44 (s, 3H), 2.89 (s, 3H), 4.15 (q, J=5 Hz, 2H), 8.05 (dd, J=1.6, 6.0 Hz, 1H), 8.10 (d, J=1.6 Hz, 1H), 8.13 (s, 1H), 8.76 (d, J=2.0 Hz, 1H), 8.85 (d, J=6.0 Hz, 1H), 8.88 (brd, 3H).

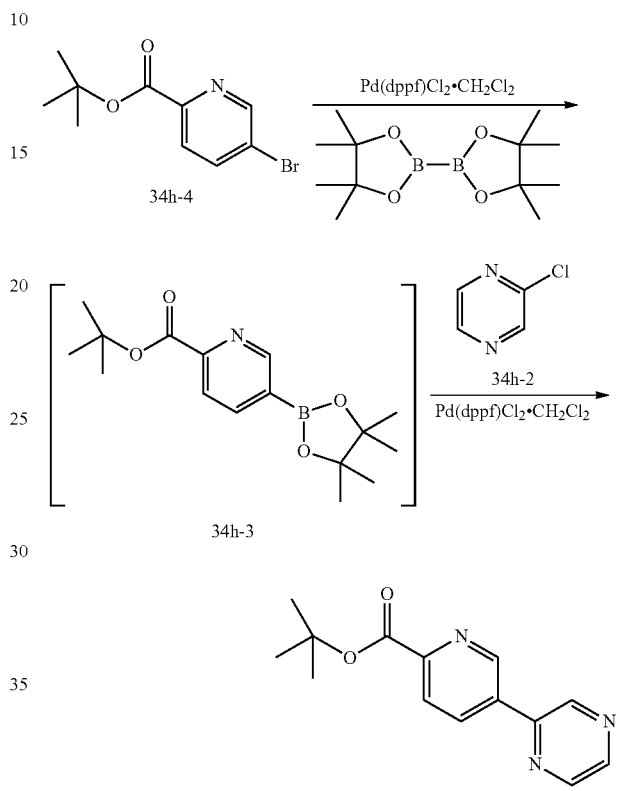

tert-Butyl-5-(pyrazin-2-yl)-picolinate (34h-1)

The 250 mL flask was charged with tert-butyl 5-bromopicolinate 34h-4 (12.9 g, 50 mmol), 4,4,4',4',5,5,5',5'-octamethyl-2,2'-bi(1,3,2-dioxaborolane) (13.9 g, 55 mmol), KOAc (9.8 g, 100 mmol), PdCl$_2$(dppf)-CH$_2$Cl$_2$ adduct (0.408 g, 0.5 mmol) and THF (80 mL). The flask was sealed under nitrogen and the mixture was stirred at 80° C. for 24 hours. After completion of the reaction, it was cooled to room temperature and filtered through Celite. The filtrate was taken in 500 mL 4-necked RB flask and charged with aqueous K$_2$CO$_3$ solution (13.8 g in 100 ml Of water), 2-chloropyrazine (6.8 g, 60 mmol), and PdCl$_2$(dppf)-CH$_2$Cl$_2$ adduct (0.204 g, 0.25 mmol). The reaction mixture was stirred at 64° C. for 2 h under nitrogen, cooled to room temperature and filtered through Celite. The filtrate was diluted with i-PrOAc (100 mL) and the aqueous layer separated. The organic layer was washed with water (2×100 mL), concentrated to ~20 mL of volume and diluted with heptane (200 mL). The solid was collected by filtration, washed with heptane (50 mL), and dried at 40° C. to obtain 34h-1 as a pale yellow solid.

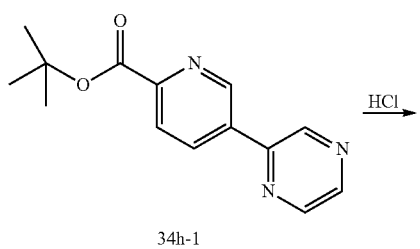

5-(Pyrazin-2-yl) picolinic acid (34 h)

To a 100 mL four-necked flask equipped with an overhead stirrer, a thermocouple and a condenser was charged tert-butyl-5-(pyrazin-2-yl)-picolinate (34h-1) (2.57 g, 10.0 mmol), THF (30 mL) and 6 N HCl (10 mL, 60 mmol) The mixture was stirred at 65° C. for 4 hours, then the THF was concentrated under vacuum and aqueous layer was neutralized with 6 N NaOH to pH ~4.0. The solid was collected by filtration and washed with water (20 mL). The Wet cake was dried at 40° C. to obtain 34h as a pale yellow solid.

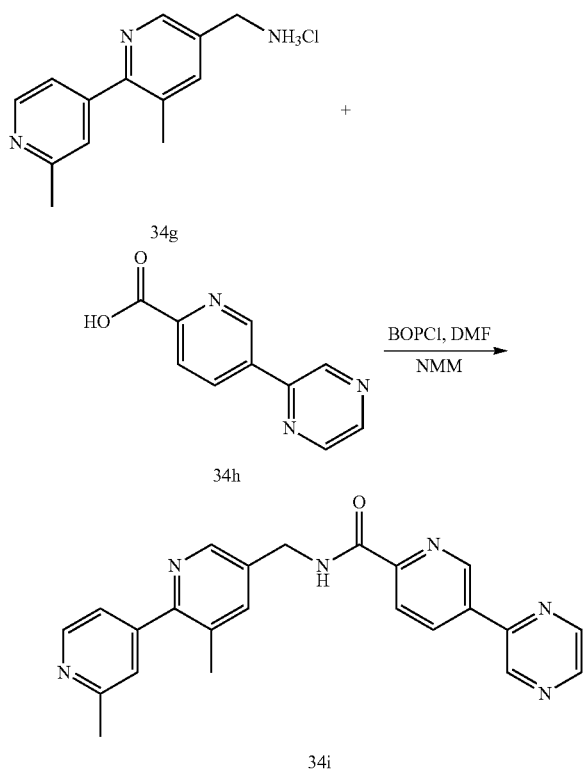

N-[(2',3-dimethyl-{2,4'-bipyridin}-5-yl]-methyl)-5-(pyrazin-2-yl)-picolinamide (34i)

To a 100 mL four-necked flask equipped with an overhead stirrer, and a thermocouple was charged with acid 34h (1.0 g, 4.0 mmol), DMF (10 mL) and N-methylmorpholine (1.21 g, 12.0 mmol) under nitrogen purge. After stirring the reaction mixture for 30 min at 23° C., amine 34g (0.805 g, 4.0 mmol), BOPCl (1.12 g, 4.4 mmol) were added. The reaction mixture was stirred for 6 h at 23° C. After completion of the reaction, it was diluted with water (50 mL, 1:1) at 23° C. and the suspension was stirred for 1 h at 23° C. The solid was collected by filtration and washed with water (20 mL). The wet cake was dried at 40° C. for 12 h to obtain 34i as a pale yellow solid. $^1$H NMR (500 MHz, CDCl$_3$) δ ppm 2.36 (s, 3H), 2.62 (s, 3H), 4.75 (s, 2H), 7.09-7.38 (m, 2H), 7.67 (s, 1H), 8.24-8.80 (m, 7H), 9.02-9.31 (m, 2H).

N-((2',3-dimethyl-[2,4'-bipyridin]-5-yl)methyl)-5-(pyrazin-2-yl)picolinamide fumarate (34)

N-[(2',3-dimethyl-{2,4'-bipyridin}-5-yl]-methyl)-5-(pyrazin-2-yl)-picolinamide (34, 14.67 mg) was dissolved in ethyl acetate at 5 mg/ml (3.0 ml) in a 10 ml vial at room temperature ~25° C. While stirring, 5.2 mg of fumaric acid solid was added to the solution. The slurry started to clear upon addition of fumaric acid. After about 10 mins., the fumarate salt slowly started to precipitate out. The reaction mixture was stirred overnight to ensure completion of reaction. The slurry was then filtered using a 0.2 um PVDF filter using a vacuum filtration system, and the collected crystals were washed with ethyl ether. The fumarate salt crystals were dried overnight at 40° C. under 30 in. Hg vacuum. The structure of the fumarate salt was confirmed by Differential Scanning calorimetry, X-Ray Powder Diffraction, and Elemental Analyses. Theoretical calculated for $C_{23}H_{20}N_6O.C_4H_4O_4$: C, 63.31; H, 4.69; N, 16.40; 0, 15.61; C:N ratio, 3.86. Found: C, 58.39; H, 4.61; N, 13.83; C:N ratio, 4.22; stoichiometry, 1.09.

Example 35

Wnt-Luc Reporter Assay for Pathway Inhibition of Wnt Signaling

This example provides a method that is useful for evaluating test compounds for inhibition of Wnt signaling.

Mouse leydig cell TM3 cells (obtained from American Type Culture Collection, ATCC, Manassas, Va.) are cultured in 1:1 mixture of Ham's F12 medium and Dulbecco's modified Eagle's medium (Gibco/Invitrogen, Carlsbad, Calif.) supplemented with 2.5% FBS (Gibco/Invitrogen, Carlsbad, Calif.) and 5% horse serum (Gibco/Invitrogen, Carlsbad, Calif.), 50 unit/mL penicillin and 50 µg/mL of streptomycin (Gibco/Invitrogen, Carlsbad, Calif.) at 37° C. with 5% CO$_2$ in air atmosphere. TM3 cells in a 10 cm dish are co-transfected with 8 µg of STF-reporter plasmid containing a luciferase gene driven by Wnt-responsive elements and 2 µg of pcDNA3.1-Neo (Gibco/Invitrogen, Carlsbad, Calif.) with 30 µL of FuGENE6 (Roche Diagnostics, Indianapolis, Ind.) following the manufacturer's protocol. Stable cell lines (TM3 Wnt-Luc) were selected with 400 µg/mL of G418 (Gibco/Invitrogen, Carlsbad, Calif.). The TM3 Wnt-Luc cells and L-cell Wnt3a cells (obtained from American Type Culture Collection, ATCC, Manassas, Va.; cultured in Dulbecco's modified Eagle's medium (Gibco/Invitrogen, Carlsbad, Calif.) supplemented with 10% FBS (Gibco/Invitrogen, Carlsbad, Calif.) and 50 unit/mL penicillin and 50 µg/mL of streptomycin (Gibco/Invitrogen, Carlsbad, Calif.) at 37° C. with 5% $CO_2$ in air atmosphere) are trypsinized and co-cultured into a 384-well plate with DMEM medium supplemented with 2% FBS, and treated with different concentrations of a compound of the invention. After 24 hours, the firefly luciferase activities are assayed with the Bright-Glo™ Luciferase Assay System (Promega, Madison, Wis.). The $IC_{50}$ is measured when the effect of the compound reduces the luminescence signal by 50%.

Example 36

Wnt-Luc Reporter Assay for Pathway Inhibition of Wnt Signaling

This example provides another method that is useful for evaluating test compounds for inhibition of Wnt signaling.

Human embryonic kidney 293 cells (obtained from American Type Culture Collection, ATCC, Manassas, Va.) are cultured in DMEM medium (Gibco/Invitrogen, Carlsbad, Calif.) supplemented with 10% FBS (Gibco/Invitrogen, Carlsbad, Calif.), 50 unit/mL penicillin and 50 μg/mL of streptomycin (Gibco/Invitrogen, Carlsbad, Calif.) at 37° C. with 5% $CO_2$ in air atmosphere. 293 cells in a 10 cm dish are co-transfected with 8 μg of STF-reporter plasmid containing a luciferase gene driven by Wnt-responsive elements and 2 μg of pcDNA3.1-Neo (Gibco/Invitrogen, Carlsbad, Calif.) with 30 μL of FuGENE6 (Roche Diagnostics, Indianapolis, Ind.) following the manufacturer's protocol. Stable cell lines (293 Wnt-Luc) were selected with 400 μg/mL of G418 (Gibco/Invitrogen, Carlsbad, Calif.). The 293 Wnt-Luc cells and L-cell Wnt3a cells (obtained from American Type Culture Collection, ATCC, Manassas, Va.) are trypsinized and co-cultured into a 384-well plate with DMEM medium supplemented with 2% FBS, and treated with different concentrations of a compound of the invention. After 24 hours, the firefly luciferase activities are assayed with the Bright-Glo™ Luciferase Assay System (Promega, Madison, Wis.). The $IC_{50}$ is measured when the effect of the compound reduces the luminescence signal by 50%.

Example 37

Biological Results

Compounds of the invention are active in an assay system as described in the Examples above, and show an inhibition $IC_{50}$ within the range of 0.01 nM to 10 μM. Particularly active compounds are those exemplified in Table 1 showing $IC_{50}$ values within the range of 0.01 nM to 1 μM, and more particularly within the range of 0.01 nM to 100 nM; most preferred are compounds showing $IC_{50}$ values within the range of 0.01 nM to 10 nM.

TABLE 1

| Ex. | Structure | MS (m/z) (M + 1) | LC retention time (min) | $IC_{50}$ (nM) |
| --- | --- | --- | --- | --- |
| 1 | 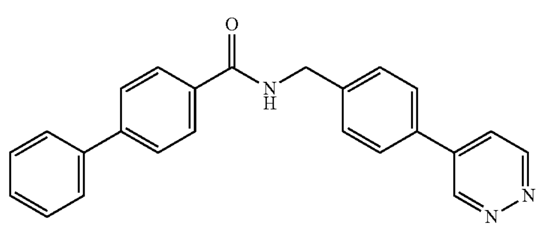 [SMILES: O=C(NCc1ccc(-c2ccnnc2)cc1)c1ccc(-c2ccccc2)cc1] | 365.43 | 1.844 | 1.9 |
| 2 | 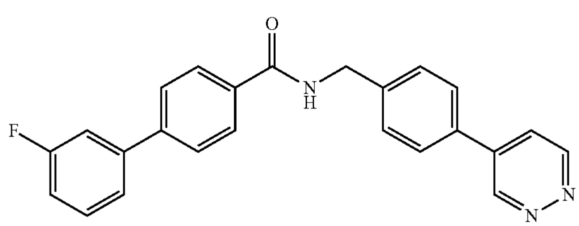 [SMILES: O=C(NCc1ccc(-c2ccnnc2)cc1)c1ccc(-c2cccc(F)c2)cc1] | 383.43 | 1.891 | 0.95 |
| 3 | 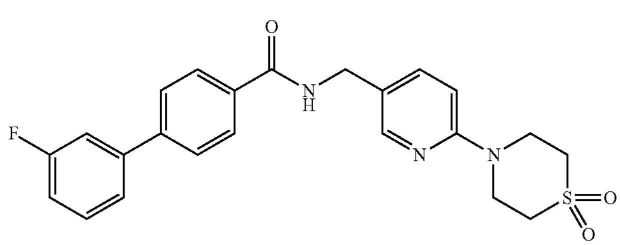 [SMILES: O=C(NCc1ccc(N2CCS(=O)(=O)CC2)nc1)c1ccc(-c2cccc(F)c2)cc1] | 439.5 | 1.64 | 2.3 |

TABLE 1-continued

| Ex. | Structure | MS (m/z) (M + 1) | LC retention time (min) | IC$_{50}$ (nM) |
|---|---|---|---|---|
| 4 | 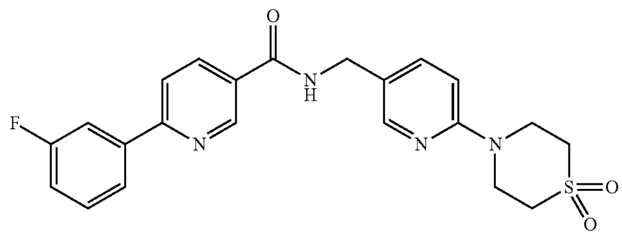 [SMILES: O=C(NCc1ccc(N2CCS(=O)(=O)CC2)nc1)c1ccc(-c2cccc(F)c2)nc1] | 440.49 | 1.709 | 2.4 |
| 5 | 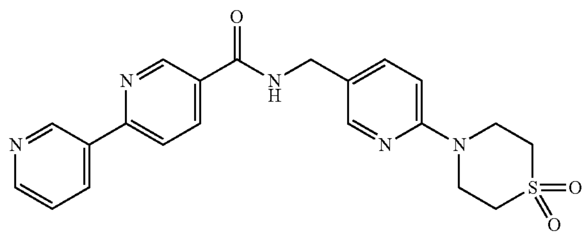 [SMILES: O=C(NCc1ccc(N2CCS(=O)(=O)CC2)nc1)c1ccc(-c2cccnc2)nc1] | 423.49 | 0.831 | 129 |
| 6 | 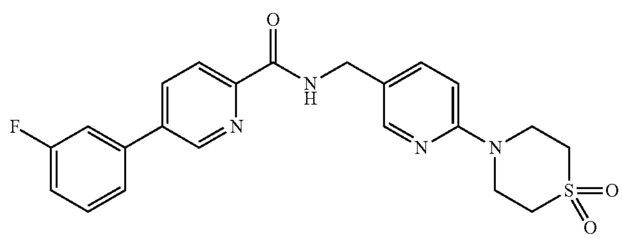 [SMILES: O=C(NCc1ccc(N2CCS(=O)(=O)CC2)nc1)c1ccc(-c2cccc(F)c2)cn1] | 440.49 | 1.67 | 0.9 |
| 7 | 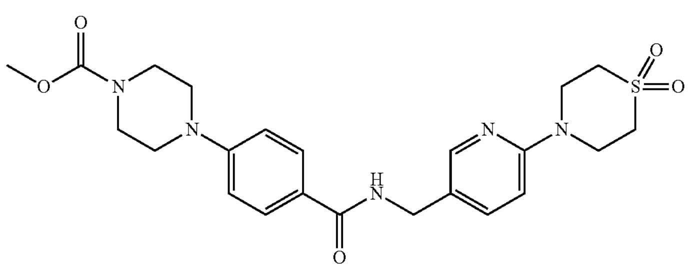 [SMILES: COC(=O)N1CCN(c2ccc(C(=O)NCc3ccc(N4CCS(=O)(=O)CC4)nc3)cc2)CC1] | 487.57 | 1.22 | 19 |
| 8 | 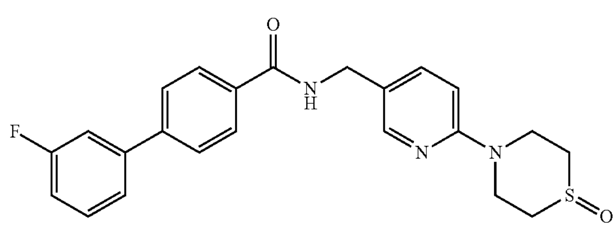 [SMILES: O=C(NCc1ccc(N2CCS(=O)CC2)nc1)c1ccc(-c2cccc(F)c2)cc1] | 423.5 | 1.554 | 0.7 |
| 9 | 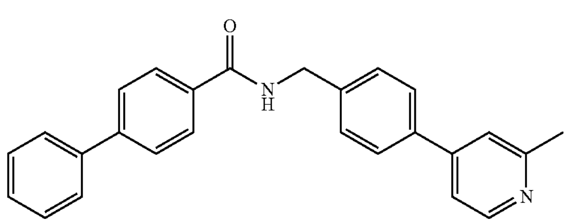 [SMILES: Cc1cc(-c2ccc(CNC(=O)c3ccc(-c4ccccc4)cc3)cc2)ccn1] | 378.47 | 1.743 | 0.06 |

TABLE 1-continued

| Ex. | Structure | MS (m/z) (M + 1) | LC retention time (min) | IC$_{50}$ (nM) |
|---|---|---|---|---|
| 10 | 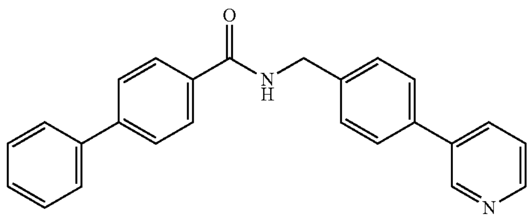 [SMILES: O=C(NCc1ccc(-c2cccnc2)cc1)c1ccc(-c2ccccc2)cc1] | 364.44 | 1.698 | 12.5 |
| 11 | 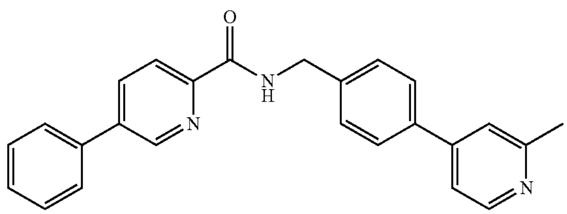 [SMILES: Cc1cc(-c2ccc(CNC(=O)c3ccc(-c4ccccc4)cn3)cc2)ccn1] | 379.45 | 1.953 | 0.2 |
| 12 | 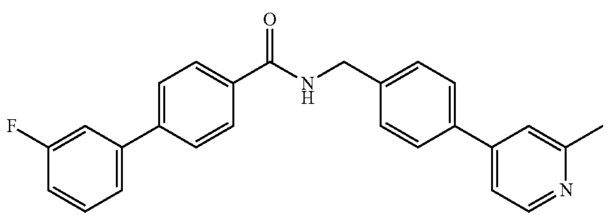 [SMILES: Cc1cc(-c2ccc(CNC(=O)c3ccc(-c4cccc(F)c4)cc3)cc2)ccn1] | 396.46 | 1.5 | 0.06 |
| 13 | 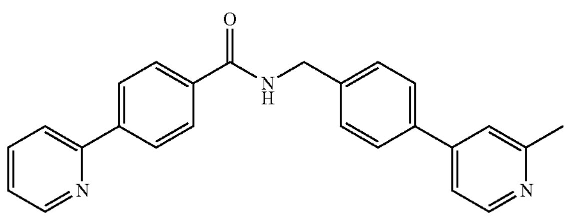 [SMILES: Cc1cc(-c2ccc(CNC(=O)c3ccc(-c4ccccn4)cc3)cc2)ccn1] | 379.45 | 1.177 | 0.1 |
| 14 | 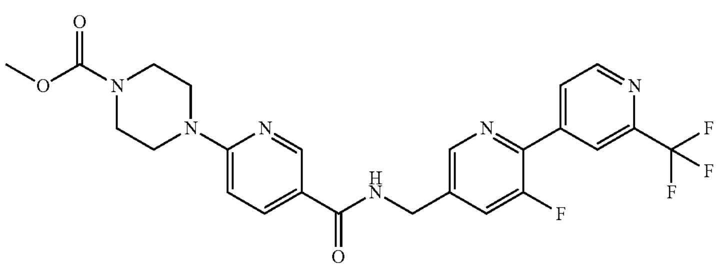 [SMILES: COC(=O)N1CCN(c2ccc(C(=O)NCc3cnc(-c4ccnc(C(F)(F)F)c4)c(F)c3)cn2)CC1] | 518.46 | 1.647 | 0.44 |
| 15 | 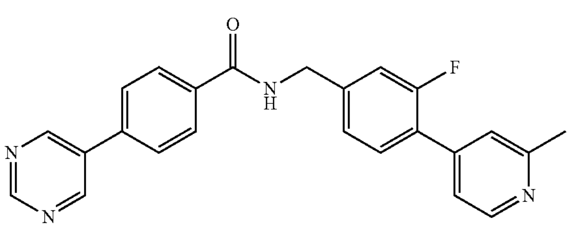 [SMILES: Cc1cc(-c2ccc(CNC(=O)c3ccc(-c4cncnc4)cc3)cc2F)ccn1] | 398.43 | 1.3 | 0.01 |
| 16 | 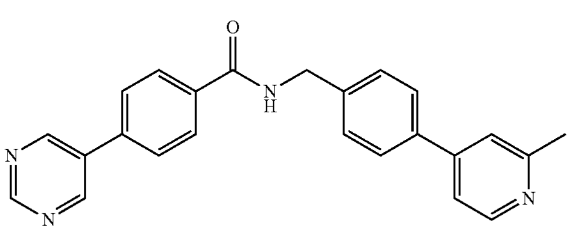 [SMILES: Cc1cc(-c2ccc(CNC(=O)c3ccc(-c4cncnc4)cc3)cc2)ccn1] | 380.44 | 1.251 | 0.05 |

TABLE 1-continued

| Ex. | Structure | MS (m/z) (M + 1) | LC retention time (min) | IC$_{50}$ (nM) |
|---|---|---|---|---|
| 17 | 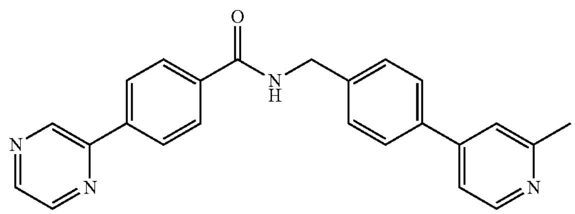 [SMILES: Cc1cc(-c2ccc(CNC(=O)c3ccc(-c4cnccn4)cc3)cc2)ccn1] | 380.44 | 1.469 | 0.06 |
| 18 | 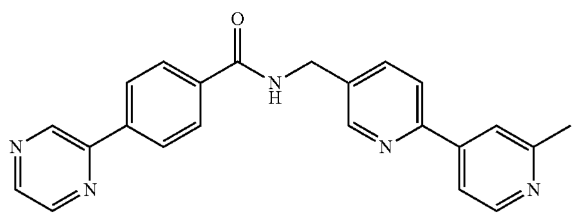 [SMILES: Cc1cc(-c2ccc(CNC(=O)c3ccc(-c4cnccn4)cc3)cn2)ccn1] | 381.43 | 1.371 | 0.2 |
| 19 | 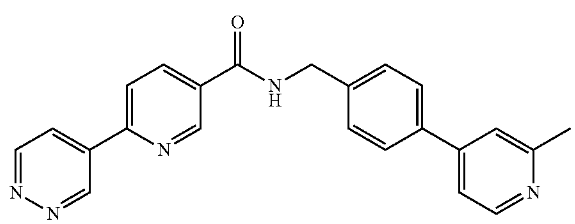 [SMILES: Cc1cc(-c2ccc(CNC(=O)c3ccc(-c4ccnnc4)nc3)cc2)ccn1] | 381.43 | 0.304 | 27 |
| 20 | 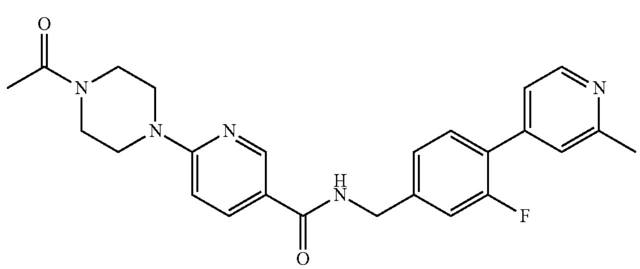 [SMILES: CC(=O)N1CCN(c2ccc(C(=O)NCc3ccc(-c4ccnc(C)c4)c(F)c3)cn2)CC1] | 447.5 | 0.407 | 6.4 |
| 21 | 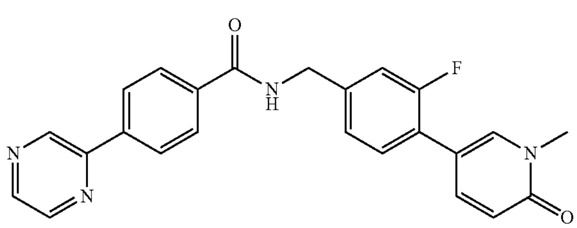 [SMILES: Cn1cc(-c2ccc(CNC(=O)c3ccc(-c4cnccn4)cc3)cc2F)ccc1=O] | 414.43 | 1.763 | 6.4 |
| 22 | 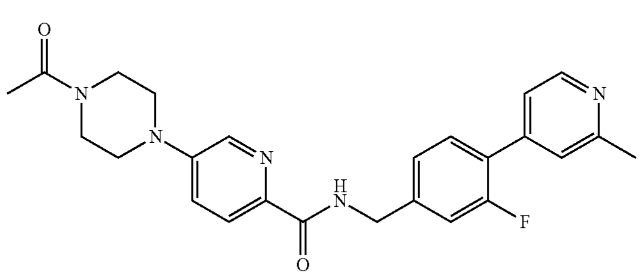 [SMILES: CC(=O)N1CCN(c2ccc(C(=O)NCc3ccc(-c4ccnc(C)c4)c(F)c3)nc2)CC1] | 447.5 | 1.168 | 8.5 |

TABLE 1-continued

| Ex. | Structure | MS (m/z) (M + 1) | LC retention time (min) | IC$_{50}$ (nM) |
|---|---|---|---|---|
| 23 | 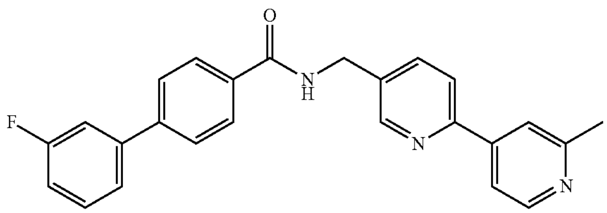 [SMILES: Cc1cc(-c2ccc(CNC(=O)c3ccc(-c4cccc(F)c4)cc3)cn2)ccn1] | 397.44 | 1.927 | 0.1 |
| 24 | 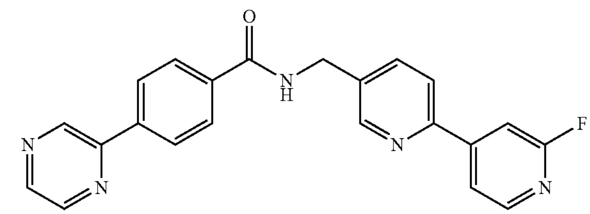 [SMILES: O=C(NCc1ccc(-c2ccnc(F)c2)nc1)c1ccc(-c2cnccn2)cc1] | 385.39 | 1.793 | 0.8 |
| 25 | 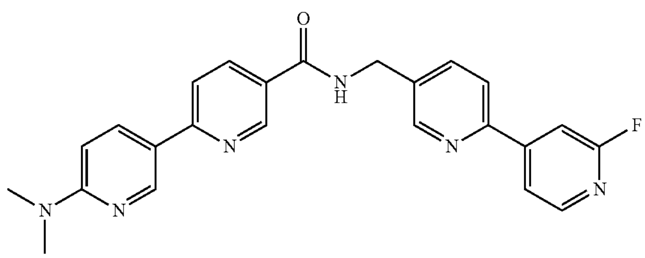 [SMILES: CN(C)c1ccc(-c2ccc(C(=O)NCc3ccc(-c4ccnc(F)c4)nc3)cn2)cn1] | 428.46 | 0.863 | 1.4 |
| 26 | 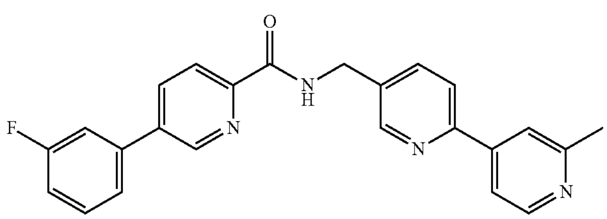 | 398.43 | 1.851 | 0.5 |
| 27 | 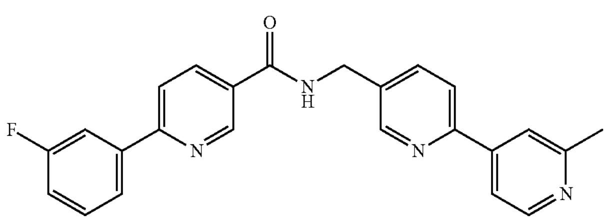 [SMILES: Cc1cc(-c2ccc(CNC(=O)c3ccc(-c4cccc(F)c4)nc3)cn2)ccn1] | 398.43 | 1.69 | 0.2 |
| 28 | 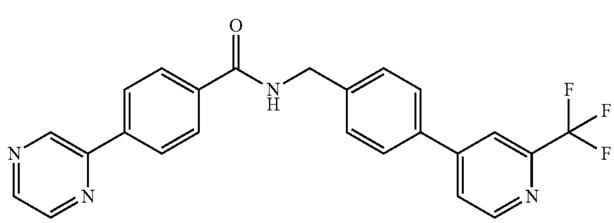 [SMILES: O=C(NCc1ccc(-c2ccnc(C(F)(F)F)c2)cc1)c1ccc(-c2cnccn2)cc1] | 434.41 | 2.359 | 0.9 |
| 29 | 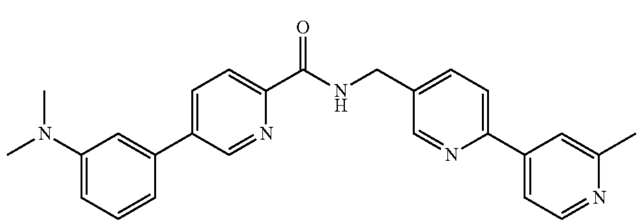 | 423.51 | 1.362 | 43 |

TABLE 1-continued

| Ex. | Structure | MS (m/z) (M + 1) | LC retention time (min) | IC$_{50}$ (nM) |
| --- | --- | --- | --- | --- |
| 30 | 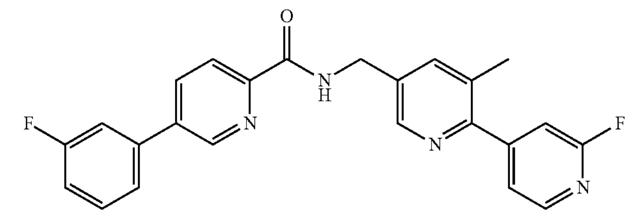 [SMILES: Cc1cc(CNC(=O)c2ccc(-c3cccc(F)c3)cn2)cnc1-c1ccnc(F)c1] | 416.42 | 1.845 | 0.17 |
| 31 | 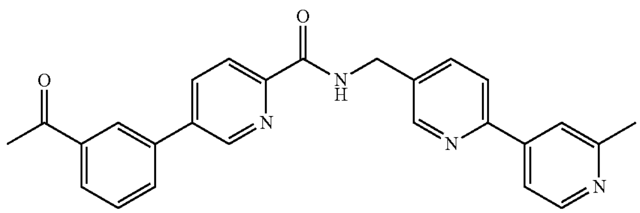 | 422.48 | 1.722 | 8.0 |
| 32 | 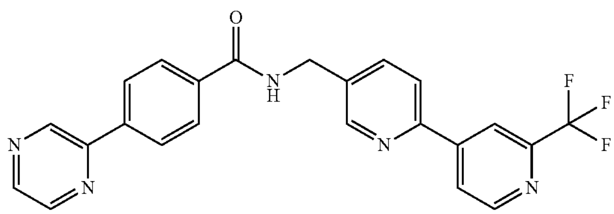 [SMILES: O=C(NCc1ccc(-c2ccnc(C(F)(F)F)c2)nc1)c1ccc(-c2cnccn2)cc1] | 435.4 | 2.158 | 0.7 |
| 33 | 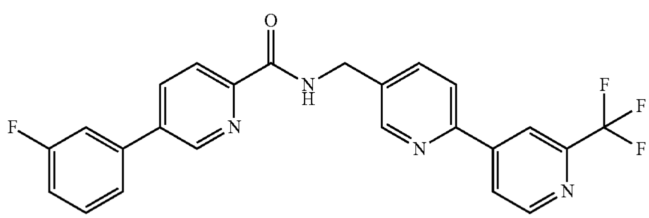 [SMILES: O=C(NCc1ccc(-c2ccnc(C(F)(F)F)c2)nc1)c1ccc(-c2cccc(F)c2)cn1] | 452.4 | 2.875 | 0.2 |
| 34 | 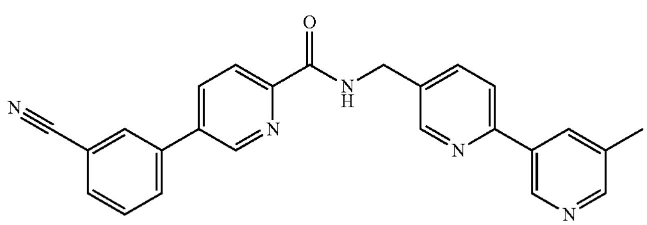 [SMILES: Cc1cncc(-c2ccc(CNC(=O)c3ccc(-c4cccc(C#N)c4)cn3)cn2)c1] | 405.45 | 1.758 | 35.6 |
| 35 | 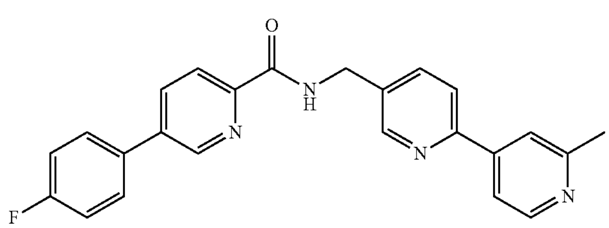 [SMILES: Cc1cc(-c2ccc(CNC(=O)c3ccc(-c4ccc(F)cc4)cn3)cn2)ccn1] | 398.43 | 1.724 | 4.9 |
| 36 | 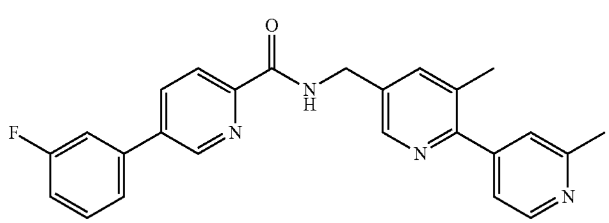 [SMILES: Cc1cc(-c2ncc(CNC(=O)c3ccc(-c4cccc(F)c4)cn3)cc2C)ccn1] | 412.46 | 1.616 | 0.3 |

TABLE 1-continued

| Ex. | Structure | MS (m/z) (M + 1) | LC retention time (min) | IC$_{50}$ (nM) |
|---|---|---|---|---|
| 37 | 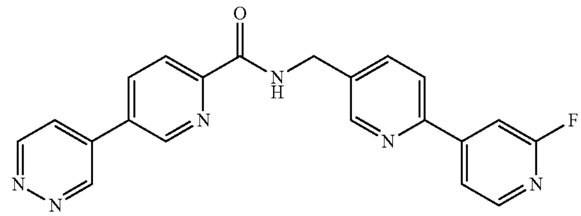 [SMILES: O=C(NCc1ccc(-c2ccnc(F)c2)nc1)c1ccc(-c2ccnnc2)cn1] | 386.38 | 1.318 | 42 |
| 38 | 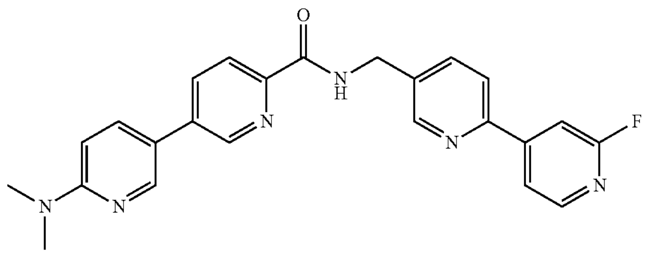 [SMILES: CN(C)c1ccc(-c2ccc(C(=O)NCc3ccc(-c4ccnc(F)c4)nc3)nc2)cn1] | 428.46 | 1.655 | 0.56 |
| 39 | 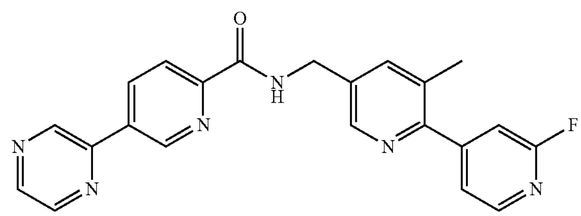 [SMILES: Cc1cc(CNC(=O)c2ccc(-c3cnccn3)cn2)cnc1-c1ccnc(F)c1] | 400.41 | 1.363 | 0.26 |
| 40 | 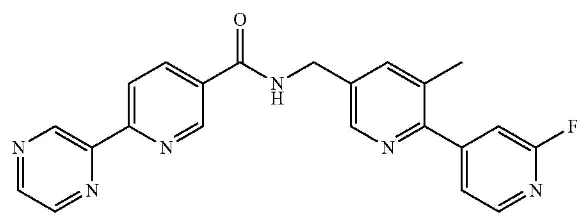 [SMILES: Cc1cc(CNC(=O)c2ccc(-c3cnccn3)nc2)cnc1-c1ccnc(F)c1] | 400.41 | 1.297 | 0.76 |
| 41 | 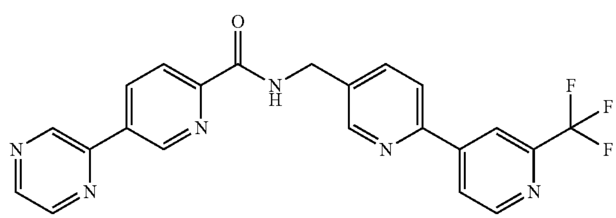 [SMILES: O=C(NCc1ccc(-c2ccnc(C(F)(F)F)c2)nc1)c1ccc(-c2cnccn2)cn1] | 436.39 | 2.385 | 0.36 |
| 42 | 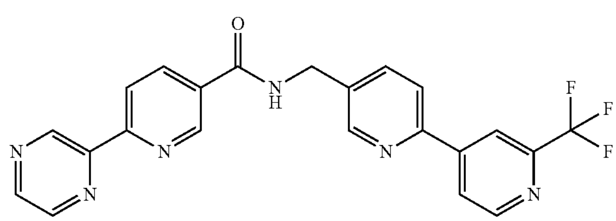 [SMILES: O=C(NCc1ccc(-c2ccnc(C(F)(F)F)c2)nc1)c1ccc(-c2cnccn2)nc1] | 436.39 | 2.226 | 0.79 |
| 43 | 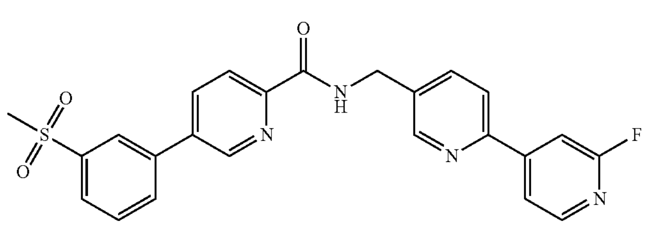 [SMILES: CS(=O)(=O)c1cccc(-c2ccc(C(=O)NCc3ccc(-c4ccnc(F)c4)nc3)nc2)c1] | 462.5 | 1.989 | 718 |

TABLE 1-continued

| Ex. | Structure | MS (m/z) (M + 1) | LC retention time (min) | IC$_{50}$ (nM) |
|---|---|---|---|---|
| 44 | 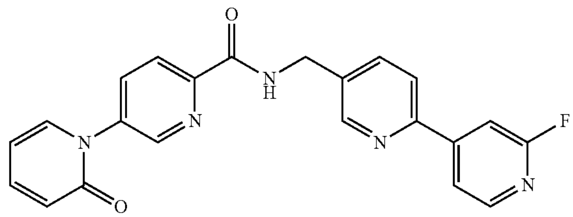 [SMILES: O=C(NCc1ccc(-c2ccnc(F)c2)nc1)c1ccc(-n2ccccc2=O)cn1] | 401.39 | 1.629 | 465 |
| 45 | 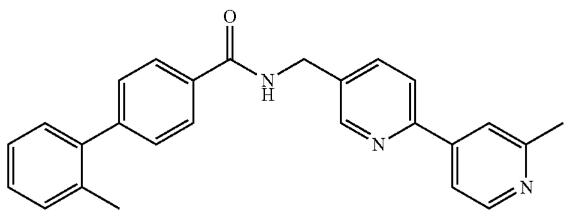 [SMILES: Cc1cc(-c2ccc(CNC(=O)c3ccc(-c4ccccc4C)cc3)cn2)ccn1] | 393.48 | 1.714 | 3.5 |
| 46 | 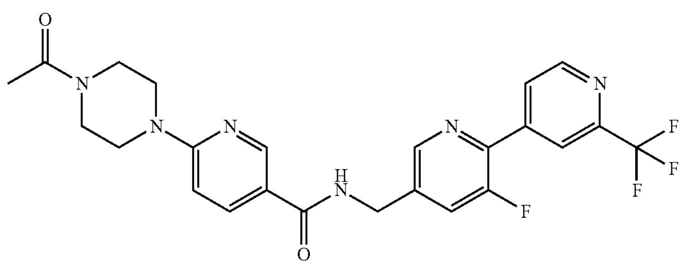 [SMILES: CC(=O)N1CCN(c2ccc(C(=O)NCc3cnc(-c4ccnc(C(F)(F)F)c4)c(F)c3)cn2)CC1] | 502.46 | 1.459 | 4.2 |
| 47 | 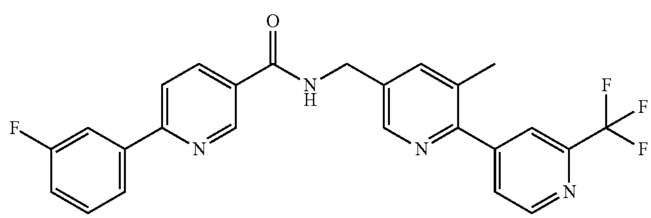 [SMILES: Cc1cc(CNC(=O)c2ccc(-c3cccc(F)c3)nc2)cnc1-c1ccnc(C(F)(F)F)c1] | 466.43 | 2.57 | 0.26 |
| 48 | 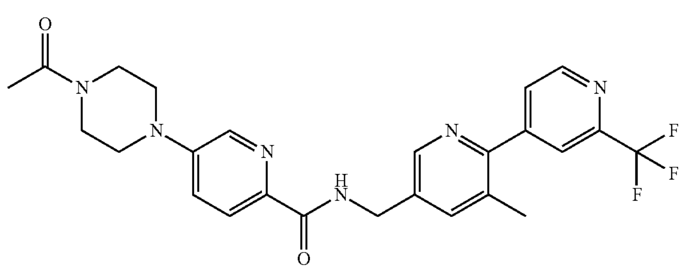 [SMILES: CC(=O)N1CCN(c2ccc(C(=O)NCc3cnc(-c4ccnc(C(F)(F)F)c4)c(C)c3)nc2)CC1] | 498.5 | 1.989 | 26 |
| 49 | 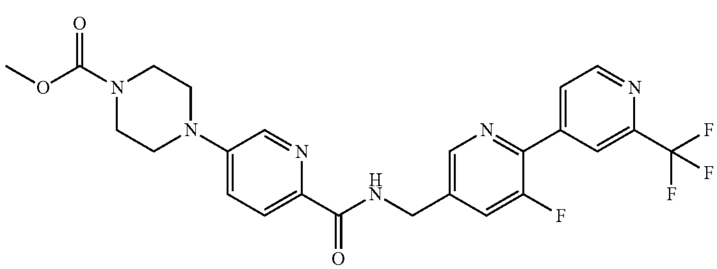 [SMILES: COC(=O)N1CCN(c2ccc(C(=O)NCc3cnc(-c4ccnc(C(F)(F)F)c4)c(F)c3)nc2)CC1] | 518.46 | 2.152 | 0.24 |

TABLE 1-continued

| Ex. | Structure | MS (m/z) (M + 1) | LC retention time (min) | IC$_{50}$ (nM) |
| --- | --- | --- | --- | --- |
| 50 | 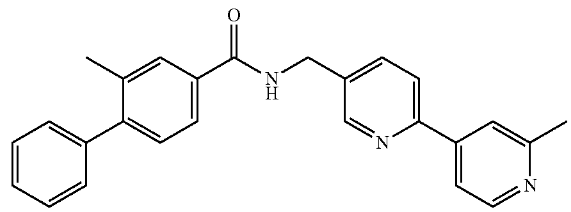 [SMILES: Cc1cc(-c2ccc(CNC(=O)c3ccc(-c4ccccc4)c(C)c3)cn2)ccn1] | 393.48 | 1.692 | 3.0 |
| 51 | 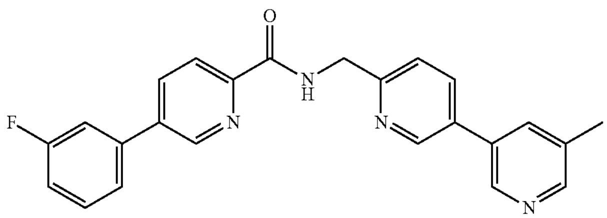 [SMILES: Cc1cncc(-c2ccc(CNC(=O)c3ccc(-c4cccc(F)c4)cn3)nc2)c1] | 398.43 | 1.519 | 0.36 |
| 52 | 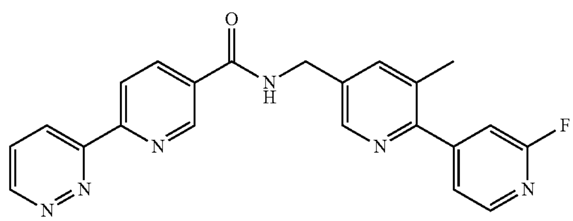 [SMILES: Cc1cc(CNC(=O)c2ccc(-c3cccnn3)nc2)cnc1-c1ccnc(F)c1] | 400.41 | 1.371 | 1.6 |
| 53 | 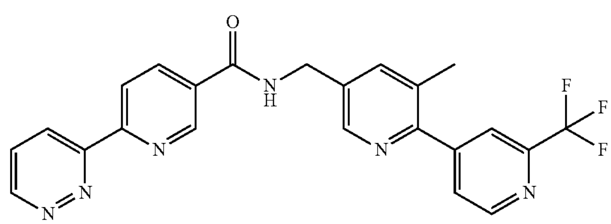 [SMILES: Cc1cc(CNC(=O)c2ccc(-c3cccnn3)nc2)cnc1-c1ccnc(C(F)(F)F)c1] | 450.42 | 1.794 | 10.2 |
| 54 | 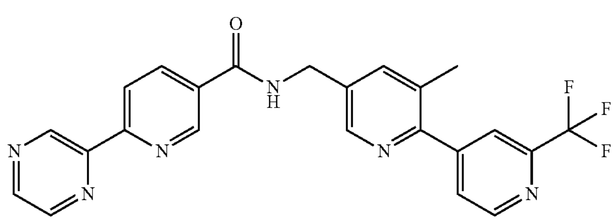 [SMILES: Cc1cc(CNC(=O)c2ccc(-c3cnccn3)nc2)cnc1-c1ccnc(C(F)(F)F)c1] | 450.42 | 1.595 | 1.2 |
| 55 | 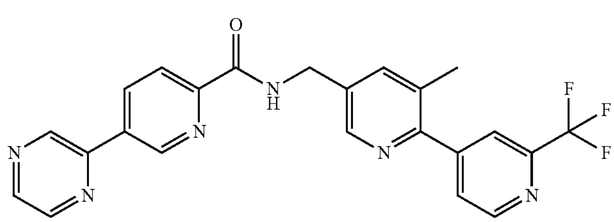 [SMILES: Cc1cc(CNC(=O)c2ccc(-c3cnccn3)cn2)cnc1-c1ccnc(C(F)(F)F)c1] | 450.42 | 2.179 | 0.80 |
| 56 | 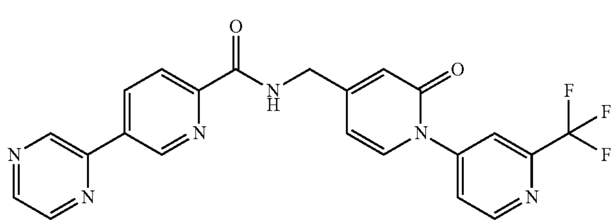 [SMILES: O=C(NCc1ccn(-c2ccnc(C(F)(F)F)c2)c(=O)c1)c1ccc(-c2cnccn2)cn1] | 452.39 | 1.474 | 34 |

TABLE 1-continued

| Ex. | Structure | MS (m/z) (M + 1) | LC retention time (min) | IC$_{50}$ (nM) |
|---|---|---|---|---|
| 57 | 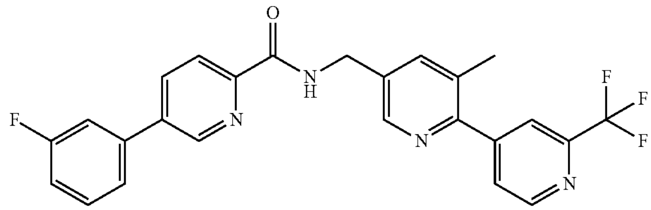 [SMILES: Cc1cc(CNC(=O)c2ccc(-c3cccc(F)c3)cn2)cnc1-c1ccnc(C(F)(F)F)c1] | 466.43 | 2.753 | 0.35 |
| 58 | 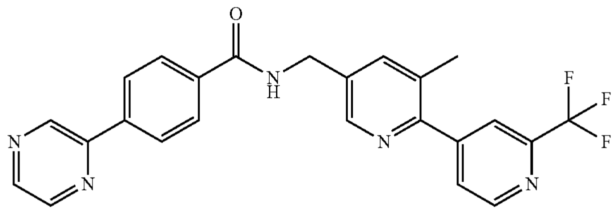 [SMILES: Cc1cc(CNC(=O)c2ccc(-c3cnccn3)cc2)cnc1-c1ccnc(C(F)(F)F)c1] | 449.43 | 1.668 | 0.41 |
| 59 | 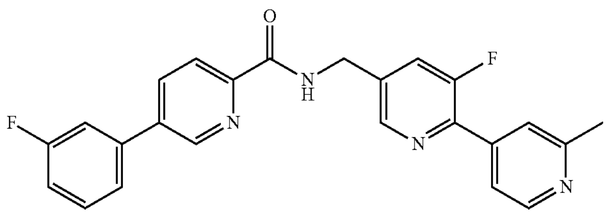 [SMILES: Cc1cc(-c2ncc(CNC(=O)c3ccc(-c4cccc(F)c4)cn3)cc2F)ccn1] | 416.42 | 1.623 | 0.29 |
| 60 | 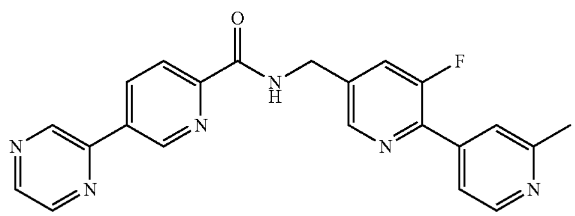 | 400.41 | 0.792 | 0.26 |
| 61 | 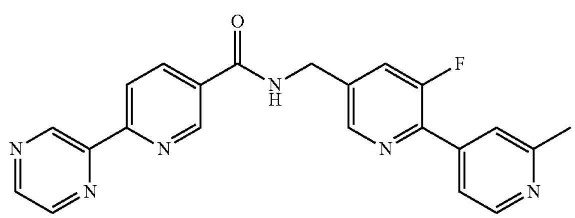 [SMILES: Cc1cc(-c2ncc(CNC(=O)c3ccc(-c4cnccn4)nc3)cc2F)ccn1] | 400.41 | 1.039 | 0.62 |
| 62 | 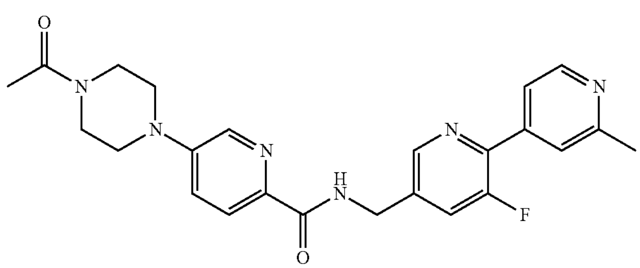 [SMILES: CC(=O)N1CCN(c2ccc(C(=O)NCc3cnc(-c4ccnc(C)c4)c(F)c3)nc2)CC1] | 448.49 | 0.985 | 11.8 |
| 63 | 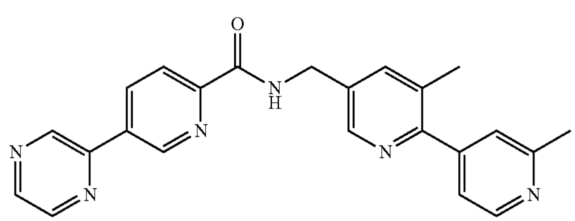 [SMILES: Cc1cc(-c2ncc(CNC(=O)c3ccc(-c4cnccn4)cn3)cc2C)ccn1] | 396.44 | 1.055 | 2.5 |

TABLE 1-continued
| Ex. | Structure | MS (m/z) (M + 1) | LC retention time (min) | IC$_{50}$ (nM) |
|---|---|---|---|---|
| 64 | 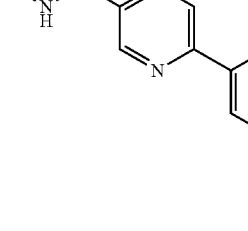 | 466.43 | 2.87 | 11 |
| 65 | 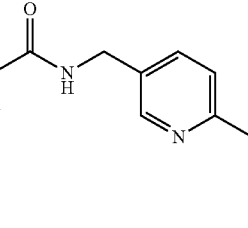 | 466.43 | 2.555 | 5.8 |
| 66 | 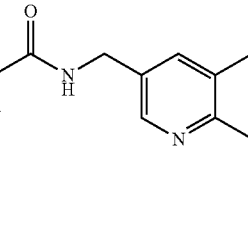 | 398.42 | 0.445 | 45 |
| 67 | 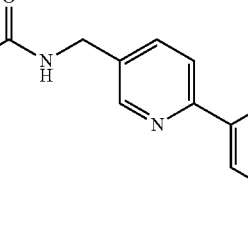 | 449.43 | 1.694 | 6.0 |
| 68 | 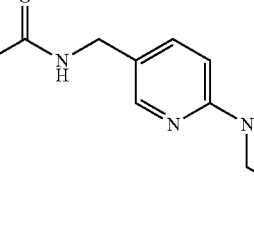 | 424.48 | 1.041 | 38 |
| 69 | 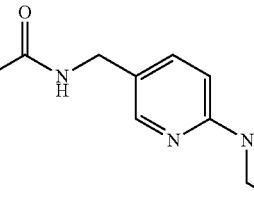 | 424.48 | 0.953 | 88 |

TABLE 1-continued

| Ex. | Structure | MS (m/z) (M + 1) | LC retention time (min) | IC$_{50}$ (nM) |
|---|---|---|---|---|
| 70 | 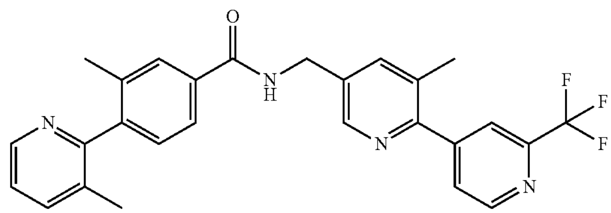 [SMILES: Cc1cc(C(=O)NCc2cnc(-c3ccnc(C(F)(F)F)c3)c(C)c2)ccc1-c1ncccc1C] | 476.49 | 1.553 | 27 |
| 71 | 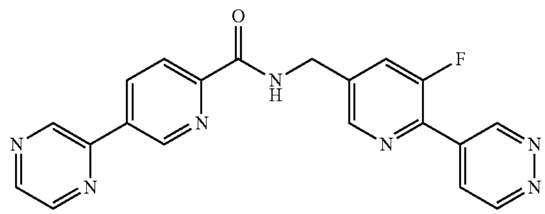 [SMILES: O=C(NCc1cnc(-c2ccnnc2)c(F)c1)c1ccc(-c2cnccn2)cn1] | 387.37 | 1.287 | 2.5 |
| 72 | 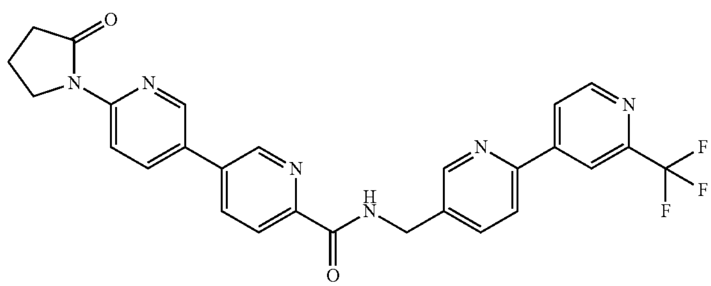 [SMILES: O=C(NCc1ccc(-c2ccnc(C(F)(F)F)c2)nc1)c1ccc(-c2ccc(N3CCCC3=O)nc2)cn1] | 518.49 | 2.384 | 1.9 |
| 73 | 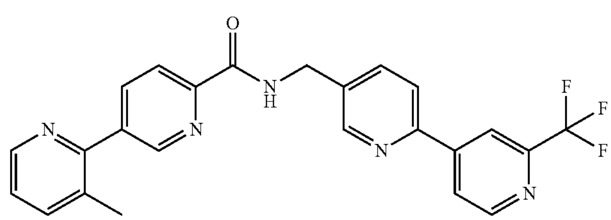 [SMILES: Cc1cccnc1-c1ccc(C(=O)NCc2ccc(-c3ccnc(C(F)(F)F)c3)nc2)nc1] | 449.43 | 1.677 | 6.0 |
| 74 | 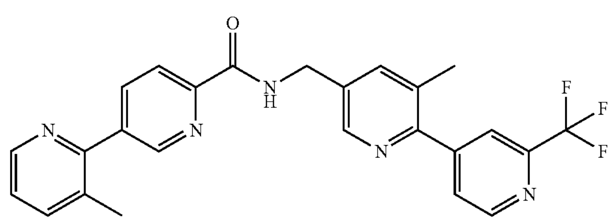 [SMILES: Cc1cccnc1-c1ccc(C(=O)NCc2cnc(-c3ccnc(C(F)(F)F)c3)c(C)c2)nc1] | 463.45 | 1.728 | 32 |
| 75 | 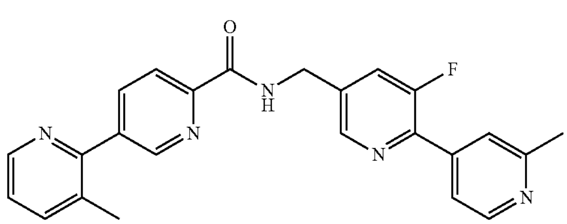 [SMILES: Cc1cc(-c2ncc(CNC(=O)c3ccc(-c4ncccc4C)cn3)cc2F)ccn1] | 413.45 | 1.257 | 6.9 |

TABLE 1-continued

| Ex. | Structure | MS (m/z) (M + 1) | LC retention time (min) | IC$_{50}$ (nM) |
|---|---|---|---|---|
| 76 | 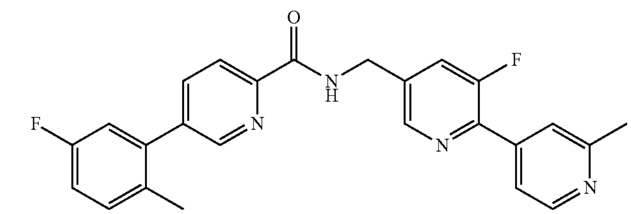 [SMILES: Cc1cc(-c2ncc(CNC(=O)c3ccc(-c4cc(F)ccc4C)cn3)cc2F)ccn1] | 430.45 | 2.034 | 1.2 |
| 77 | 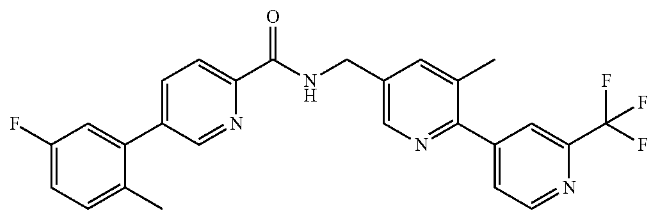 [SMILES: Cc1ccc(F)cc1-c1ccc(C(=O)NCc2cnc(-c3ccnc(C(F)(F)F)c3)c(C)c2)nc1] | 480.46 | 2.717 | 6.3 |
| 78 | 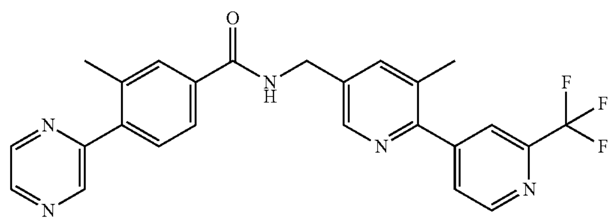 [SMILES: Cc1cc(C(=O)NCc2cnc(-c3ccnc(C(F)(F)F)c3)c(C)c2)ccc1-c1cnccn1] | 463.45 | 1.686 | 13 |
| 79 | 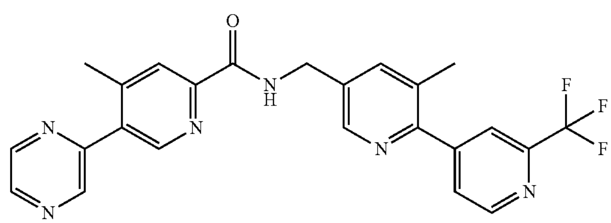 [SMILES: Cc1cc(C(=O)NCc2cnc(-c3ccnc(C(F)(F)F)c3)c(C)c2)ncc1-c1cnccn1] | 464.44 | 1.86 | 982 |
| 80 | 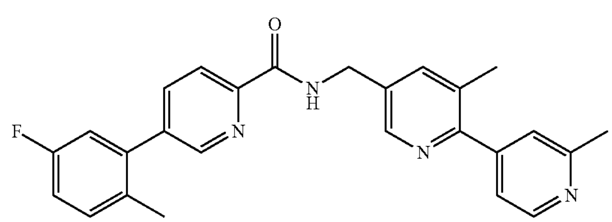 [SMILES: Cc1cc(-c2ncc(CNC(=O)c3ccc(-c4cc(F)ccc4C)cn3)cc2C)ccn1] | 426.49 | 1.653 | 4.2 |
| 81 | 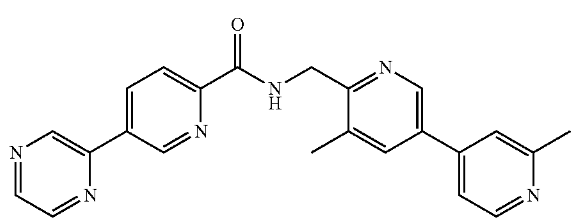 [SMILES: Cc1cc(-c2cnc(CNC(=O)c3ccc(-c4cnccn4)cn3)c(C)c2)ccn1] | 396.44 | 1.089 | 20 |
| 82 | 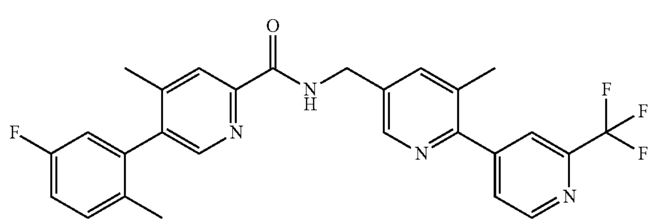 [SMILES: Cc1cc(C(=O)NCc2cnc(-c3ccnc(C(F)(F)F)c3)c(C)c2)ncc1-c1cc(F)ccc1C] | 494.48 | 2.752 | 441 |

TABLE 1-continued

| Ex. | Structure | MS (m/z) (M + 1) | LC retention time (min) | IC$_{50}$ (nM) |
|---|---|---|---|---|
| 83 | 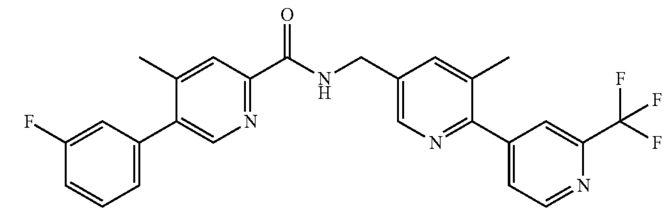 [SMILES: Cc1cc(C(=O)NCc2cnc(-c3ccnc(C(F)(F)F)c3)c(C)c2)ncc1-c1cccc(F)c1] | 480.46 | 2.368 | 812 |
| 84 | 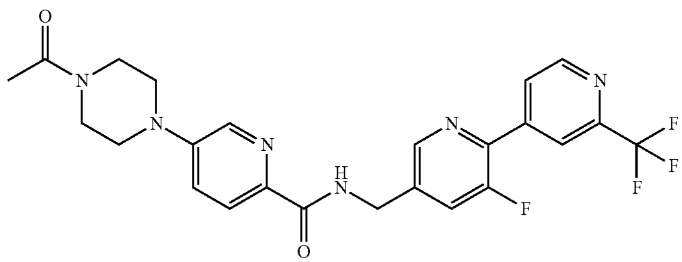 | 502.46 | 1.921 | 2.7 |
| 85 | 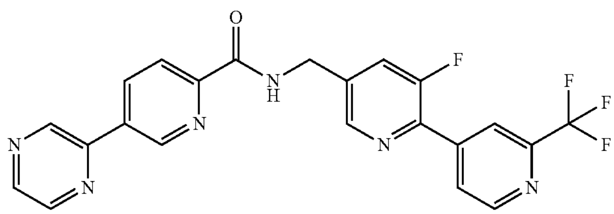 | 454.38 | 2.399 | 0.22 |
| 86 | 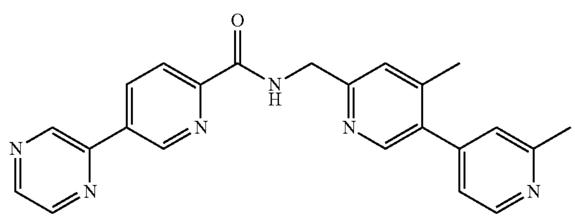 [SMILES: Cc1cc(-c2cnc(CNC(=O)c3ccc(-c4cnccn4)cn3)cc2C)ccn1] | 396.44 | 1.001 | 17 |
| 87 | 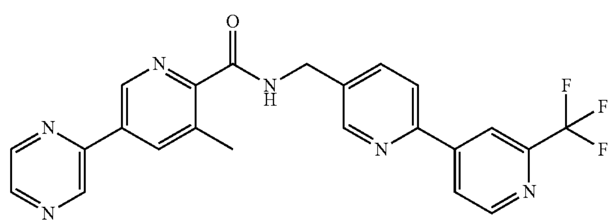 [SMILES: Cc1cc(-c2cnccn2)cnc1C(=O)NCc1ccc(-c2ccnc(C(F)(F)F)c2)nc1] | 450.42 | 1.984 | 16 |
| 88 | 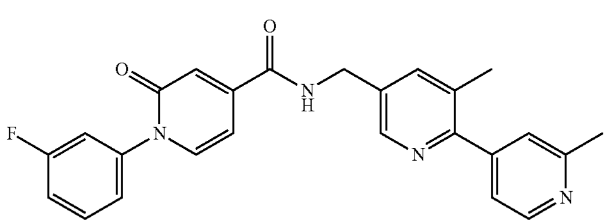 [SMILES: Cc1cc(-c2ncc(CNC(=O)c3ccn(-c4cccc(F)c4)c(=O)c3)cc2C)ccn1] | 428.46 | 1.117 | 4.4 |
| 89 | 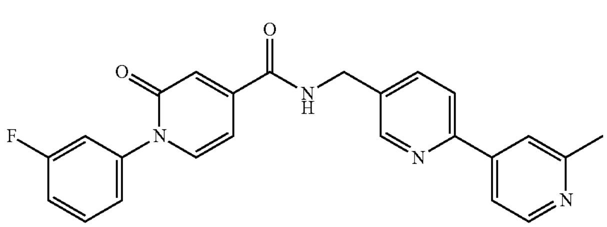 [SMILES: Cc1cc(-c2ccc(CNC(=O)c3ccn(-c4cccc(F)c4)c(=O)c3)cn2)ccn1] | 414.43 | 1.122 | 12.5 |

TABLE 1-continued
| Ex. | Structure | MS (m/z) (M + 1) | LC retention time (min) | IC$_{50}$ (nM) |
|---|---|---|---|---|
| 90 | 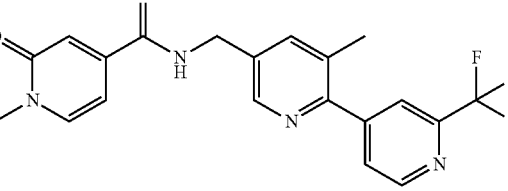 | 482.43 | 1.758 | 6.6 |
| 91 | 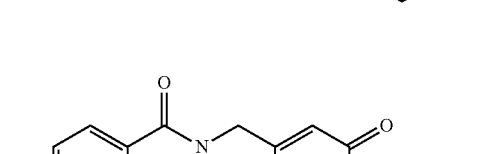 | 414.43 | 1.412 | 3.8 |
| 92 | 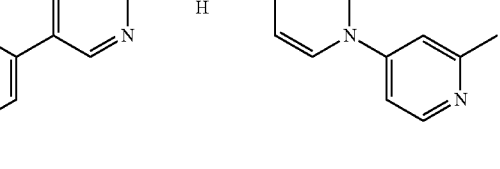 | 367.44 | 1.671 | 0.5 |
| 93 | 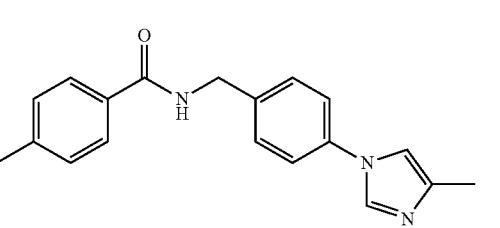 | 436.45 | 2.267 | 92 |
| 94 | 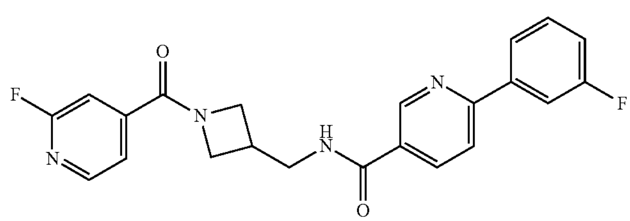 [SMILES: O=C(NCC1CN(C(=O)c2ccnc(F)c2)C1)c1ccc(-c2cccc(F)c2)nc1] | 408.4 | 1.78 | 290 |
| 95 | 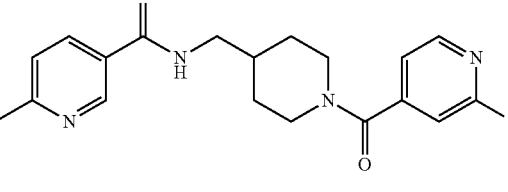 | 396.44 | 1.693 | 420 |

The following compounds have an IC$_{50}$>1 μM.

TABLE 2

| Ex. | Structure | MS (m/z) (M + 1) | IC$_{50}$ (μM) |
|---|---|---|---|
| 96 | 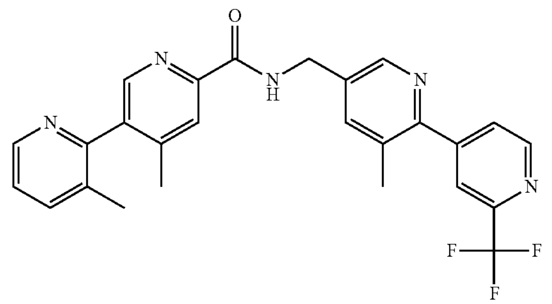 [SMILES: Cc1cc(C(=O)NCc2cnc(-c3ccnc(C(F)(F)F)c3)c(C)c2)ncc1-c1ncccc1C] | 478.2 | >2 |
| 97 | 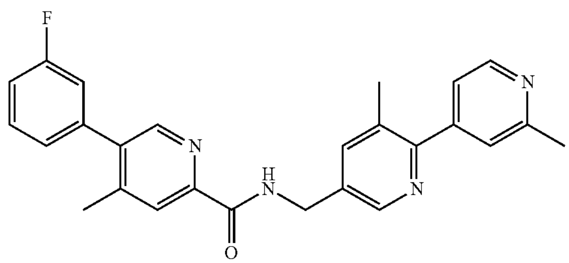 [SMILES: Cc1cc(-c2ncc(CNC(=O)c3cc(C)c(-c4cccc(F)c4)cn3)cc2C)ccn1] | 427.2 | >1.8 |
| 98 | 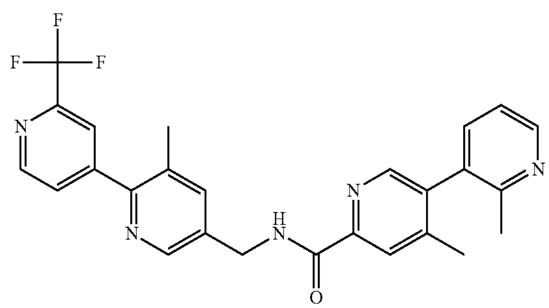 [SMILES: Cc1cc(C(=O)NCc2cnc(-c3ccnc(C(F)(F)F)c3)c(C)c2)ncc1-c1cccnc1C] | 478.2 | >1.2 |
| 99 | 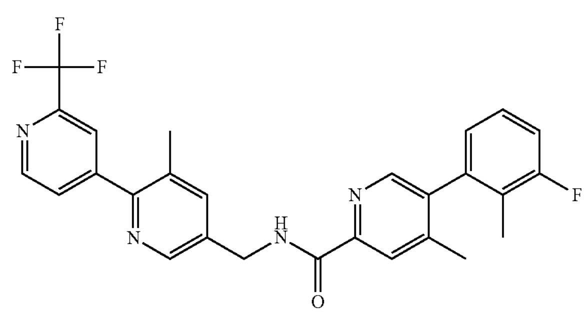 [SMILES: Cc1cc(C(=O)NCc2cnc(-c3ccnc(C(F)(F)F)c3)c(C)c2)ncc1-c1cccc(F)c1C] | 495.2 | 1.1 |
| 100 | 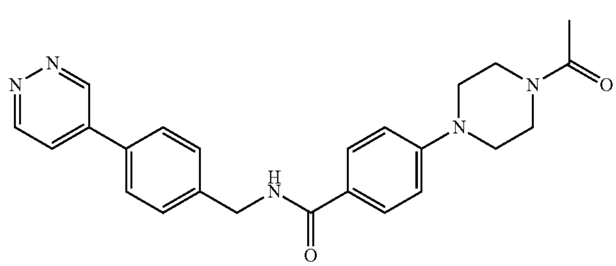 [SMILES: CC(=O)N1CCN(c2ccc(C(=O)NCc3ccc(-c4ccnnc4)cc3)cc2)CC1] | 416.2 | >20 |

Example 38

Comparative Stability Data

The stability of exemplified compounds of the invention were compared with N-(hetero)aryl, 2-(heteroy)aryl-substituted acetamides. Test compounds were dissolved or suspended in a specified media (e.g. simulated gastric fluid (SGF)). The resulting solution or suspension was kept at the testing temperature (e.g. 50° C.) for a given time (e.g. 4 hours), and the extent of degradation was quantified by LCMS using the respective UV absorption peak areas at 254 nm. Table 3 shows the percentage degradation (% degradn.) measured at 4 hrs., 8 hrs and 24 hours.

The invention claimed is:

1. A compound having Formula (1):

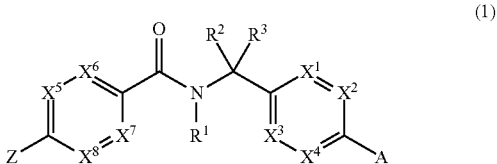

or a pharmaceutically acceptable salt thereof, wherein:

TABLE 3

| | condition | % degradn. @ 4 hr | % degradn. @ 8 hr | % degradn. @ 24 hr |
|---|---|---|---|---|
| 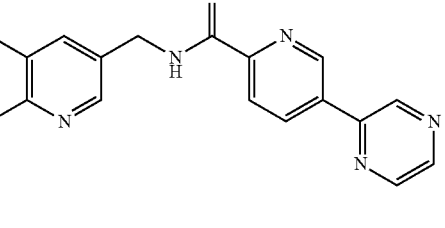 | 50° C. SGF | ~0 | ~0. | ~0 |
| 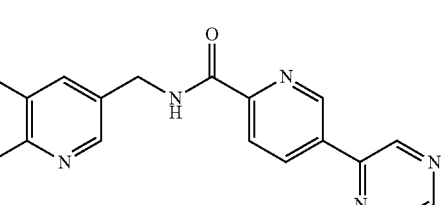 | 50° C. SGF | N/A | N/A | ~0 |
| 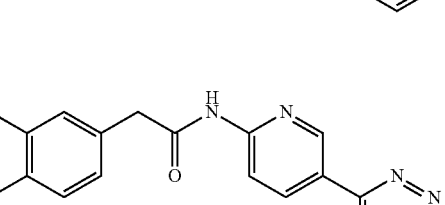 | 50° C. SGF | 11.5 | 16.6 | 26.7 |
| 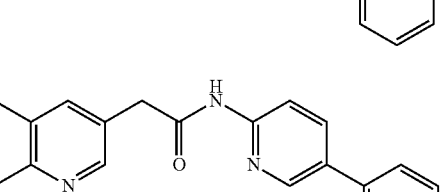 | 50° C. SGF | N/A | N/A | 25.0 |

It is understood that the examples and embodiments described herein are for illustrative purposes only and that various modifications or changes in light thereof will be suggested to persons skilled in the art and are to be included within the range and purview of this application and scope of the appended claims. All publications, patents, and patent applications cited herein are hereby incorporated by reference for all purposes.

A is

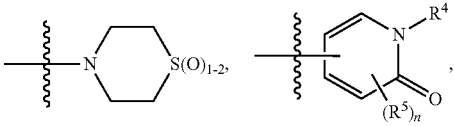

-continued

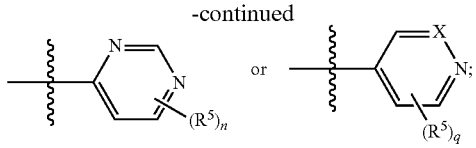

X is CH or CR⁶;
one of $X^1$, $X^2$, $X^3$ and $X^4$ is N and the others are $CR^{11}$;
one of $X^5$, $X^6$, $X^7$ and $X^8$ is N and the others are $CR^{12}$;
Z is a 5-6 membered heteroaryl, wherein said heteroaryl contains 1-2 nitrogen atoms, and Z is unsubstituted or substituted by 1-2 $R^7$ groups;
$R^1$, $R^2$, $R^3$ and $R^4$ are hydrogen or $C_{1-6}$ alkyl;
$R^5$ and $R^6$ are independently halo, cyano, $C_{1-6}$alkoxy, $S(O)_2 R^{10}$, or a $C_{1-6}$ alkyl unsubstituted or substituted with halo;
$R^7$ is hydrogen, halo, cyano, $C_{1-6}$alkoxy; $C_{1-6}$ alkyl, which is unsubstituted or substituted by halo, amino, hydroxy, alkoxy or cyano; -L-W, $NR^8R^9$, $-L-C(O)R^{10}$, $-L-C(O)OR^{10}$, $-L-C(O)NR^8R^9$, $OR^9$, $-L-S(O)_2R^{10}$ or $-L-S(O)_2NR^8R^9$;
$R^8$ and $R^9$ are independently hydrogen or -L-W; or $C_{1-6}$ alkyl, which is unsubstituted or substituted by halo, amino, hydroxy, alkoxy or cyano; or alternatively, $R^8$ and $R^9$ together with the nitrogen atom to which they are attached may form pyrrolidinyl, 2-oxopyrrolidinyl or piperidinyl;
$R^{10}$ is $C_{1-6}$ alkyl or -L-W;
$R^{11}$ and $R^{12}$ are independently hydrogen, halo, cyano, $C_{1-6}$alkoxy, or a $C_{1-6}$ alkyl unsubstituted or substituted by halo;
L is a single bond or $(CR_2)_{1-4}$ wherein each R is independently H or $C_{1-6}$ alkyl;
W is $C_{3-7}$cycloalkyl or a 5-6 membered heterocyclic ring; and
n and q are independently 0, 1, 2 or 3.

2. The compound of claim 1, wherein Z is pyridinyl unsubstituted or substituted by $C_{1-6}$ alkyl or $NR^8R^9$; or pyridazinyl, pyrazinyl, or pyrimidinyl;
$R^8$ and $R^9$ are independently hydrogen or $C_{1-6}$ alkyl; or alternatively, $R^8$ and $R^9$ together with the nitrogen atom to which they are attached form 2-oxopyrrolidinyl;
$R^{10}$ is $C_{1-6}$ alkyl; and
L is a single bond.

3. The compound of claim 2, wherein Z is pyridinyl, pyridazinyl, pyrazinyl or pyrimidinyl.

4. The compound of claim 1, wherein A is

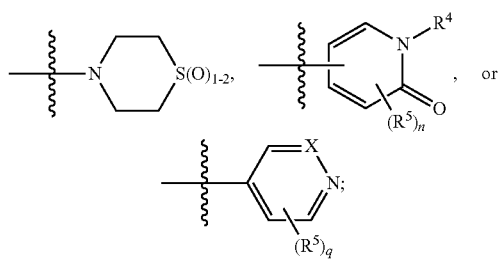

X is CH or CR⁶;
$R^1$, $R^2$ and $R^3$ are hydrogen;
$R^4$ is hydrogen or $C_{1-6}$ alkyl;
$R^5$ and $R^6$ are independently halo, or a $C_{1-6}$ alkyl unsubstituted or substituted with halo;

$R^7$ is halo, cyano, $C_{1-6}$ alkyl, $NR^8R^9$, $-L-C(O)R^{10}$, $-L-C(O)OR^{10}$ or $-L-S(O)_2R^{10}$ wherein L is a single bond;
$R^8$ and $R^9$ are independently hydrogen or $C_{1-6}$ alkyl; or alternatively, $R^8$ and $R^9$ together with the nitrogen atom to which they are attached form pyrrolidinyl, 2-oxopyrrolidinyl or piperidinyl;
$R^{10}$ is $C_{1-6}$ alkyl;
$R^{11}$ and $R^{12}$ are independently hydrogen, halo or $C_{1-6}$ alkyl; and
n and q are independently 0 or 1.

5. The compound of claim 1, wherein said compound is of Formula (2):

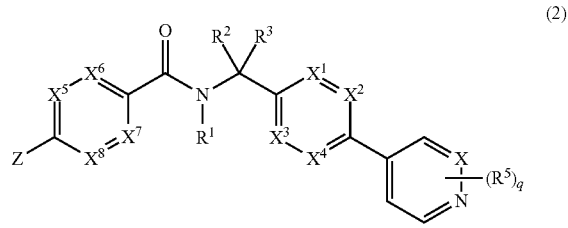

or a pharmaceutically acceptable salt thereof.

6. The compound of claim 1, wherein said compound is of Formula (2A):

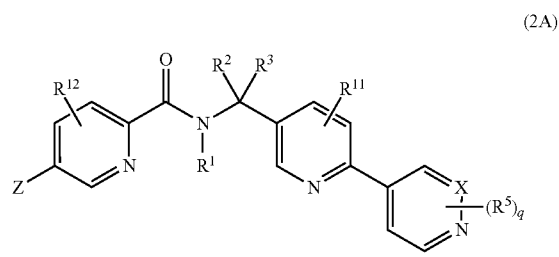

or a pharmaceutically acceptable salt thereof, wherein:
X is CH or CR⁶;
$R^1$, $R^2$ and $R^3$ are hydrogen;
$R^5$ and $R^6$ are independently halo, or a $C_{1-6}$ alkyl unsubstituted or substituted with halo;
q is 0;
$R^7$ is halo, cyano, $C_{1-6}$ alkyl, $NR^8R^9$, $-L-C(O)R^{10}$, $-L-C(O)OR^{10}$ or $-L-S(O)_2R^{10}$ wherein L is a single bond;
$R^8$ and $R^9$ are independently hydrogen or $C_{1-6}$ alkyl; or alternatively, $R^8$ and $R^9$ together with the nitrogen atom to which they are attached form pyrrolidinyl, 2-oxopyrrolidinyl or piperidinyl;
$R^{10}$ is $C_{1-6}$ alkyl;
$R^{11}$ is hydrogen, halo or methyl; and
$R^{12}$ is hydrogen or methyl.

7. The compound of claim 1, wherein X is CH or CR⁶; and $R^6$ is halo, methyl or trifluoromethyl.

8. The compound of claim 1, wherein said compound is selected from:
wherein said compound is selected from:
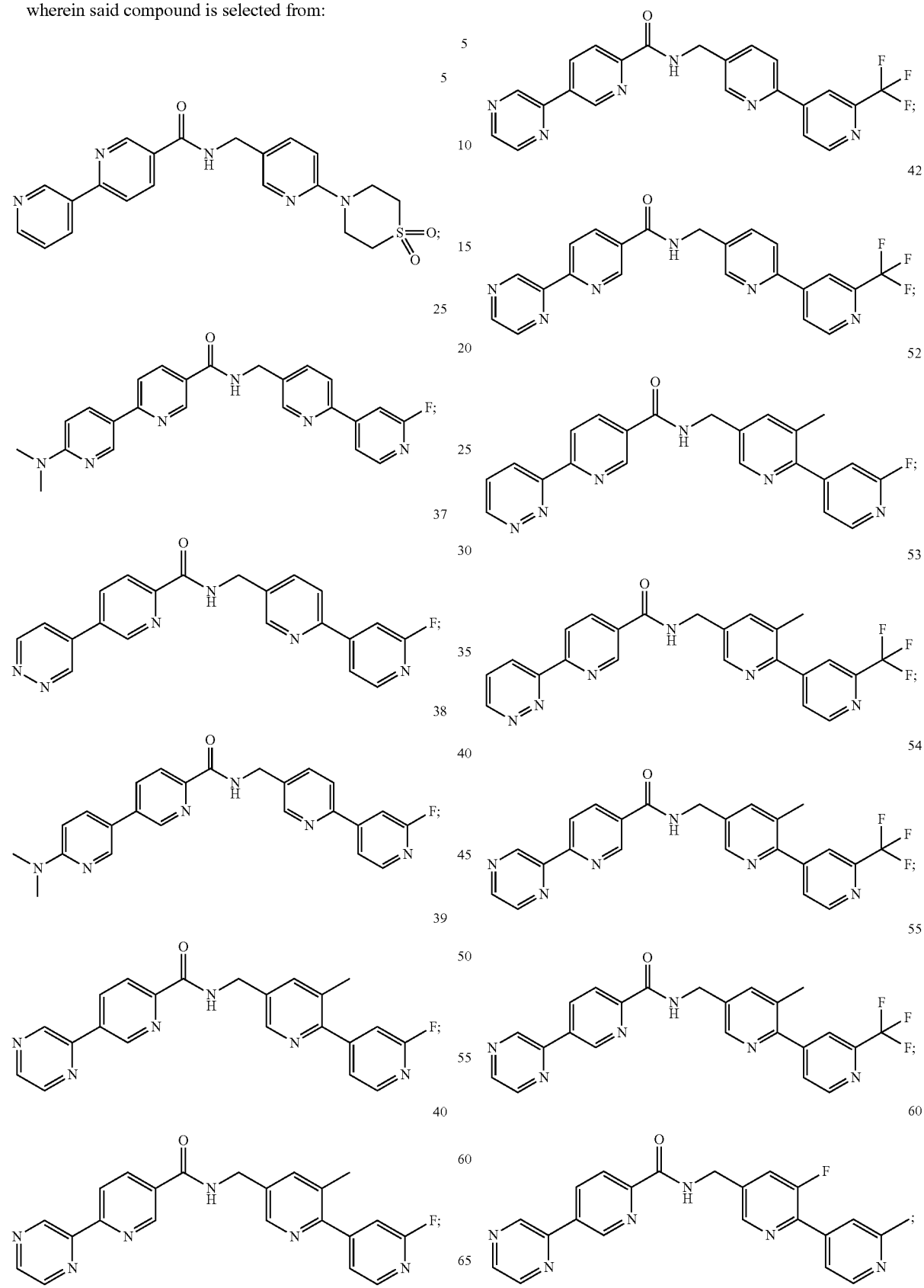

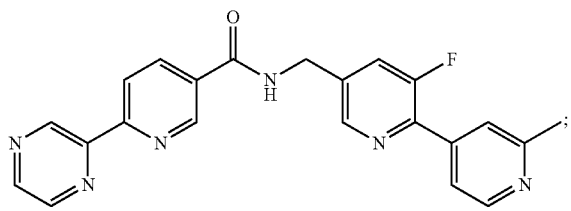
61
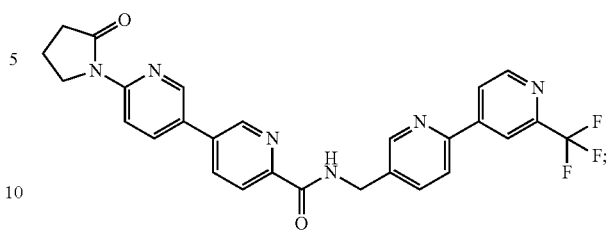
72
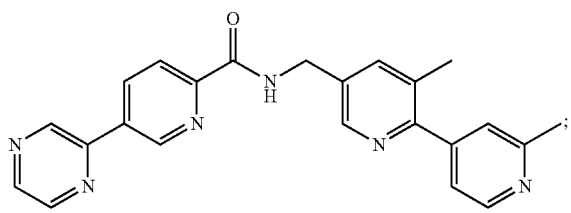
63
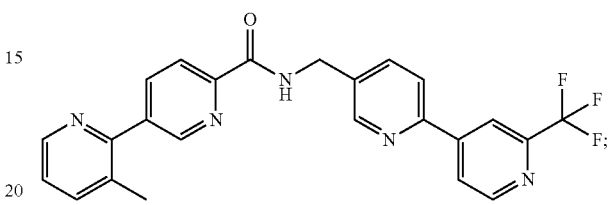
73
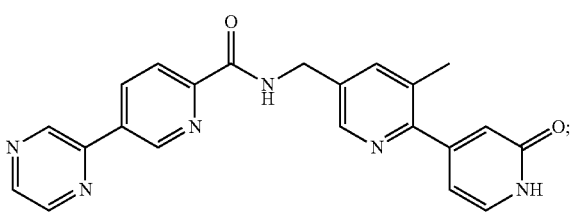
66
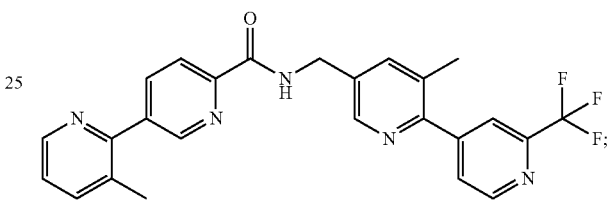
74
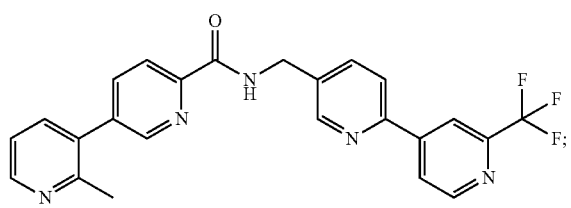
67
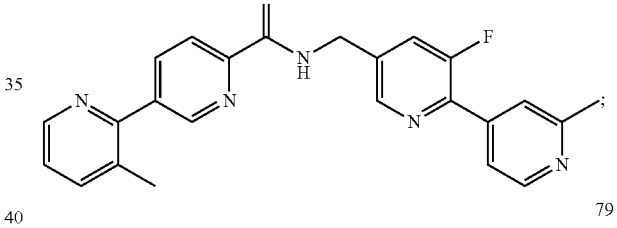
75
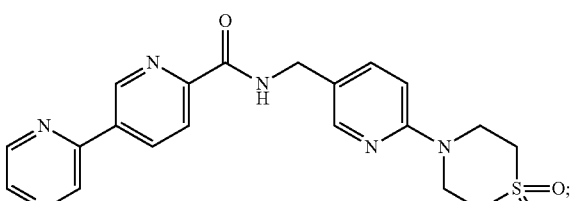
68
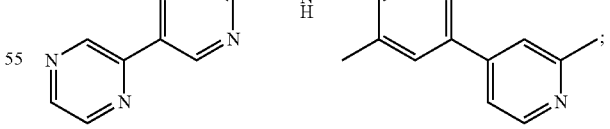
79
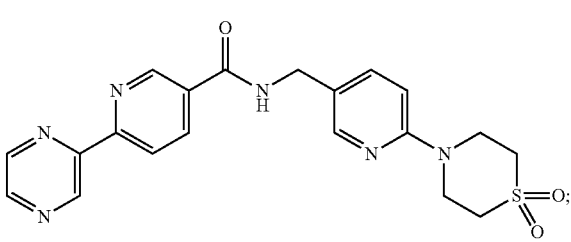
69
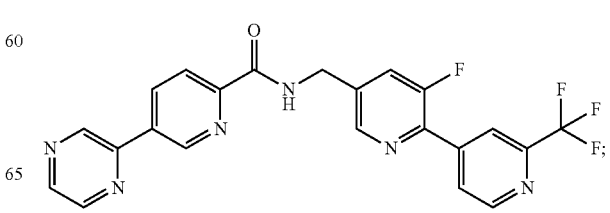
81
85

-continued

86

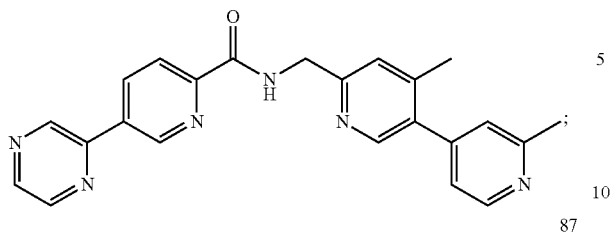

87

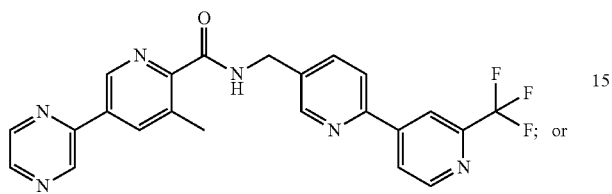

a pharmaceutically acceptable salt thereof.

9. A pharmaceutical composition comprising a therapeutically effective amount of a compound of claim 1 and a pharmaceutically acceptable carrier.

10. A pharmaceutical composition comprising a therapeutically effective amount of a compound of claim 8 and a pharmaceutically acceptable carrier.

11. A combination comprising a therapeutically effective amount of a compound of claim 1 and a chemotherapeutic agent.

12. A combination comprising a therapeutically effective amount of a compound of claim 8 and a chemotherapeutic agent.

13. A method for inhibiting Wnt signaling in a cell, comprising contacting the cell with an effective amount of a compound of claim 1, or a pharmaceutically acceptable salt thereof.

14. A method for inhibiting a porcupine gene in a cell, comprising contacting the cell with an effective amount of a compound of claim 1, or a pharmaceutically acceptable salt thereof.

15. A process for the production of a compound of Formula (2A), (2A)

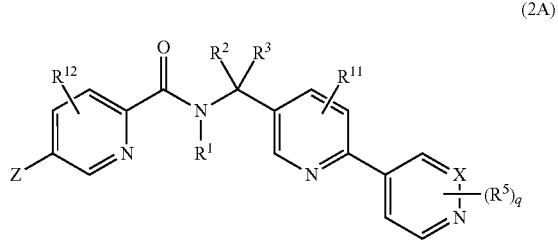

comprising reacting a compound of Formula (5)

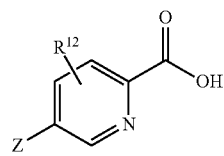

with a compound of Formula (6)

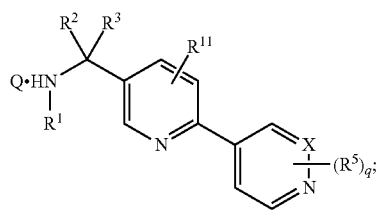

wherein X is CH or $CR^6$;

Z is 5-6 membered heteroaryl containing 1-2 nitrogen atoms, wherein said heteroaryl is unsubstituted or substituted by 1-2 $R^7$ groups;

$R^1$, $R^2$ and $R^3$ are hydrogen;

$R^5$ and $R^6$ are independently halo, or a $C_{1-6}$ alkyl unsubstituted or substituted by halo;

q is 0;

$R^7$ is halo, cyano, $C_{1-6}$ alkyl, $NR^8R^9$, -L-C(O)$R^{10}$, -L-C(O)OR$^{10}$ or -L-S(O)$_2R^{10}$ wherein L is a single bond;

$R^8$ and $R^9$ are independently hydrogen or $C_{1-6}$ alkyl; or alternatively, $R^8$ and $R^9$ together with the nitrogen atom to which they are attached form pyrrolidinyl, 2-oxopyrrolidinyl or piperidinyl;

$R^{10}$ is $C_{1-6}$ alkyl;

$R^{11}$ is hydrogen, halo or methyl; and $R^{12}$ is hydrogen or methyl;

Q is an organic acid or inorganic acid; and recovering the compound of Formula (2A) or a pharmaceutically acceptable salt thereof, and (i) optionally converting the compound of Formula (2A) into a pharmaceutically acceptable salt thereof, or (ii) optionally converting the pharmaceutically acceptable salt of the compound of formula (2A) into another pharmaceutically acceptable salt.

* * * * *